United States Patent
Stulen et al.

(10) Patent No.: US 10,172,636 B2
(45) Date of Patent: Jan. 8, 2019

(54) ARTICULATION FEATURES FOR ULTRASONIC SURGICAL INSTRUMENT

(71) Applicant: Ethicon Endo-Surgery, Inc., Cincinnati, OH (US)

(72) Inventors: Foster B. Stulen, Mason, OH (US); David A. Monroe, Cincinnati, OH (US); William B. Weisenburgh, II, Maineville, OH (US); Richard C. Smith, Milford, OH (US); Ashvani K. Madan, Mason, OH (US); Craig T. Davis, Cincinnati, OH (US); Barry C. Worrell, Centerville, OH (US); Benjamin D. Dickerson, Cincinnati, OH (US); Chad P. Boudreaux, Cincinnati, OH (US); Thomas C. Gallmeyer, Cincinnti, OH (US); Amy L. Benchek, Cincinnati, OH (US); Tylor C. Muhlenkamp, Cincinnati, OH (US); Sean P. Conlon, Loveland, OH (US); John A. Hibner, Mason, OH (US)

(73) Assignee: Ethicon LLC, Guaynabo, PR (US)

( * ) Notice: Subject to any disclaimer, the term of this patent is extended or adjusted under 35 U.S.C. 154(b) by 499 days.

(21) Appl. No.: 14/028,717

(22) Filed: Sep. 17, 2013

(65) Prior Publication Data
US 2015/0080924 A1    Mar. 19, 2015

(51) Int. Cl.
*A61B 17/32* (2006.01)
*A61B 17/00* (2006.01)

(52) U.S. Cl.
CPC ......... *A61B 17/320092* (2013.01); *A61B 17/320068* (2013.01); *A61B 2017/00309* (2013.01);
(Continued)

(58) Field of Classification Search
CPC ........ A61B 19/2203; A61B 2019/2242; A61B 2019/2234
See application file for complete search history.

(56) References Cited

U.S. PATENT DOCUMENTS

| | | | |
|---|---|---|---|
| 5,322,055 A | 6/1994 | Davison et al. | |
| 5,873,873 A | 2/1999 | Smith et al. | |

(Continued)

FOREIGN PATENT DOCUMENTS

| | | |
|---|---|---|
| CN | 103263242 A | 8/2013 |
| EP | 1621151 A2 | 2/2006 |

(Continued)

OTHER PUBLICATIONS

International Search Report and Written Opinion dated May 7, 2015 for Application No. PCT/US2014/053834
(Continued)

*Primary Examiner* — Katherine M Shi
*Assistant Examiner* — Michael Mendoza
(74) *Attorney, Agent, or Firm* — Frost Brown Todd LLC

(57) ABSTRACT

A surgical apparatus comprises a body, an ultrasonic transducer, a shaft, an acoustic waveguide, an articulation section, an end effector, and an articulation drive assembly. The ultrasonic transducer is operable to convert electrical power into ultrasonic vibrations. The shaft couples the end effector and the body together. The acoustic waveguide is coupled with the transducer. The articulation section includes a collar that is located distal to a nodal portion of the waveguide and is operable to deflect the end effector away from the longitudinal axis. The end effector comprises an ultrasonic blade in acoustic communication with the ultrasonic transducer. The articulation drive assembly is operable to drive articulation of the articulation section. The articulation drive assembly comprises at least one translating articulation
(Continued)

driver coupled with the collar. The ultrasonic blade is operable to deliver ultrasonic vibrations to tissue even when the articulation section is in an articulated state.

10 Claims, 38 Drawing Sheets

(52) U.S. Cl.
CPC .............. *A61B 2017/00314* (2013.01); *A61B 2017/00327* (2013.01); *A61B 2017/00336* (2013.01); *A61B 2017/00473* (2013.01); *A61B 2017/320072* (2013.01)

(56) References Cited

U.S. PATENT DOCUMENTS

| | | | |
|---|---|---|---|
| 5,897,523 A | 4/1999 | Wright et al. | |
| 5,980,510 A | 11/1999 | Tsonton et al. | |
| 5,989,264 A | 11/1999 | Wright | |
| 6,051,010 A | 4/2000 | DiMatteo et al. | |
| 6,063,098 A | 5/2000 | Houser et al. | |
| 6,090,120 A | 7/2000 | Wright et al. | |
| 6,325,811 B1 | 12/2001 | Messerly | |
| 6,387,109 B1 | 5/2002 | Davison et al. | |
| 6,454,782 B1 | 9/2002 | Schwemberger | |
| 6,589,200 B1 | 7/2003 | Schwemberger et al. | |
| 6,752,815 B2 | 6/2004 | Beaupre | |
| 6,773,444 B2 | 8/2004 | Messerly | |
| 6,783,524 B2 * | 8/2004 | Anderson ...... | A61B 17/320068 606/1 |
| 6,855,123 B2 | 2/2005 | Nita | |
| 7,135,030 B2 | 11/2006 | Schwemberger et al. | |
| 7,621,930 B2 | 11/2009 | Houser | |
| 8,461,744 B2 | 6/2013 | Wiener et al. | |
| 8,475,453 B2 | 7/2013 | Marczyk et al. | |
| 8,591,536 B2 | 11/2013 | Robertson | |
| 8,623,027 B2 | 1/2014 | Price et al. | |
| 8,870,867 B2 | 10/2014 | Walberg et al. | |
| 9,095,367 B2 | 8/2015 | Olson et al. | |
| 9,179,912 B2 | 11/2015 | Yates et al. | |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2010/0069940 A1 | 3/2010 | Miller et al. | |
| 2010/0249497 A1 | 9/2010 | Peine et al. | |
| 2011/0087212 A1 | 4/2011 | Aldridge et al. | |
| 2011/0295269 A1 * | 12/2011 | Swensgard ...... | A61B 17/07207 606/130 |
| 2012/0078247 A1 | 3/2012 | Worrell et al. | |
| 2012/0112687 A1 | 5/2012 | Houser et al. | |
| 2012/0116265 A1 | 5/2012 | Houser et al. | |
| 2013/0012958 A1 | 1/2013 | Marczyk et al. | |
| 2013/0023868 A1 | 1/2013 | Worrell et al. | |
| 2013/0197511 A1 | 8/2013 | Balanev et al. | |
| 2013/0211397 A1 | 8/2013 | Parihar et al. | |
| 2013/0289592 A1 | 10/2013 | Stulen et al. | |
| 2014/0005701 A1 | 1/2014 | Olson et al. | |
| 2014/0005703 A1 | 1/2014 | Stulen et al. | |
| 2014/0276931 A1 | 9/2014 | Parihar et al. | |

FOREIGN PATENT DOCUMENTS

| | | |
|---|---|---|
| EP | 2090245 A1 | 8/2009 |
| EP | 2586382 A2 | 5/2013 |
| JP | H10-043189 A | 2/1998 |
| JP | 2006-051347 A | 2/2006 |
| JP | 2006-334268 A | 12/2006 |
| JP | 2007-082624 A | 4/2007 |
| JP | 2009-512497 A | 3/2009 |
| JP | 2011-240148 A | 12/2011 |
| JP | 2013-150853 A | 8/2013 |
| KR | 2012-0022521 A | 3/2012 |

OTHER PUBLICATIONS

U.S. Appl. No. 13/657,553, filed Oct. 22, 2012.
U.S. Appl. No. 61/410,603, filed Nov. 5, 2010.
Chinese Search Report dated Dec. 21, 2017 for Application No. CN 201480062707.3, 1 pg.
European Exam Report dated Sep. 22, 2017 for Application No. EP 14771674.0, 5 pgs.
Japanese Office Action, Notification of Reasons for Refusal, dated May 29, 2018 for Application No. JP 2016-543919, 9 pgs.
Japanese Search Report by Registered Searching Organization dated May 31, 2018 for Application No. JP 2016-543919, 26 pgs.

* cited by examiner

ARTICULATION FEATURES FOR ULTRASONIC SURGICAL INSTRUMENT

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abadoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2009/0105750, entitled "Ergonomic Surgical Instruments," published Apr. 23, 2009, now U.S. Pat. No. 8,632,027, issued on Jul. 7, 2014, the disclosure of which is incorporated by reference herein; U.S. Pub. No. 2010/0069940, entitled "Ultrasonic Device for Fingertip Control," published Mar. 18, 2010, now U.S. Pat. No. 9,023,071, issued on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, now U.S. Pat. No. 8,461,744, issued on Jun. 11, 2013, the disclosure of which is incorporated by reference herein; and U.S. Pub. No. 2012/0029546, entitled "Ultrasonic Surgical Instrument Blades," published Feb. 2, 2012, now U.S. Pat. No. 8,591,536, issued on Nov. 26, 2013, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued on Jul. 5, 2016,the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. patent application Ser. No. 13/538,588, filed Jun. 29, 2012, now U.S. Pat. No. 9,393,037, issued on Jul. 19, 2016, entitled "Surgical Instruments with Articulating Shafts," the disclosure of which is incorporated by reference herein; and U.S. patent application Ser. No. 13/657,553, filed Oct. 22, 2012, now U.S. Pat. No. 9,095,367, issued on Aug. 4, 2015, entitled "Flexible Harmonic Waveguides/Blades for Surgical Instruments," the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
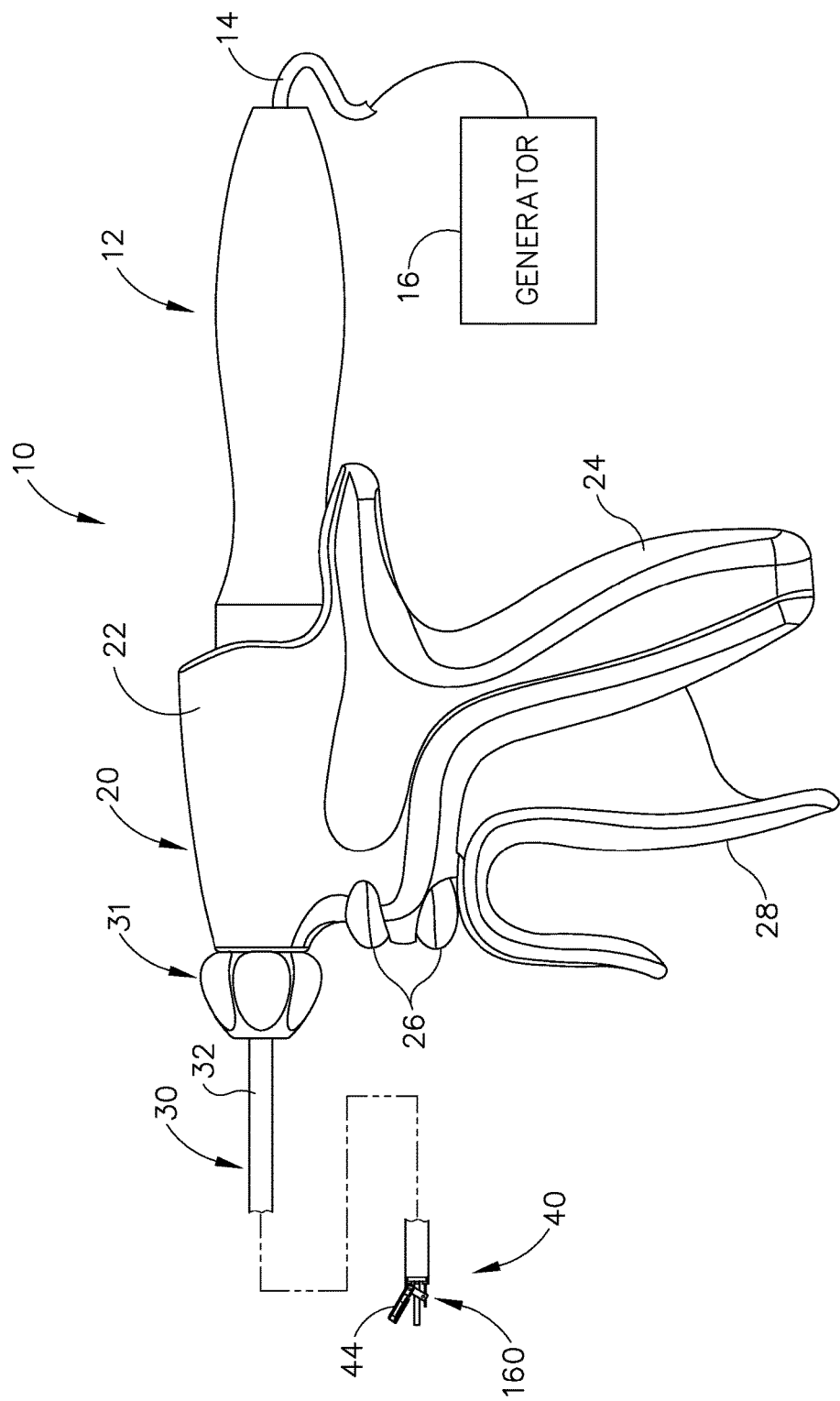
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIG. 1 illustrates an exemplary ultrasonic surgical instrument (10). At least part of instrument (10) may be constructed and operable in accordance with at least some of the teachings of U.S. Pat. No. 5,322,055; U.S. Pat. No. 5,873,873; U.S. Pat. No. 5,980,510; U.S. Pat. No. 6,325,811; U.S. Pat. No. 6,773,444; U.S. Pat. No. 6,783,524; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0105750, now U.S. Pat. No. 8,623,027, issued on Jul. 7, 2014; U.S. Pub. No. 2010/0069940, now U.S. Pat. No. 9,023,071, issued on May 5, 2015; U.S. Pub. No. 2011/0015660, U.S. Pat. No. 8,461,744, issued on Jun. 11, 2013; U.S. Pub. No. 2012/0112687, now U.S. Pat. No. 9,381,058, issued on Jul. 5, 2016; U.S. Pub. No. 2012/0116265, now abandoned; U.S. patent application Ser. No. 13/538,588, now U.S. Pat. No. 9,393,037, issued Jul. 19, 2016; U.S. patent application Ser. No. 13/657,553, now U.S. Pat. No. 9,095,367, issued Aug. 4, 2015; and/or U.S. Pat. App. No. 61/410,603. The disclosures of each of the foregoing patents, publications, and applications are incorporated by reference herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (10) of the present example comprises a handle assembly (20), a shaft assembly (30), and an end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. End effector (40) includes an ultrasonic blade (160) and a pivoting clamp arm (44). Clamp arm (44) is coupled with trigger (28) such that clamp arm (44) is pivotable toward ultrasonic blade (160) in response to pivoting of trigger (28) toward pistol grip (24); and such that clamp arm (44) is pivotable away from ultrasonic blade (160) in response to pivoting of trigger (28) away from pistol grip (24). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (12) extends proximally from body (22) of handle assembly (20). Transducer assembly (12) is coupled with a generator (16) via a cable (14). Transducer assembly (12) receives electrical power from generator (16) and converts that power into ultrasonic vibrations through piezoelectric principles. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued on Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

A. Exemplary End Effector and Acoustic Drivetrain

Figure 2:
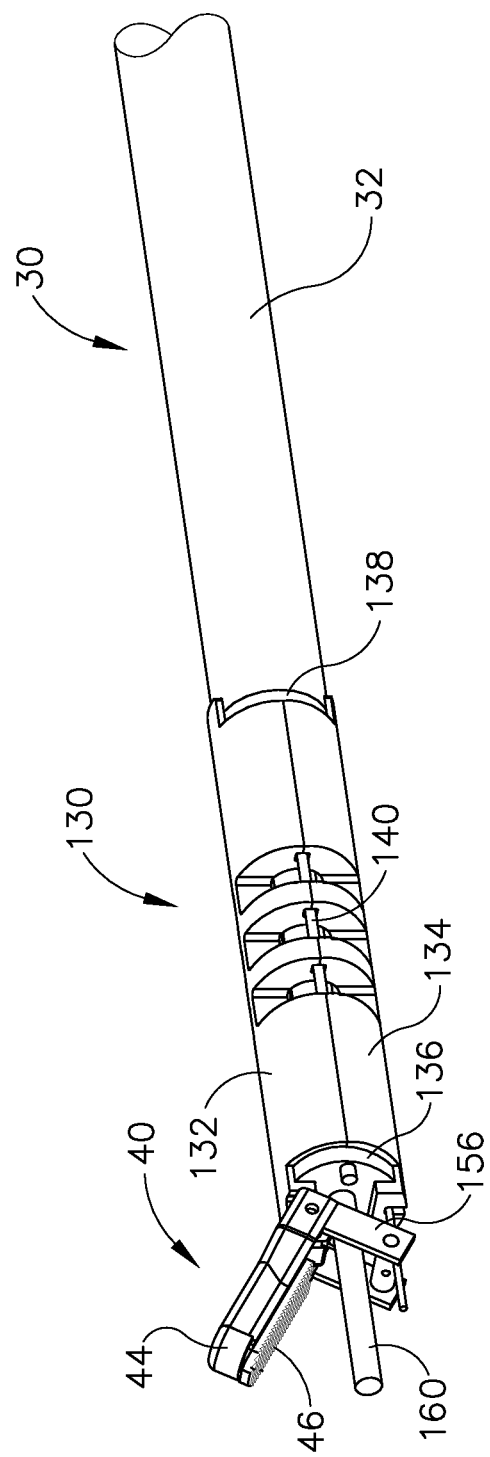
FIG. 2 depicts a perspective view of a shaft assembly and end effector of the surgical instrument of FIG. 1.
Figure 3:
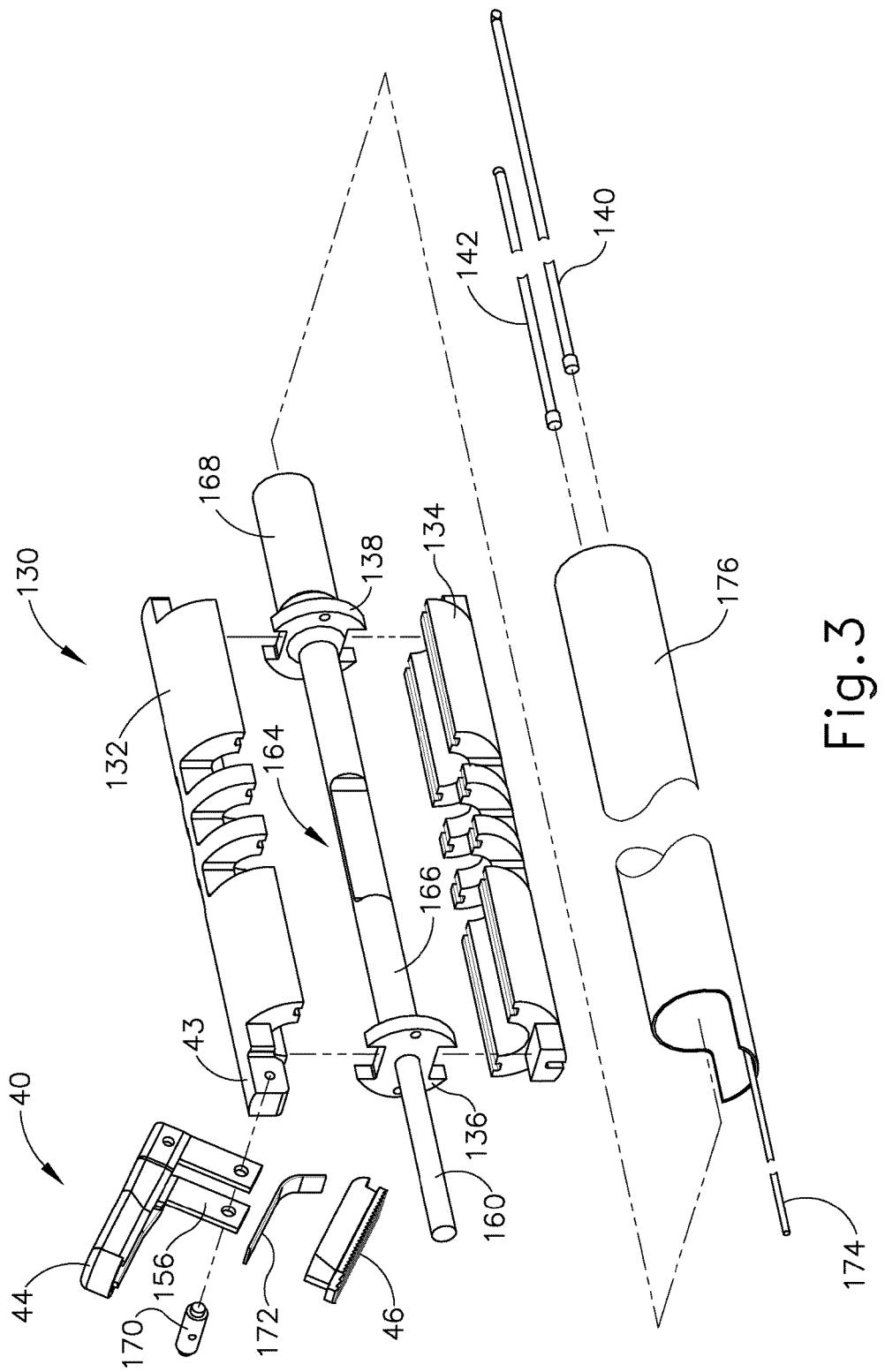
FIG. 3 depicts an exploded perspective view of the shaft assembly and end effector of FIG. 2.
Figure 4:
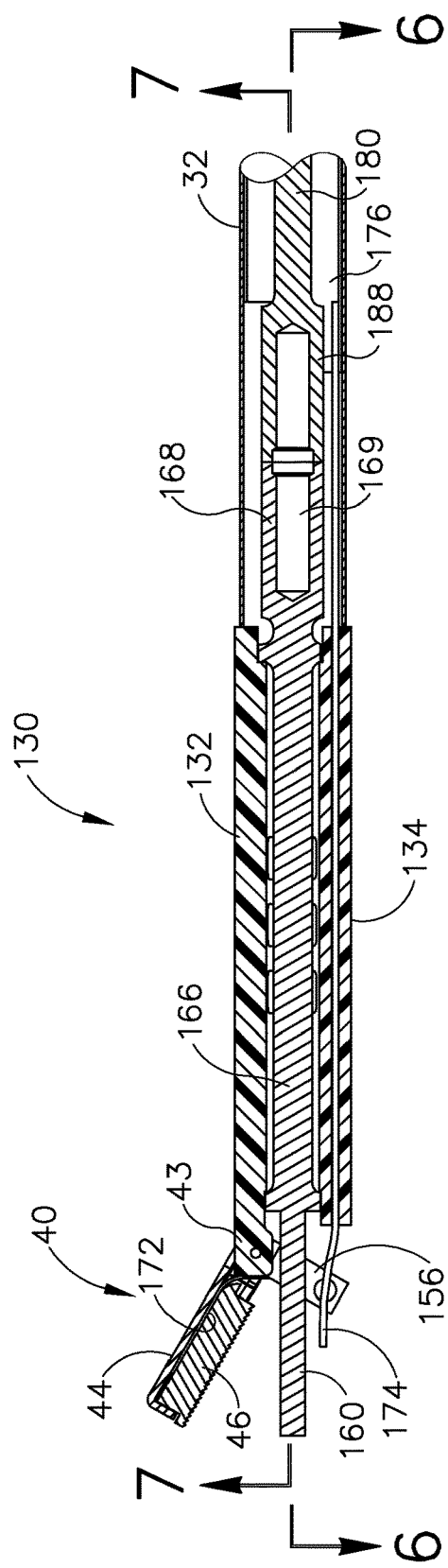
FIG. 4 depicts a cross-sectional side view of the shaft assembly and end effector of FIG. 2.
Figure 5:
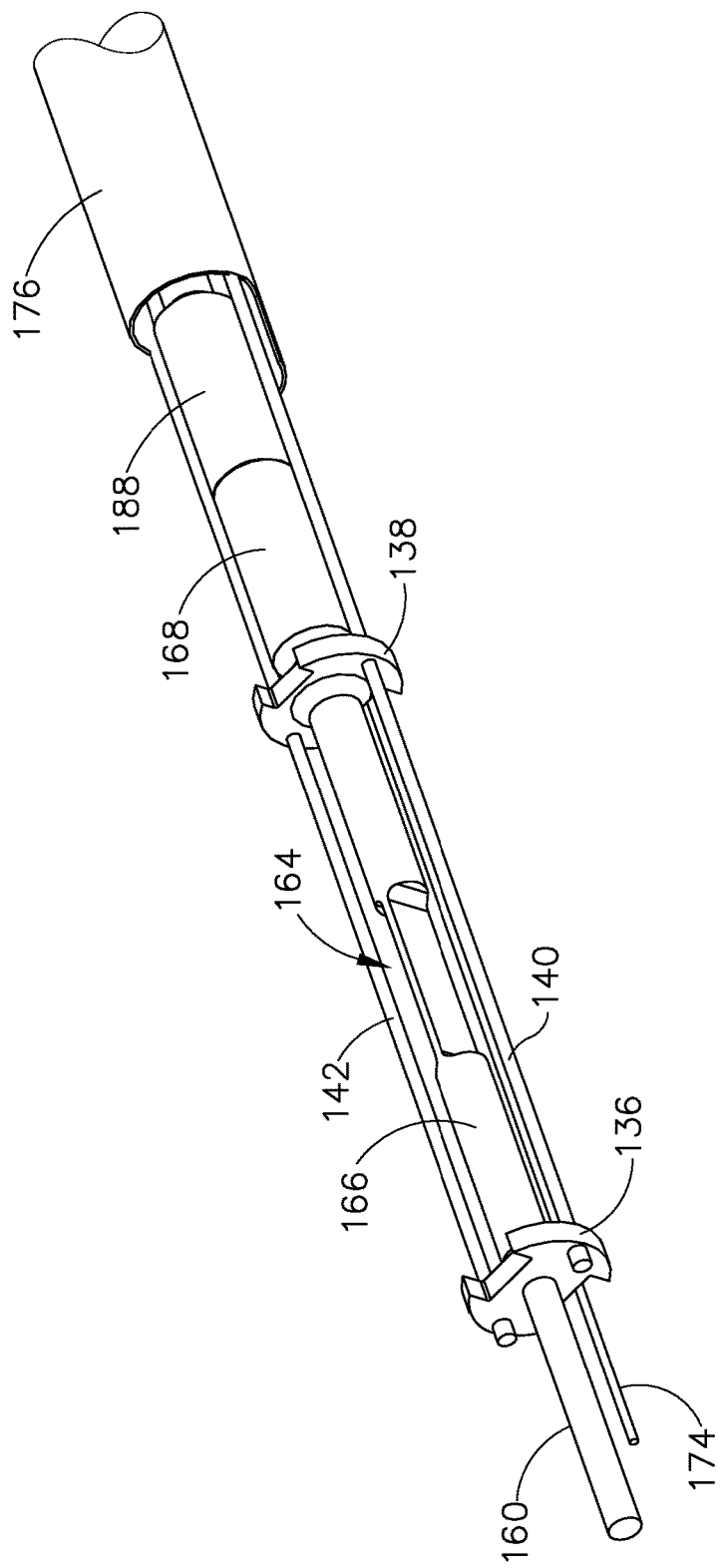
FIG. 5 depicts a perspective view of components of the shaft assembly and end effector of FIG. 2.

As best seen in FIGS. 2-4, end effector (40) of the present example comprises clamp arm (44) and ultrasonic blade (160). Clamp arm (44) includes a clamp pad (46) that is secured to the underside of clamp arm (44), facing blade (160). Clamp arm (44) is pivotally secured to a distally projecting tongue (43) of a first ribbed body portion (132), which forms part of an articulation section (130) as will be described in greater detail below. Clamp arm (44) is operable to selectively pivot toward and away from blade (160) to selectively clamp tissue between clamp arm (44) and blade (160). A pair of arms (156) extend transversely to clamp arm (44) and are secured to a pin (170) that extends laterally between arms (156). A rod (174) is secured to pin (170). Rod (174) extends distally from a closure tube (176) and is unitarily secured to closure tube (176). Closure tube (176) is operable to translate longitudinally relative to articulation section (130) to selectively pivot clamp arm (44) toward and away from blade (160). In particular, closure tube (176) is coupled with trigger (28) such that clamp arm (44) pivots toward blade (160) in response to pivoting of trigger (28) toward pistol grip (24); and such that clamp arm (44) pivots away from blade (160) in response to pivoting of trigger (28) away from pistol grip (24). A leaf spring (172) biases clamp arm (44) to the open position in the present example, such that (at least in some instances) the operator may effectively open clamp arm (44) by releasing a grip on trigger (28).

Blade (160) of the present example is operable to vibrate at ultrasonic frequencies in order to effectively cut through and seal tissue, particularly when the tissue is being clamped between clamp pad (46) and blade (160). Blade (160) is positioned at the distal end of an acoustic drivetrain. This acoustic drivetrain includes transducer assembly (12), a rigid acoustic waveguide (180), and a flexible acoustic waveguide (166). Transducer assembly (12) includes a set of piezoelectric discs (not shown) located proximal to a horn (not shown) of rigid acoustic waveguide (180). The piezoelectric discs are operable to convert electrical power into ultrasonic vibrations, which are then transmitted along rigid acoustic waveguide (180) and flexible waveguide (166) to blade (160) in accordance with known configurations and techniques. By way of example only, this portion of the acoustic drivetrain may be configured in accordance with various teachings of various references that are cited herein.

Rigid acoustic waveguide (180) distally terminates in a coupling (188), which can be seen in FIGS. 4-7. Coupling (188) is secured to coupling (168) by a double-threaded bolt (169). Coupling (168) is located at the proximal end of flexible acoustic waveguide (166). As best seen in FIGS. 3 and 5-7, flexible acoustic waveguide (166) includes a distal flange (136), a proximal flange (138), and a narrowed section (164) located between flanges (138). In the present example, flanges (136, 138) are located at positions corresponding to nodes associated with resonant ultrasonic vibrations communicated through flexible acoustic waveguide (166). Narrowed section (164) is configured to allow flexible acoustic waveguide (166) to flex without significantly affecting the ability of flexible acoustic waveguide (166) to transmit ultrasonic vibrations. By way of example only, narrowed section (164) may be configured in accordance with one or more teachings of U.S. patent application Ser. No. 13/538,588, now U.S. Pat. No. 9,393,037, issued on Jul. 19, 2016 and/or U.S. patent application Ser. No. 13/657,553, now U.S. Pat. No. 9,095,367, issued Aug. 4, 2015 the disclosures of which are incorporated by reference herein. It should be understood that either waveguide (166, 180) may be configured to amplify mechanical vibrations transmitted through waveguide (166, 180). Furthermore, either waveguide (166, 180) may include features operable to control the gain of the longitudinal vibrations along waveguide (166, 180) and/or features to tune waveguide (166, 180) to the resonant frequency of the system.

In the present example, the distal end of blade (160) is located at a position corresponding to an anti-node associated with resonant ultrasonic vibrations communicated through flexible acoustic waveguide (166), in order to tune the acoustic assembly to a preferred resonant frequency $f_o$ when the acoustic assembly is not loaded by tissue. When transducer assembly (12) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguides (180, 166) to reach blade (160), thereby providing oscillation of blade (160) at the resonant ultrasonic frequency. Thus, when tissue is secured between blade (160) and clamp pad (46), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (44) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

B. Exemplary Shaft Assembly and Articulation Section

FIGS. 2-7 show articulation section (130), which is located at the distal end of shaft assembly (30), with end effector (40) being located distal to articulation section (130). Shaft assembly (30) of the present example extends distally from handle assembly (20). Shaft assembly (30) includes an outer sheath (32) that encloses drive features and the above-described acoustic transmission features. As shown in FIG. 1, a knob (31) is secured to the proximal portion of outer sheath (32). Knob (31) is rotatable relative to body (22), such that shaft assembly (30) is rotatable about the longitudinal axis defined by sheath (32), relative to handle assembly (20). Such rotation may provide rotation of end effector (40), articulation section (130), and shaft assembly (30) unitarily. Of course, rotatable features may simply be omitted if desired.

Articulation section (130) is operable to selectively position end effector (40) at various lateral deflection angles relative to the longitudinal axis defined by sheath (32). Articulation section (130) may take a variety of forms. By way of example only, articulation section (130) may be configured in accordance with one or more teachings of U.S. Pub. No. 2012/0078247, now U.S. Pat. No. 9,402,682, issued Aug. 2, 2016, the disclosure of which is incorporated by reference herein. As another merely illustrative example, articulation section (130) may be configured in accordance with one or more teachings of U.S. patent application Ser. No. 13/538,588, now U.S. Pat. No. 9,393,037, issued on Jul. 19, 2016, and/or U.S. patent application Ser. No. 13/657,553, now U.S. Pat. No. 9,095,367, issued on Aug. 4, 2015, the disclosures of which are incorporated by reference herein. Various other suitable forms that articulation section (130) may take will be apparent to those of ordinary skill in the art in view of the teachings herein.

Figure 6A:
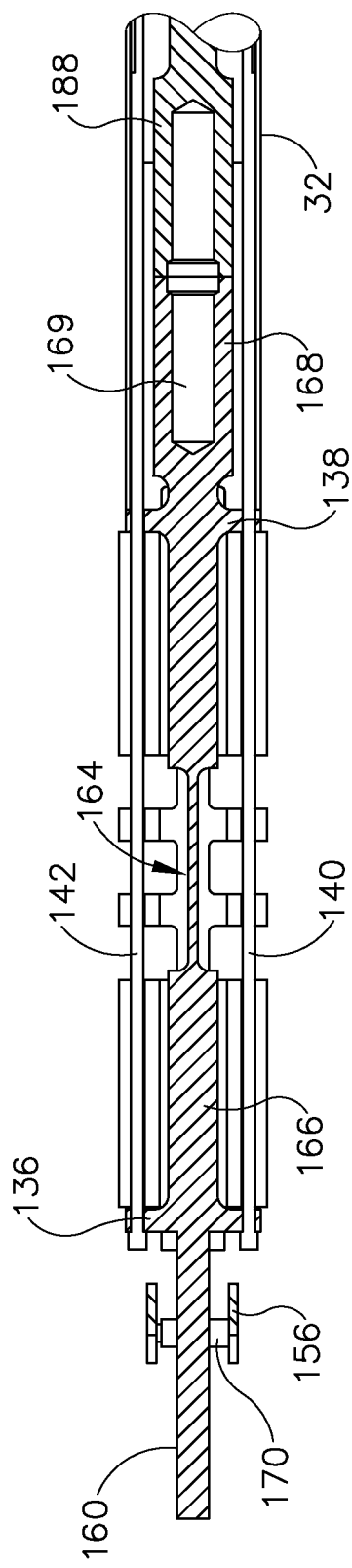
FIG. 6A depicts a cross-sectional view of the components of FIG. 5, taken along line 6-6 of FIG. 4, in a straight configuration.
Figure 6B:
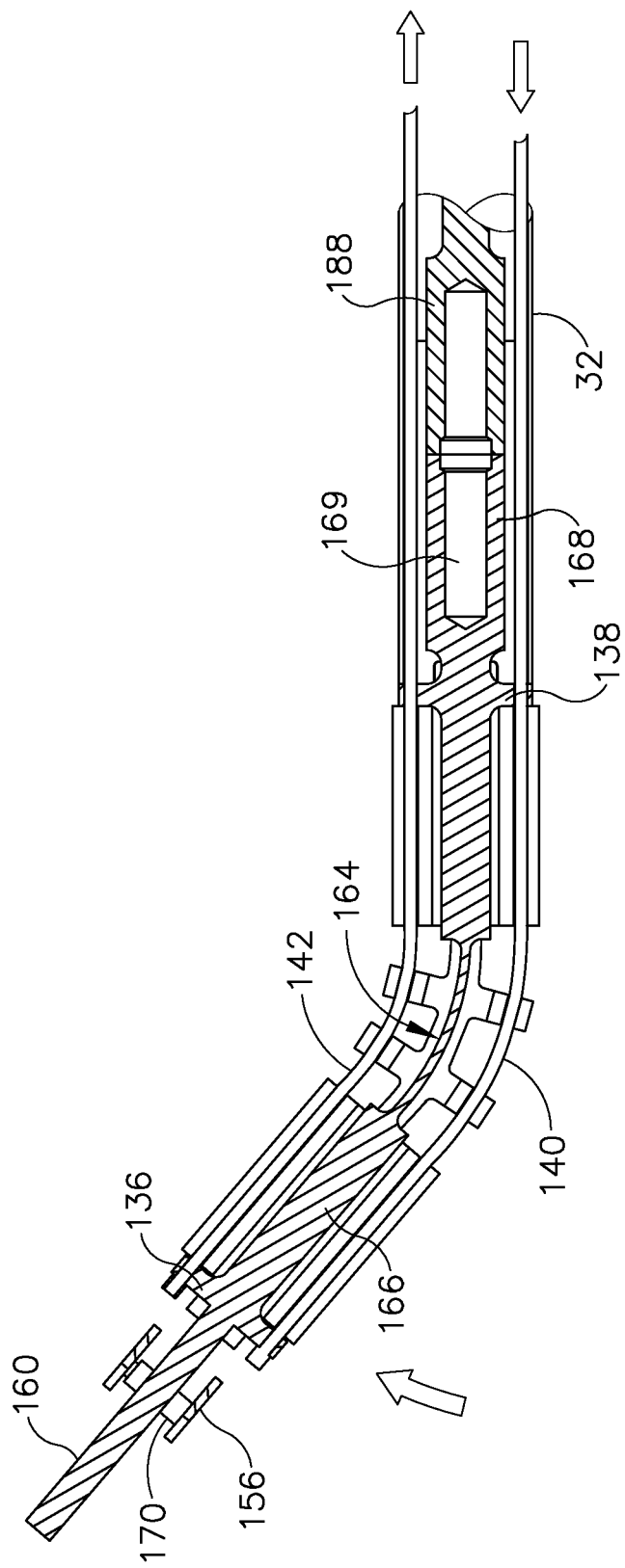
FIG. 6B depicts a cross-sectional view of the components of FIG. 5, taken along line 6-6 of FIG. 4, in a bent configuration.
Figure 7:
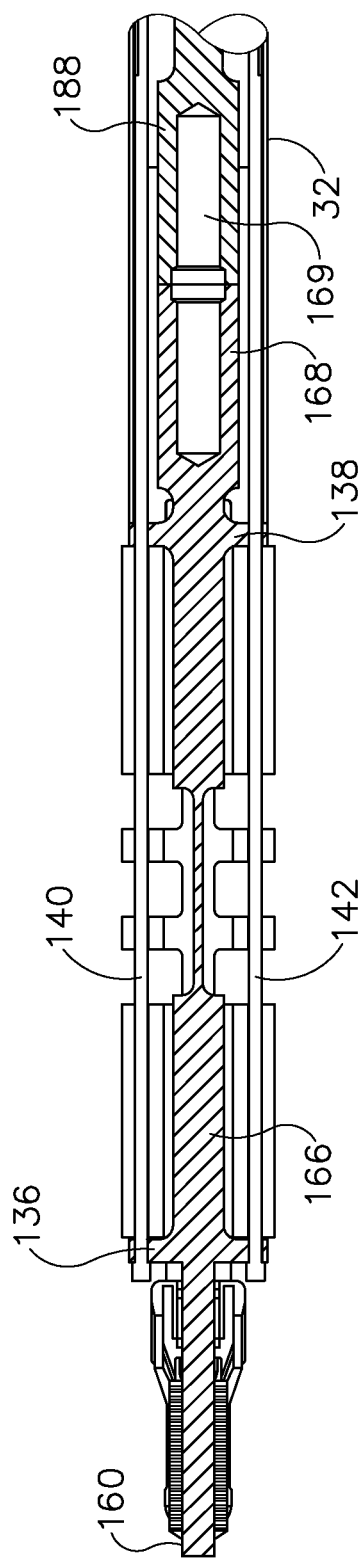
FIG. 7 depicts another cross-sectional view of the components of FIG. 5, taken along line 7-7 of FIG. 4.

As best seen in FIGS. 2-4 articulation section (130) of the present example comprises a first ribbed body portion (132) and a second ribbed body portion (134), with a pair of articulation cables (140, 142) extending through channels defined at the interfaces between ribbed body portions (132, 134). Ribbed body portions (132, 134) are substantially longitudinally positioned between flanges (136, 138) of flexible acoustic waveguide (166). The distal ends of articulation cables (140, 142) are unitarily secured to distal flange (136). Articulation cables (140, 142) also pass through proximal flange (138), yet articulation cables (140, 142) are slidable relative to proximal flange (138). As one articulation cable (140, 142) is pulled proximally, this will cause articulation section (130) to bend, thereby laterally deflecting end effector (40) away from the longitudinal axis of shaft assembly (30) at an articulation angle as shown in FIGS. 6A-6B. In particular, end effector (40) will be articulated toward the articulation cable (140, 142) that is being pulled proximally. During such articulation, the other articulation cable (140, 142) will be pulled distally by flange (136). Ribbed body portions (132, 134) and narrowed section (164) are all sufficiently flexible to accommodate the above-described articulation of end effector (40). Furthermore, flexible acoustic waveguide (166) is configured to effectively communicate ultrasonic vibrations from rigid acoustic waveguide (180) to blade (160) even when articulation section (130) is in an articulated state as shown in FIG. 6B.

II. Exemplary Articulation Drive Mechanisms

As noted above, articulation section (130) may be driven to articulate by driving one or both of articulation cables (140, 142) longitudinally. By way of example only, one articulation cable (140, 142) may be actively driven distally while the other articulation cable (140, 142) is passively permitted to retract proximally. As another merely illustrative example, one articulation cable (140, 142) may be actively driven proximally while the other articulation cable (140, 142) is passively permitted to advance distally. As yet another merely illustrative example, one articulation cable (140, 142) may be actively driven distally while the other articulation cable (140, 142) is actively driven proximally. The following examples include various features that may be used to drive one or both of articulation cables (140, 142) longitudinally, to thereby articulate articulation section (130). It should be understood that the features described below may be readily incorporated into instrument (10) in numerous ways. Other suitable features that may be used to drive one or both of articulation cables (140, 142) longitudinally will be apparent to those of ordinary skill in the art in view of the teachings herein.

A. Exemplary Articulation Drive Mechanism with Rack and Dual Pinions

FIGS. 8-10B show an exemplary mechanism (200) for driving longitudinal movement of articulation cables (140, 142). Mechanism (200) may be partially or completely positioned within handle assembly (20). Mechanism (200) of this example comprises a pair of gears (210, 220) rotatably disposed on opposite ends of an axle (202). In some versions, axle (202) is rotatably supported by body (22). In some other versions, axle (202) is rotatably supported by rigid acoustic waveguide (180). For instance, axle (202) may be located at a position along the length of waveguide (180) corresponding to a node associated with resonant ultrasonic vibrations communicated through waveguide (180). Regardless of where or how axle (202) is supported, gears (210, 220) are operable to rotate about an axis defined by axle (202).

Figure 8:
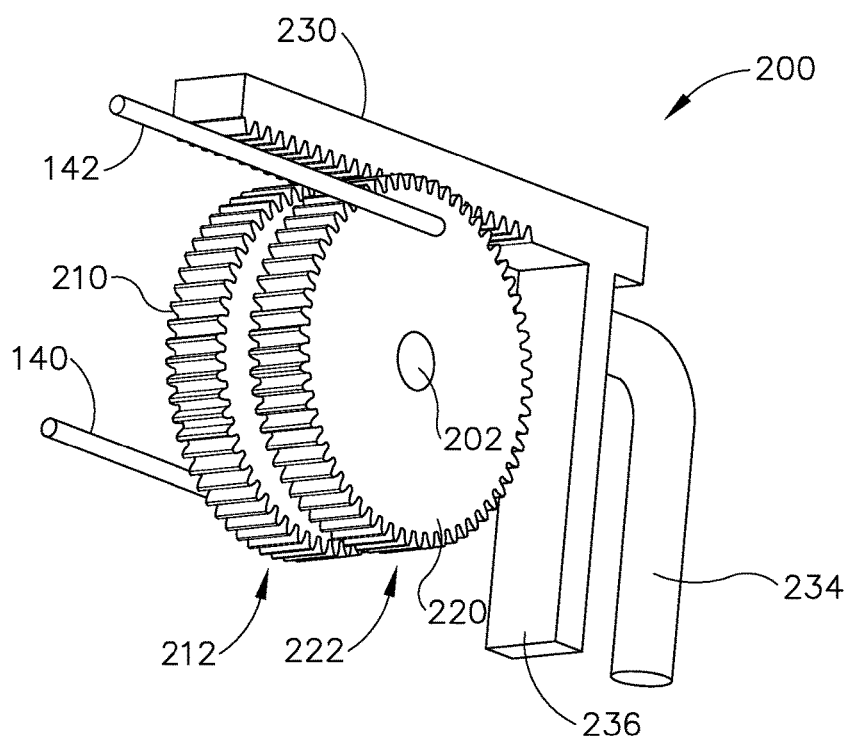
FIG. 8 depicts a perspective view of an exemplary mechanism for driving articulation of the shaft assembly of FIG. 2.
Figure 9:
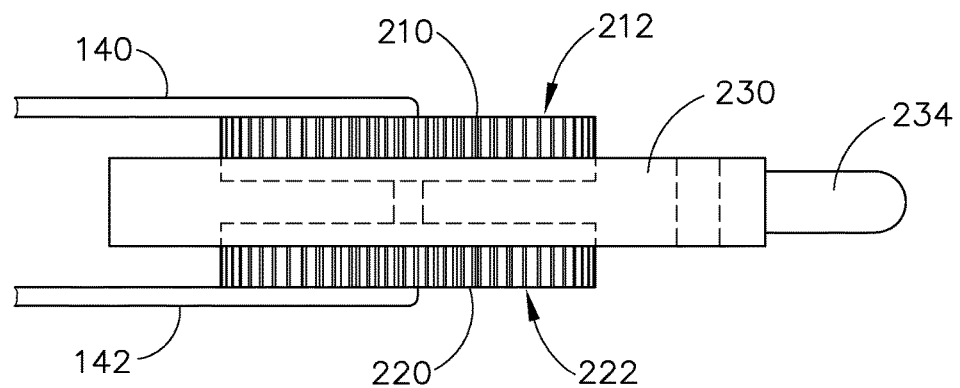
FIG. 9 depicts a side elevational view of the mechanism of FIG. 8.
Figure 10A:
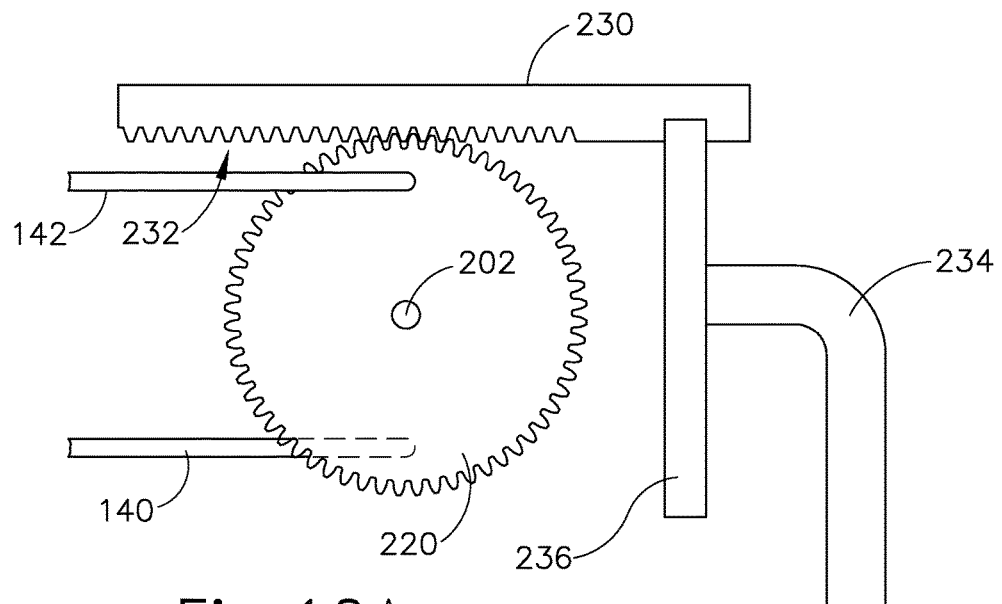
FIG. 10A depicts a top plan view of the mechanism of FIG. 8, with a drive gear in a first rotational position.
Figure 10B:
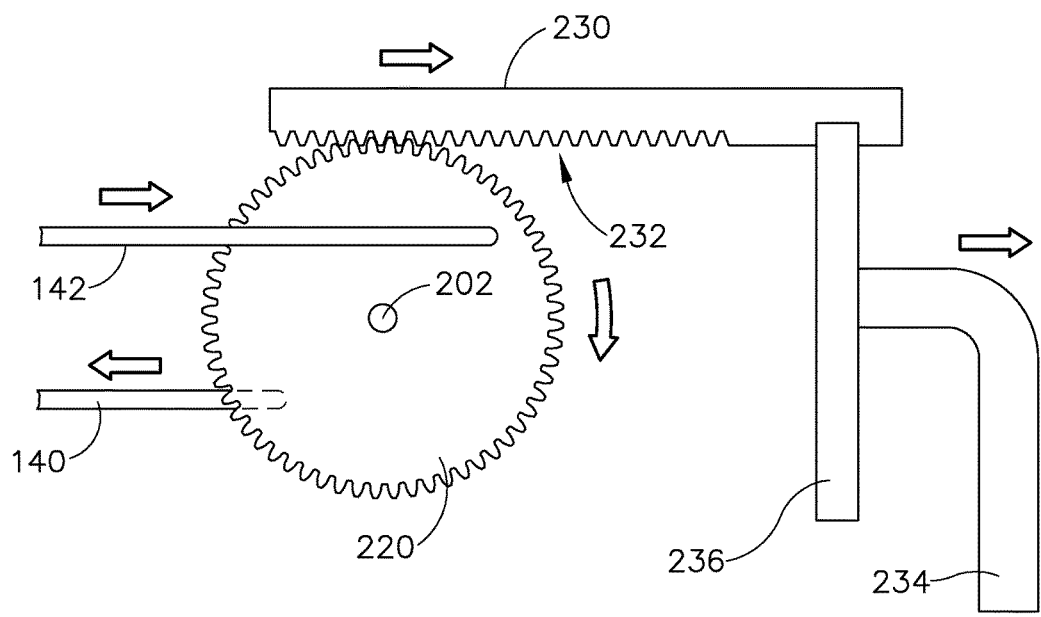
FIG. 10B depicts a top plan view of the mechanism of FIG. 8, with the drive gear in a second rotational position.

Each gear (210, 220) includes a plurality of teeth (212, 222) disposed about an exterior circumference of each gear (210, 220). As best seen in FIG. 8, a proximal end of articulation cable (140) is coupled to an exterior surface of gear (210) and a proximal end of articulation cable (142) is coupled to an exterior surface of gear (220). As best seen in FIGS. 10A-10B, the fixation points of the proximal ends of cables (140, 142) are radially offset from the longitudinal axis of axle (202). As also seen in FIGS. 10A-10B, the fixation points of the proximal ends of cables (140, 142) are angularly offset relative to each other. In the present example, the angular offset is approximately 180°, though it should be understood that any other suitable angular offset may be used. It should also be understood that the proximal ends of cables (140, 142) may be pivotally coupled with respective gears (210, 220). For instance, such a pivotal coupling may permit articulation cables (140, 142) to maintain a substantially parallel relationship with each other in the region near gears (210, 220) as gears (210, 220) are rotated, without creating a tendency for cables (140, 142) to bind or wind upon themselves.

Mechanism (200) of the present example further comprises a rack member (230). Rack member (230) comprises a plurality of teeth (232). Teeth (232) of rack member (230) are configured to concurrently engage teeth (212, 222) of gears (210, 220). In some versions, a single set of teeth (232) simultaneously engages both sets of teeth (212, 222). In some other versions, rack member (230) has two separate sets of teeth—one set to engage teeth (212) and another set to engage teeth (222). Rack member (230) is coupled with a trigger (234) via a coupling (236), such that trigger (234) is operable to move rack member (230) longitudinally. In some instances, trigger (234) protrudes from or is otherwise exposed relative to body (22). As will be discussed in more detail below, longitudinal movement of rack member (230) causes concurrent rotation of gears (210, 220) to thereby cause opposing longitudinal movement of articulation cables (140, 142), thus deflecting articulation section (130).

In some versions, coupling (236) comprises a slip washer. By way of example only, rack member (230) may orbitally rotate about the outer perimeter of coupling (236). In some such versions, axle (202) is secured to waveguide (180), such that axle (202), gears (210, 220), rack member (230), waveguide (180), and the remainder of shaft assembly (30) and end effector (40) all rotate about the longitudinal axis of waveguide (180) while trigger (234) remains rotationally stationary. As another merely illustrative example, coupling (236) may be rotatably coupled with trigger (234), such that coupling (236) rotates with axle (202), gears (210, 220), rack member (230), waveguide (180), and the remainder of shaft assembly (30) and end effector (40) about the longitudinal axis of waveguide (180) while trigger (234) remains rotationally stationary. In versions where axle (202) is supported by waveguide (180), it should be understood that coupling (236) may include an opening configured to accommodate waveguide (180); and that trigger (234) may also be configured to avoid direct contact with waveguide (180).

FIG. 10A shows mechanism (200) in a first position. In this first position, rack member (230) is in a first longitudinal position and gears (210, 220) are in a first rotational position. When mechanism (200) is in the first position, articulation section (130) is in a straight configuration (FIG. 6A). A user may actuate trigger (234) to thereby drive rack member (230) into a second longitudinal position as shown in FIG.

10B. Longitudinal movement of rack member (230) will cause concurrent rotation of gears (210, 220). Because articulation cables (140, 142) are coupled to angularly opposed regions of the exterior surface of gears (210, 220), concurrent rotation of gears (210, 220) drives articulation cables (140, 142) in opposite longitudinal directions. For instance, as shown in FIG. 10B, clockwise rotation of gears (210, 220) will cause proximal longitudinal movement of articulation cable (142) and distal longitudinal movement of articulation cable (140). Alternatively, counter-clockwise rotation of gears (210, 220) will cause distal longitudinal movement of articulation cable (142) and proximal longitudinal movement of articulation cable (140).

It should be understood that articulation cables (140, 142) may be positioned at different radial distances from axle (202) to thereby increase/decrease the amount of longitudinal movement that rotation of gears (210, 220) will cause to each cable (140, 142). Furthermore, although articulation cables (140, 142) are positioned a similar radial distance from axle (202) in the present example, articulation cables (140, 142) may be positioned at different radial distances to thereby increase/decrease the amount of longitudinal movement that rotation of gears (210, 220) will cause to each cable (140, 142) independently.

Figure 11:
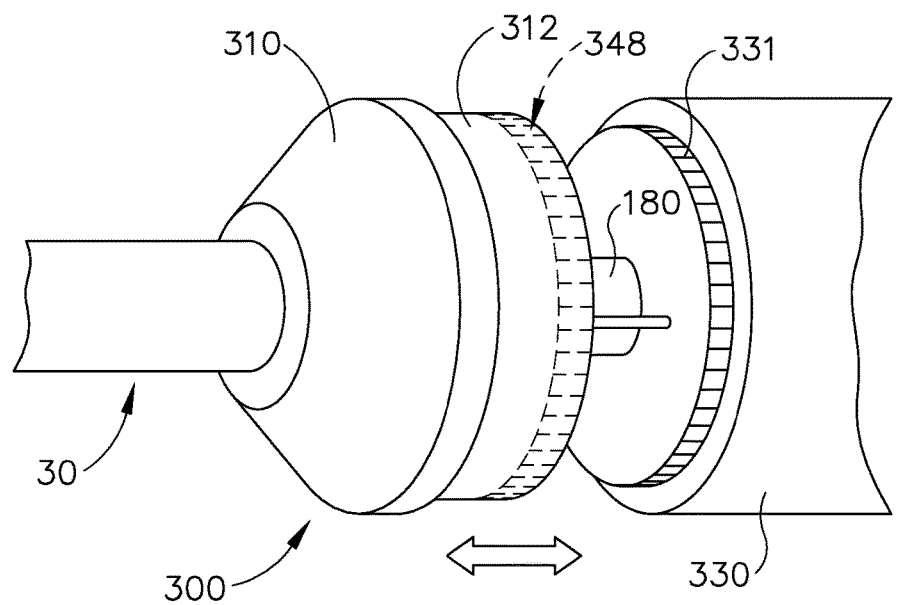
FIG. 11 depicts a perspective view of an exemplary alternative mechanism for driving articulation of the shaft assembly of FIG. 2.
Figure 12A:
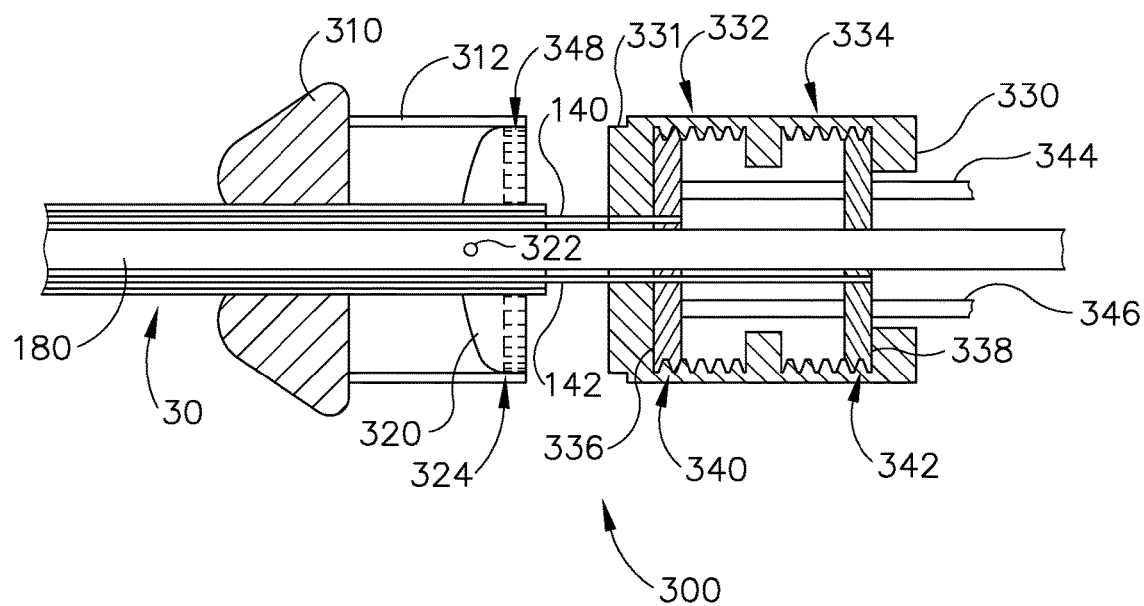
FIG. 12A depicts a cross-sectional view of the mechanism of FIG. 11, with a rotation knob in a first longitudinal position and disengaged from an articulation driver.
Figure 12B:
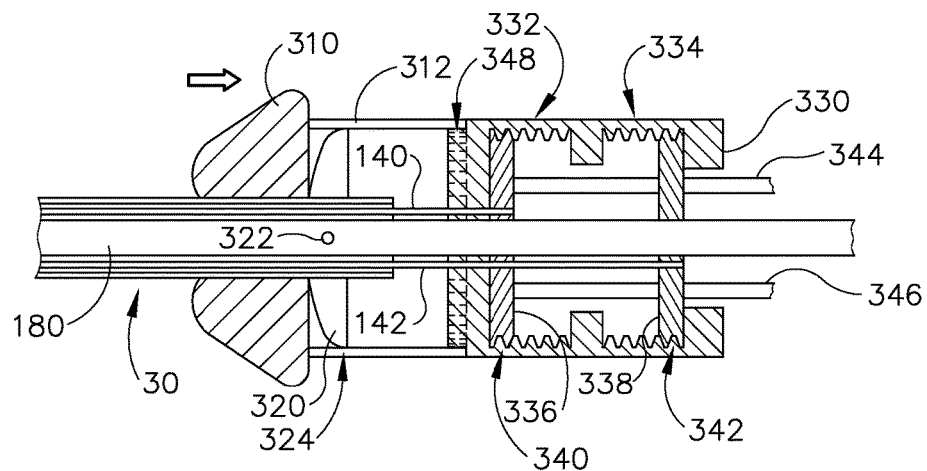
FIG. 12B depicts a cross-sectional view of the mechanism of FIG. 11, with the rotation knob in a second longitudinal position and engaged with the articulation driver in a first rotational position.
Figure 12C:
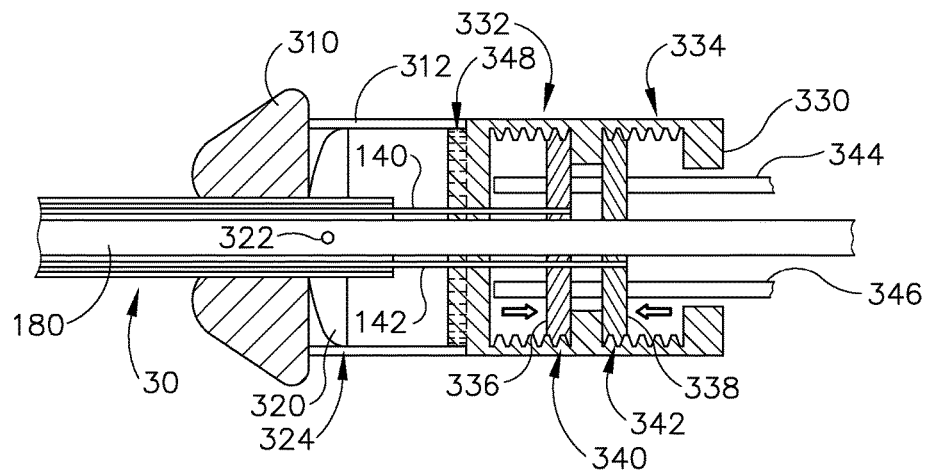
FIG. 12C depicts a cross-sectional view of the mechanism of FIG. 11, with the rotation knob in the second longitudinal position and engaged with the articulation driver in a second rotational position.

B. Exemplary Articulation Drive Mechanism with Clutching Driver and Opposing Lead Screws FIGS. 11-12C show an exemplary alternative mechanism (300) for driving longitudinal movement of articulation cables (140, 142). Mechanism (300) may be partially or completely positioned within handle assembly (20). Mechanism (300) of this example comprises a rotation knob (310), a shaft assembly rotation driver (320), and an articulation drive nut (330). In the present example, rotation knob (310) is a variation of knob (31) described above. Rotation knob (310) includes an integral, proximally extending sleeve (312). Sleeve (312) presents an array of longitudinally oriented, inwardly extending splines (348). Rotation knob (310) is configured to slide longitudinally to selectively engage splines (348) with either rotation driver (320) or articulation drive nut (330). In particular, and as will be described in greater detail below, rotation knob (310) is engaged with rotation driver (320) when rotation knob (310) is in a distal position; and rotation knob (310) is engaged with articulation drive nut (330) when rotation knob (310) is in a proximal position. In the distal position, rotation knob (310) is operable to rotate rotation driver (320) to thereby rotate shaft assembly (30) and end effector (40). In the proximal position, rotation knob (310) is operable to rotate articulation drive nut (330) to thereby articulate articulation section (130). It should be understood that a detent feature, over-center feature, and/or some other kind of feature may be operable to selectively maintain rotation knob (310) in either the distal position or the proximal position.

Rotation driver (320) is operable to rotate shaft assembly (30) and end effector (40), relative to handle assembly (20), about the longitudinal axis defined by shaft assembly (30). In particular, rotation driver (320) is secured to waveguide (180) by a pin (322), which is located at a position along the length of waveguide (180) corresponding to a node associated with resonant ultrasonic vibrations communicated through waveguide (180). Waveguide (180) thus rotates concomitantly with rotation driver (320). The remainder of shaft assembly (30) will also rotate with rotation driver (320). The exterior of the proximal region (324) of rotation driver (322) includes a set of longitudinally oriented splines (not shown) extending radially outwardly from rotation driver (322). These splines mesh with complementary inwardly extending splines (348) in sleeve (312) of rotation knob (310) when rotation knob (310) is in a distal position as shown in FIG. 12A. This engagement between splines (348) of sleeve (312) and the splines of rotation driver (320) provides rotation of rotation driver (322) (and its associated components) in response to rotation of rotation knob (310). When rotation knob (310) is in a proximal position as shown in FIGS. 12B-12C, splines (348) of sleeve (312) are disengaged from the splines of rotation driver (320), such that rotation of rotation knob (310) will not rotate rotation driver (322) or its associated components. It should be understood that one or more features may selectively lock the rotational position of rotation driver (322) and/or its associated components when rotation knob (310) is shifted to the proximal position shown in FIG. 12B-12C.

As best seen in FIG. 11, the exterior of a distal portion of articulation drive nut (330) includes a set of longitudinally oriented splines (331) extending radially outwardly from drive nut (330). These splines (331) are configured to mesh with splines (348) of sleeve (312) of rotation knob (310) when rotation knob (310) is in a proximal position as shown in FIGS. 12B-12C. This engagement between splines (348) of sleeve (312) and splines (331) of articulation drive nut (330) provides rotation of articulation drive nut (330) in response to rotation of rotation knob (310). When rotation knob (310) is in a distal position as shown in FIG. 12A splines (348) of sleeve (312) are disengaged from splines (331) of articulation drive nut (330), such that rotation of rotation knob (310) will not articulation drive nut (330). As best seen in FIGS. 12A-12C, the interior of articulation drive nut (330) defines a first internal thread region (332) and a second internal thread region (334). In the present example, first internal thread region (332) and second internal thread region (334) comprise opposing threading (i.e., oriented at opposing pitches). For instance, first internal thread region (332) may have a right-handed thread pitch while second internal thread region (334) has a left-handed thread pitch, or vice-versa.

A first lead screw (336) is disposed within first internal thread region (332) while second lead screw (338) is disposed in second internal thread region (334). First lead screw (336) presents a first external thread (340) that complements the threading of first internal thread region (332) of articulation drive nut (330). Second lead screw (338) presents a second external thread (342) that complements the threading of second internal thread region (334) of articulation drive nut (330). Pins (344, 346) are slidably disposed within first lead screw (336) and second lead screw (338). Pins (344, 346) are mounted within handle assembly (20) such that pins (344, 346) are unable to rotate. Thus, as articulation drive nut (330) rotates, pins (344, 346) prevent first lead screw (336) and second lead screw (338) from rotating but allow first lead screw (336) and second lead screw (338) to translate longitudinally. As noted above, first internal thread region (332) and second internal thread region (334) have opposing thread pitches, such that rotation of articulation drive nut (330) in a single direction causes opposing translation of lead screws (336, 338) within articulation drive nut (330). Thus rotation of articulation drive nut (330) will cause translation of first lead screw (336) in a first longitudinal direction within first internal thread region (332) of articulation drive nut (330) and simultaneous translation of second lead screw (338) in a second longitudinal direction within second internal thread region (334) of articulation drive nut (330), as shown in FIG. 12C.

As shown in FIGS. 12A-12C, articulation cable (140) is coupled with first lead screw (336) such that articulation cable (140) translates unitarily with first lead screw (336). Articulation cable (142) is coupled with second lead screw (338) such that articulation cable (142) translates unitarily with second lead screw (338). It should therefore be understood that articulation cables (140, 142) will translate in an opposing fashion in response to rotation of articulation drive nut (330), thus causing articulation of articulation section (130). Rotating drive nut (330) in one rotational direction will cause articulation of articulation section (130) in a first direction of articulation; while rotating drive nut (330) in another rotational direction will cause articulation of articulation section (130) in an opposite direction of articulation. It should be understood from the foregoing that the articulation driving features of mechanism (300) may be configured and operable in accordance with at least some of the teachings of U.S. Pub. No. 2013/0023868, entitled "Surgical Instrument with Contained Dual Helix Actuator Assembly," published Jan. 24, 2013, now U.S. Pat. No. 9,545,253, issued on Jan. 17, 2017, the disclosure of which is incorporated by reference herein.

Figure 13A:
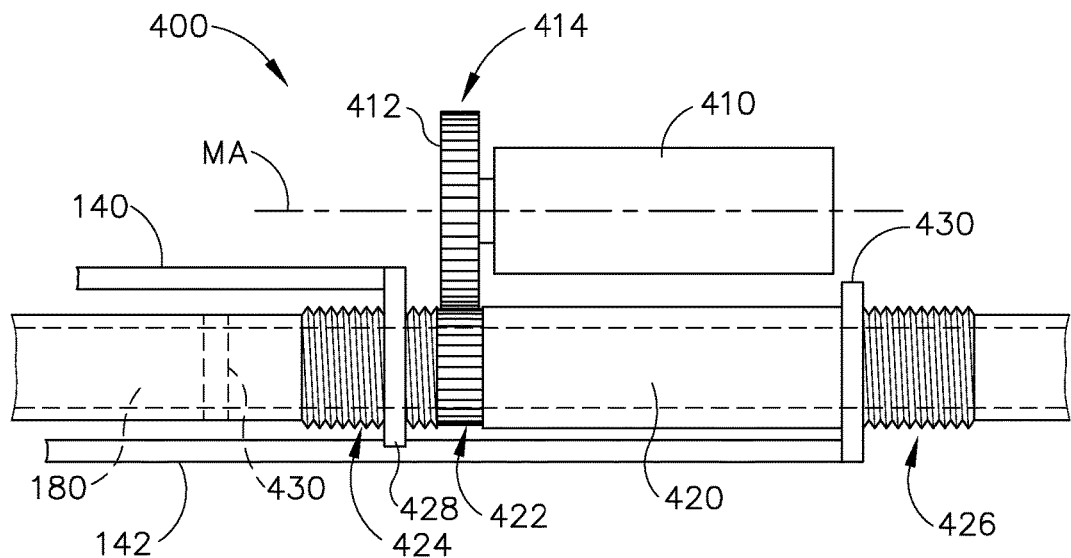
FIG. 13A depicts a side elevational view of another exemplary alternative mechanism for driving articulation of the shaft assembly of FIG. 2, in a first operational state.
Figure 13B:
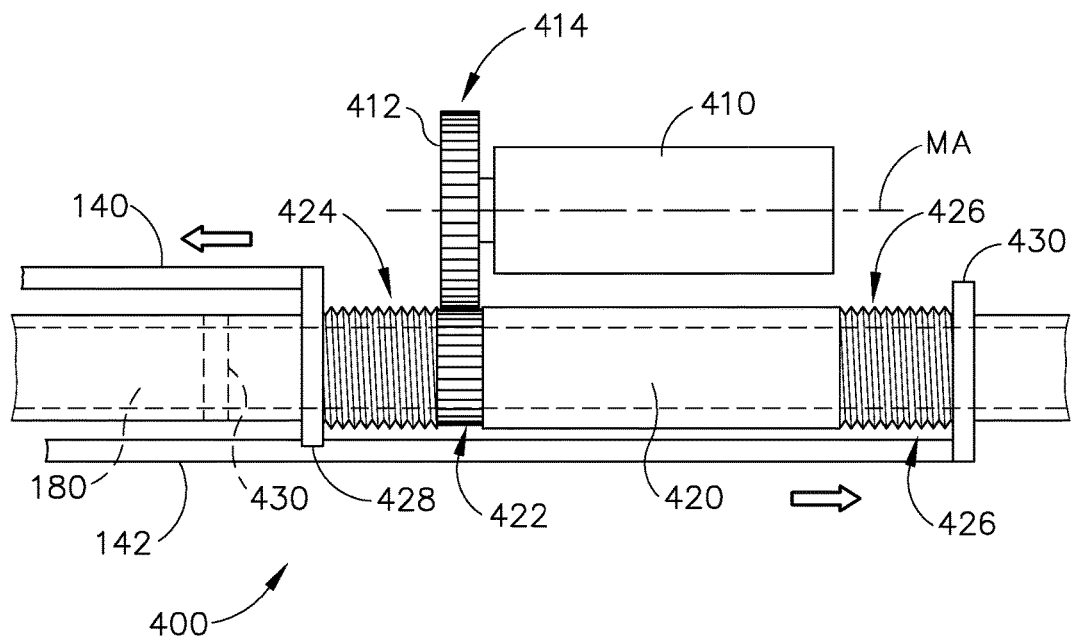
FIG. 13B depicts a side elevational view of the mechanism of FIG. 13A, in a second operational state.

C. Exemplary Articulation Drive Mechanism with Offset Motor and Opposing Lead Screws FIGS. 13A-13B show another exemplary alternative mechanism (400) for driving longitudinal movement of articulation cables (140, 142). Mechanism (400) may be partially or completely positioned within handle assembly (20). Mechanism (400) of this example comprises a motor (410), a drive shaft (420), and a pair of drive nuts (428, 430). Motor (410) is oriented along a motor axis (MA) that is parallel to yet laterally offset from the longitudinal axis of waveguide (180). Motor (410) is mechanically coupled with a gear (412) such that motor (410) is operable to rotate gear (412). Gear (412) comprises a plurality of teeth (414) disposed about an exterior circumference of gear (412). Drive shaft (420) is coaxially disposed about waveguide (180). One or more setoff members (430) are coaxially interposed between waveguide (180) and drive shaft (420). Setoff member (430) is located at a position along the length of waveguide (180) corresponding to a node associated with resonant ultrasonic vibrations communicated through waveguide (180). Setoff member (430) is configured to support drive shaft (430) while allowing drive shaft to rotate relative to waveguide (180). Various suitable forms that setoff member (430) may take will be apparent to those of ordinary skill in the art in view of the teachings herein.

A central region of drive shaft (420) comprises a plurality of teeth (422) disposed about an exterior circumference of drive shaft (420). Teeth (414) of gear (412) engage teeth (422) of drive shaft (420) such that rotation of gear (412) causes rotation of drive shaft (420) about the longitudinal axis of waveguide (180). A distal region of drive shaft (420) comprises a first external threading (424) while a proximal region of drive shaft (420) comprises a second external threading (426). First and second external threading (424, 426) have opposing pitch (i.e., opposing thread orientation). For instance, first external threading (424) may have a right-handed thread pitch while second external threading (426) has a left-handed thread pitch, or vice-versa.

A first drive nut (428) is disposed over first external threading (424). First drive nut (428) has a first internal threading that complements first external threading (424). A second drive nut (430) is disposed over second external threading (426). Second drive nut (424) has a second internal threading that complements second external threading (426). Drive nuts (428, 430) are secured within handle assembly (20) such that drive nuts (428, 430) may translate within handle assembly (20) but not rotate within handle assembly (20). Thus, when drive shaft (420) rotates within handle assembly (20), drive nuts (428, 430) will translate in opposing longitudinal direction due to the configurations of threading (424, 426). For instance, in the transition between FIG. 13A and FIG. 13B, drive shaft (420) has rotated such that first drive nut (428) has translated distally while second drive nut (430) has simultaneously translated proximally. Various suitable ways in which drive nuts (428, 430) may be secured within handle assembly (20) will be apparent to those of ordinary skill in the art in view of the teachings herein.

Figure 14:
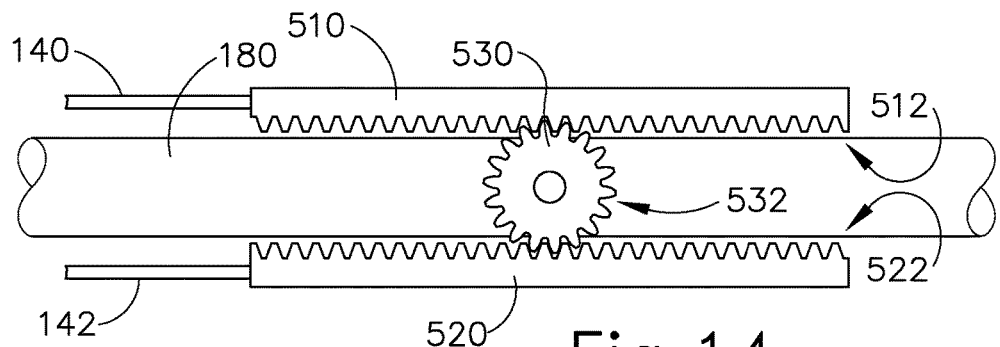
FIG. 14 depicts a top view of yet another exemplary alternative mechanism for driving articulation of the shaft assembly of FIG. 2.
Figure 15A:
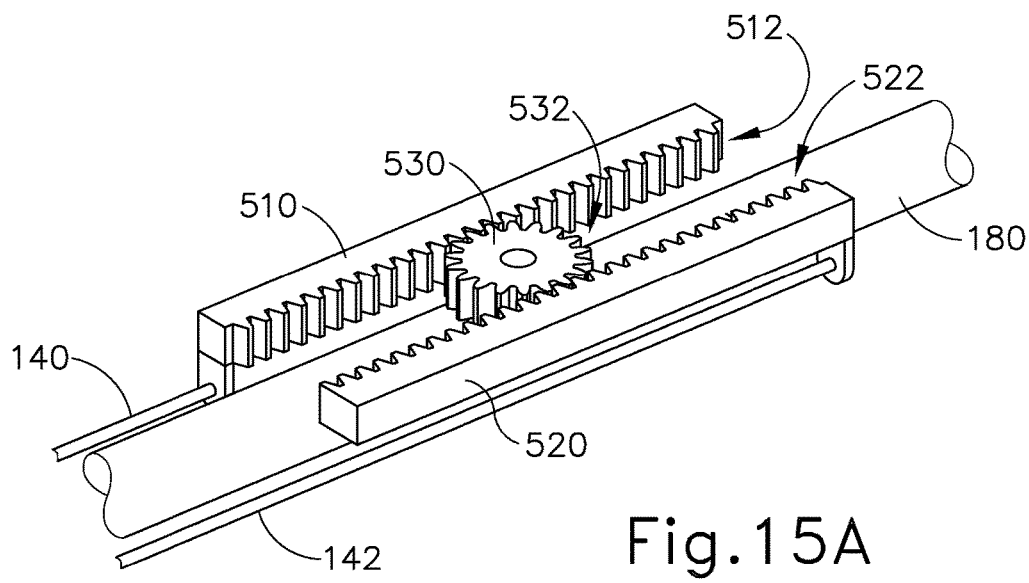
FIG. 15A depicts a perspective view of the mechanism of FIG. 14, with a pair of gear racks in a first longitudinal position.
Figure 15B:
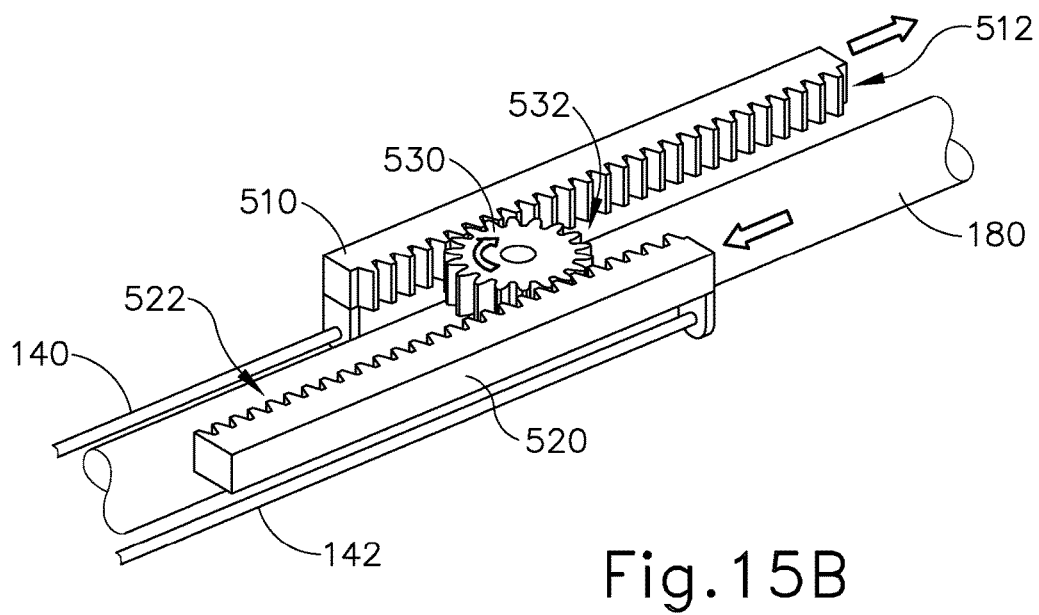
FIG. 15B depicts a perspective view of the mechanism of FIG. 14, with the pair of gear racks in a second longitudinal position.

As also shown in FIGS. 13A-13B, articulation cable (140) is coupled with first drive nut (428) such that articulation cable (140) translates unitarily with first drive nut (428). Articulation cable (142) is coupled with second drive nut (430) such that articulation cable (142) translates unitarily with second drive nut (430). It should therefore be understood that articulation cables (140, 142) will translate in an opposing fashion in response to rotation of drive shaft (420), thus causing articulation of articulation section (130). It should be understood that rotating drive shaft (420) in one rotational direction will cause articulation of articulation section (130) in a first direction of articulation; while rotating drive shaft (420) in another rotational direction will cause articulation of articulation section (130) in an opposite direction of articulation D. Exemplary Articulation Drive Mechanism with Pinion and Opposing Racks FIGS. 14-15B show another exemplary alternative mechanism (500) for driving longitudinal movement of articulation cables (140, 142). Mechanism (500) may be partially or completely positioned within handle assembly (20). Mechanism (500) of this example comprises a pair of rack members (510, 520) and a pinion gear (530). Rack members (510, 520) are slidably disposed in body (22). Rack members (510, 520) each comprises a plurality of teeth (512, 522) disposed along an interior surface of rack members (510, 520). Pinion gear (530) comprises a plurality of teeth (532) disposed about an exterior circumference of gear (430). Rack member (510) is oriented such that teeth (512) of rack member (510) engage teeth (532) of pinion gear (530), such that rotation of pinion gear (530) causes longitudinal translation of rack member (510). Similarly, rack member (520) is oriented such that teeth (522) of rack member (520) engage teeth (532) of pinion gear (530), such that rotation of pinion gear (530) causes longitudinal translation of rack member (520). In some versions, pinion gear (530) is rotated by a motor. In some other versions, pinion gear (530) is driven manually (e.g., by a dial, lever, knob, etc.). Various suitable ways in which pinion gear (530) may be driven will be apparent to those of ordinary skill in the art in view of the teachings herein.

As best seen in FIG. 14, teeth (512) of rack member (510) and teeth (522) of rack member (520) engage teeth (532) of pinion gear (530) on opposite sides of pinion gear (530). Thus, it should be understood that rotation of pinion gear (530) in a single direction will cause longitudinal translation of rack members (510, 520) in opposite directions simultaneously. For instance, clockwise rotation of pinion gear (530) will cause proximal longitudinal translation of rack member (510) and simultaneous distal longitudinal translation of rack member (520) as shown in FIG. 15B. Alternatively, counter-clockwise rotation of pinion gear (530) will cause distal longitudinal translation of rack member (510) and simultaneous proximal longitudinal translation of rack member (520). As shown in FIGS. 15A-15B, articulation cable (140) is coupled with rack member (510). Articulation cable (142) is coupled with second rack member (520). It should therefore be understood that articulation cables (140, 142) will translate distally and/or proximally, in opposing fashion, in response to rotation of pinion gear (530), thereby causing articulation of articulation section (130).

In some versions, articulation cable (140) is coupled with rack member (510) via a washer, bushing, or other rotatable feature that is rotatably disposed about waveguide (180). Similarly, articulation cable (142) may be coupled with rack member (520) via a washer, bushing, or other rotatable feature that is rotatably disposed about waveguide (180). In some such versions, rack members (510, 520) do not rotate within body (22), yet cables (140, 142) may orbitally rotate about the longitudinal axis of waveguide (180) (e.g., as shaft assembly (30) and end effector (40) are also rotated), while still maintaining a connection with rack members (510, 520). Other suitable ways in which rotation of shaft assembly (30) and end effector (40) may be accommodated will be apparent to those of ordinary skill in the art in view of the teachings herein.

E. Exemplary Articulation Drive Mechanism with Lever and Pawl

Figure 16A:
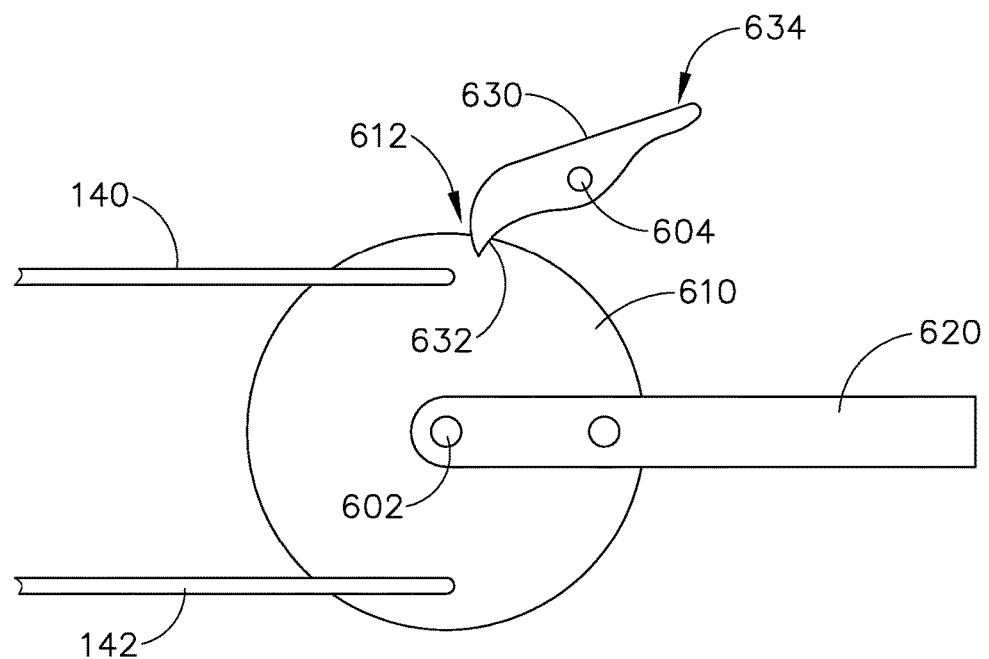
FIG. 16A depicts a top view of yet another exemplary alternative mechanism for driving articulation of the shaft assembly of FIG. 2, with a drive gear in a first rotational position.
Figure 16B:
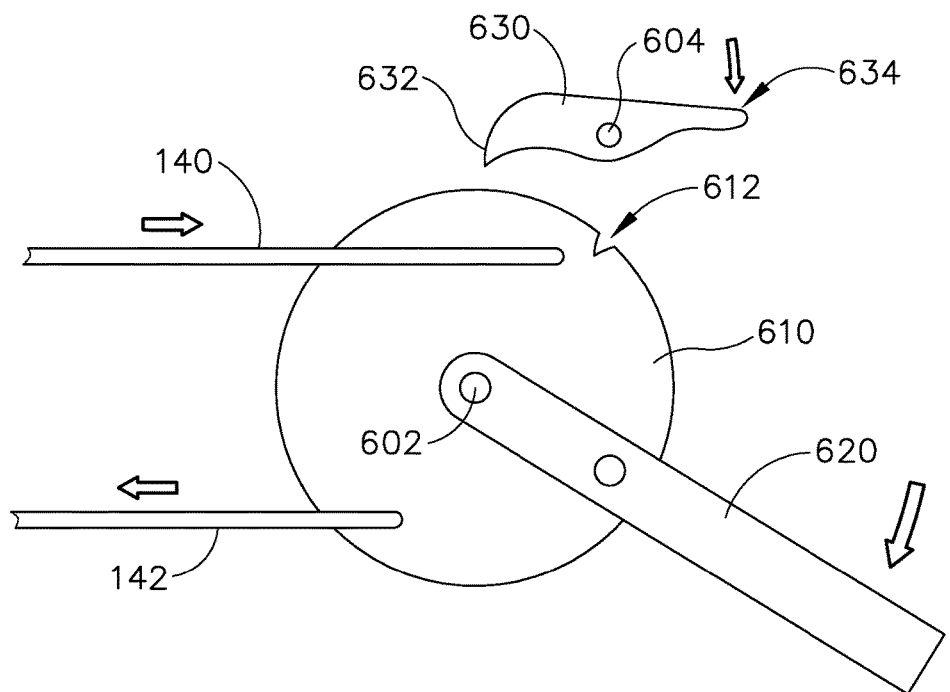
FIG. 16B depicts a top plan view of the mechanism of FIG. 16A, with the drive gear in a second rotational position.

FIGS. 16A-16B show another exemplary alternative mechanism (600) for driving longitudinal movement of articulation cables (140, 142). Mechanism (600) may be at least partially positioned within handle assembly (20). Mechanism (600) of this example comprises a rotating member (610), a lever (620), and a locking member (630). Rotating member (610) and lever (620) are rotatably disposed about an axle (602). Lever (620) is fixedly coupled to rotating member (610) such that rotation of lever (620) about axle (602) causes rotation of rotating member (610) about axle (602). In some versions, at least a portion of lever (620) is exposed relative to body (22) (e.g., near pistol grip (24)), enabling an operator to contact and drive lever (620) with the operator's finger or thumb. As shown in FIG. 16A, a proximal end of articulation cable (140) is pivotally coupled to an upper portion of rotating member (610); and a proximal end of articulation cable (142) is pivotally coupled to a lower portion of rotating member (610). The pivotal nature of these couplings permits articulation cables (140, 142) to maintain a substantially parallel relationship with each other as rotating member (610) is rotated, without articulation cables (140, 142) binding or wrapping, etc.

Locking member (630) is pivotable about a pin (604). An exterior circumference of rotating member (610) presents a recess (612). As shown in FIG. 16A, locking member (630) presents a tooth (632) configured to engage recess (612) to thereby prevent rotating member (610) from rotating about axle (602). As shown in FIG. 16B, to disengage locking member (630) from recess (612), a user may apply pressure to a thumb paddle (634) of locking member (630) to thereby rotate locking member (630) about pin (604), thus removing tooth (632) from recess (612). In some versions, at least a portion of thumb paddle (634) may be exposed relative to body (22) to enable direct manipulation by a user's thumb or finger. Locking member (630) may be resiliently biased toward the locking position shown in FIG. 16A. For instance, a torsion spring (not shown) may rotate locking member (630) toward the locking position. In the present example, recess (612) is located at a position corresponding to articulation section (130) being in a non-articulated state. It should be understood that recess (612) may be located elsewhere and/or that other recesses (612) may be included. For instance, a plurality of recesses (612) may be used to provide selective locking of articulation section (130) in various states of articulation. Other suitable ways in which articulation section (130) may be selectively locked will be apparent to those of ordinary skill in the art in view of the teachings herein.

FIG. 16A shows mechanism (600) in a first position. In this first position, rotating member (610) and lever (620) are in a first rotational position. It should be understood that with mechanism (600) in the first position, articulation section (130) is in a straight configuration (FIG. 6A). The operator may depress thumb paddle (634) to unlock rotating member (610); and actuate lever (620) to thereby drive rotating member (610) into a second rotational position as shown in FIG. 16B. Because articulation cables (140, 142) are coupled to opposite portions of rotating member (610), rotation of rotating member (610) drives articulation cables (140, 142) in opposite longitudinal directions. For instance, as shown in FIG. 16B, clockwise rotation of rotating member (610) will cause proximal longitudinal movement of articulation cable (140) and distal longitudinal movement of articulation cable (142). This drives articulation section (130) to an articulated state, as shown in FIG. 6B.

It should be understood that articulation cables (140, 142) may be positioned at different radial distances from axle (602) to thereby increase/decrease the amount of longitudinal movement that rotation of rotating member (610) will cause to each cable (140, 142). Furthermore, although in the present example articulation cables (140, 142) are positioned a similar radial distance from axle (602), articulation cables (140, 142) may be positioned at different radial distances to thereby increase/decrease the amount of longitudinal movement that rotation of rotating member (610) will cause to each cable (140, 142) independently. In some alternative versions, cables (140, 142) are consolidated into a single cable that wraps around a proximal portion of the outer perimeter of rotating member (610) similar to a pulley wheel arrangement. As yet another merely illustrative variation, cables (140, 142) may be coupled with the free ends of a flexible drive member that wraps about a proximal portion of the outer perimeter of rotating member (610). Such a flexible drive member may include outwardly extending teeth that selectively engage tooth (632) in a ratcheting fashion, such that the flexible drive member and locking member (630) cooperate to selectively maintain the longitudinal positioning of cables (140, 142). Other suitable configurations and arrangements will be apparent to those of ordinary skill in the art in view of the teachings herein.

III. Exemplary Articulation with Single Translating Driver

Figure 17A:
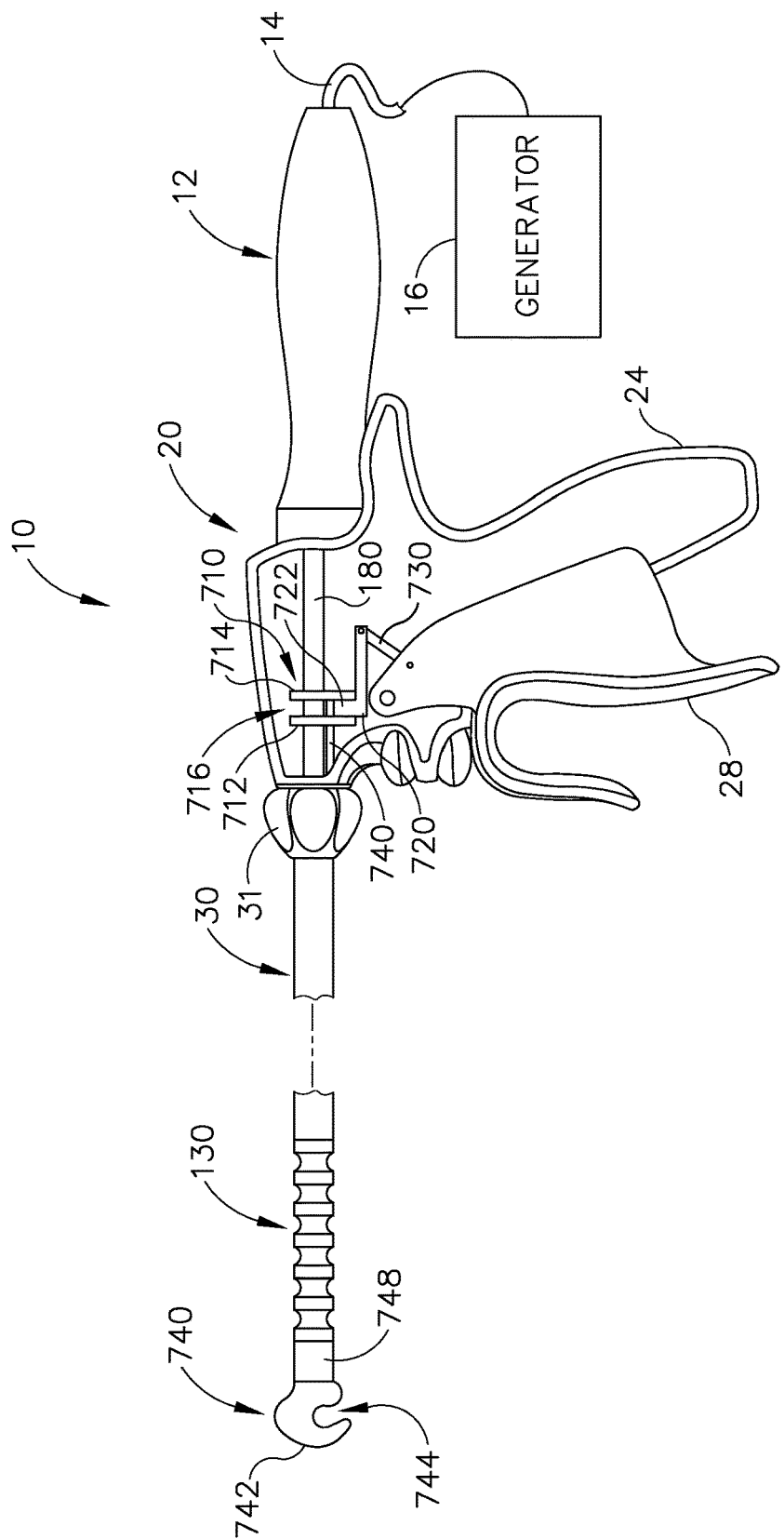
FIG. 17A depicts a side elevational view of yet another exemplary alternative mechanism for driving articulation of the shaft assembly of FIG. 2, with a drive arm in a first longitudinal position.
Figure 17B:
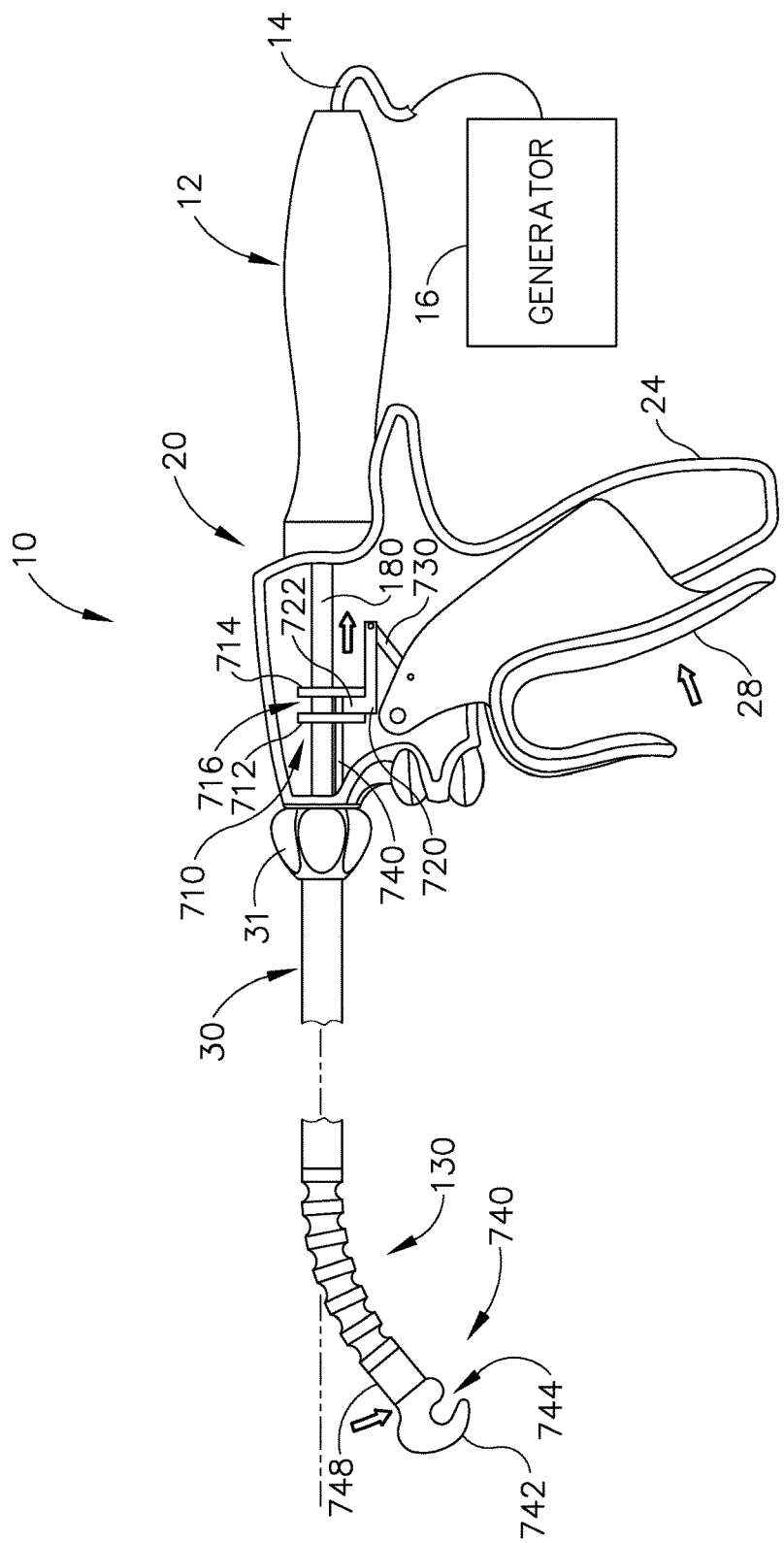
FIG. 17B depicts a side elevational view of the mechanism of FIG. 17A, with the drive arm in a second longitudinal position.

The examples described above include a pair of translating drivers—articulation cables (140, 142)—to drive articulation of articulation section (130). It should be understood that it is also possible to use just a single translating driver to drive articulation of articulation section (130). For instance, a single translating driver may be retracted proximally from a home position to articulate articulation section (130) in a single direction; then be returned distally to the home position to return articulation section (130) to a substantially straight configuration. FIGS. 17A-17B show an exemplary configuration for driving articulation of articulation section (130) using a single translating driver. In particular, FIGS. 17A-17B show a version of instrument (10) having a single articulation drive band (740). The proximal end of articulation drive band (740) is secured to a coupler (710). The distal end of articulation drive band (740) is secured to a distal collar (748) of articulation section (130). Coupler (710) is coaxially and slidably disposed about waveguide (180). Coupler (710) comprises a distal flange (712) and a proximal flange (714), which together define a channel (716) therebetween. Coupler (710) is configured to rotate with band (740), shaft assembly (30), and end effector (740) in response to rotation of knob (31).

Body (20) includes a link (730) in this example. One end of link (730) is pivotally coupled with trigger (28), while the other end of link (730) is pivotally coupled with a translating driver (720). Link (730) is configured to pivot and translate within body (20), while driver (720) is configured to only translate (without rotating) in body (20). The distal end of driver (720) includes a yoke (722), which is positioned in channel (716) of coupler (710). The engagement between yoke (722) and coupler (710) provides longitudinal translation of coupler (710) (and, hence, band (740)) in response to longitudinal translation of driver (720). However, the engagement between yoke (722) and coupler (710) also permits coupler (710) to rotate within yoke (722). It should be understood that link (730) converts pivotal motion of trigger (28) toward and away from grip (24) into longitudinal motion of driver (720), coupler (710), and band (740). Such motion is depicted in the series of FIGS. 17A-17B, in which driver (720), coupler (710), and band (740) translate proximally in response to trigger (28) being pivoted toward grip (24). As can also be seen in FIGS. 17A-17B, the proximal movement of band (740) causes articulation section (130) to articulate away from the longitudinal axis of shaft assembly (30), thereby positioning end effector (740) at an articulated position. When trigger (28) is driven away from grip (24) to the position shown in FIG. 17A, articulation section (130) and end effector (740) also return to a position where articulation section (130) and end effector (740) are aligned with the longitudinal axis of shaft assembly (30). In some instances, trigger (28) and/or other features are resiliently biased to assume the configuration shown in FIG. 17A, such that the operator need only relax their grip on trigger (28) to return from the configuration shown in FIG. 17B to the configuration shown in FIG. 17A.

End effector (740) of the present example comprises a hook-shaped ultrasonic blade (742). Blade (742) is angularly oriented such that articulation section (130) bends along an angular path that is substantially parallel the gap (744) defined by the hook-shaped configuration. Of course, any other suitable kind of end effector may be used; and the geometry of the end effector may have any other suitable relationship with the operation of articulation section (130). While articulation section (130) deflects end effector (740) away from the longitudinal axis of shaft assembly (30) in only one direction in the present example, it should be understood that the rotatability of shaft assembly (30) and end effector (740) may nevertheless provide selective positioning of blade (742) at various orientations. For instance, an operator may manipulate knob (31) to first achieve a desired angular orientation; then manipulate trigger (28) to articulate blade (742) at a desired angle of articulation. Alternatively, the operator may first manipulate trigger (28) to articulate blade (742) at a desired angle of articulation; then manipulate knob (31) to achieve a desired angular orientation. Other suitable methods of operation will be apparent to those of ordinary skill in the art in view of the teachings herein. It should also be understood that another articulation band may be provided for articulation along another path. Such an additional articulation band may have a corresponding coupler, yoke, and trigger, etc.

IV. Exemplary Alternative Articulation Section Configurations

The foregoing examples of articulation drive mechanisms have all been discussed in the context of articulation section (130). It should be understood that articulation section (130) is just one merely illustrative example, and that the various articulation drive mechanism teachings above may be readily applied to various other kinds of articulation sections. Several examples of alternative articulation sections will be described in greater detail below. Still further examples of alternative articulation sections will be apparent to those of ordinary skill in the art in view of the teachings herein. Similarly, various suitable ways in which the articulation drive mechanisms described herein may be incorporated with the various alternative articulation sections described herein will be apparent to those of ordinary skill in the art.

A. Exemplary Articulation Section with Curved Bias

Figure 18A:
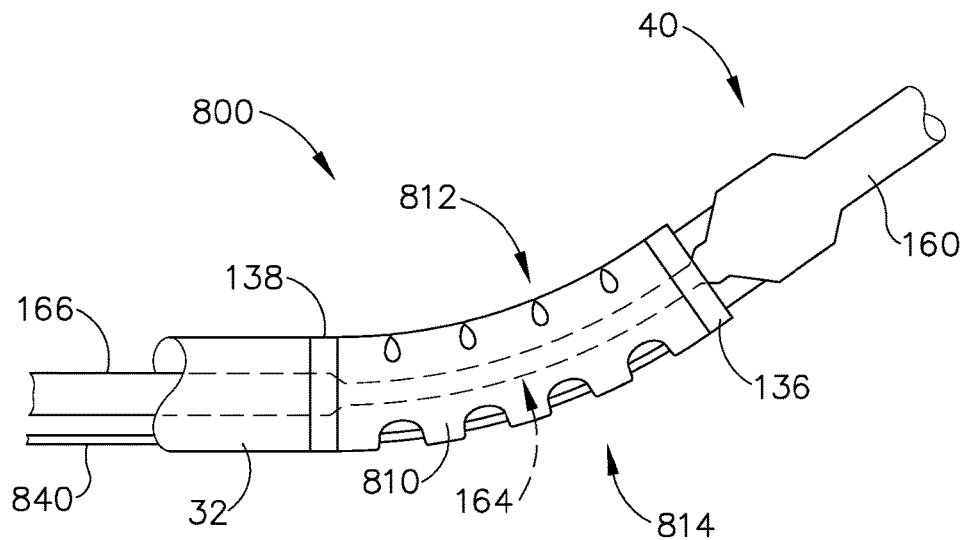
FIG. 18A depicts a top plan view of an exemplary alternative articulation section in a bent configuration.
Figure 18B:
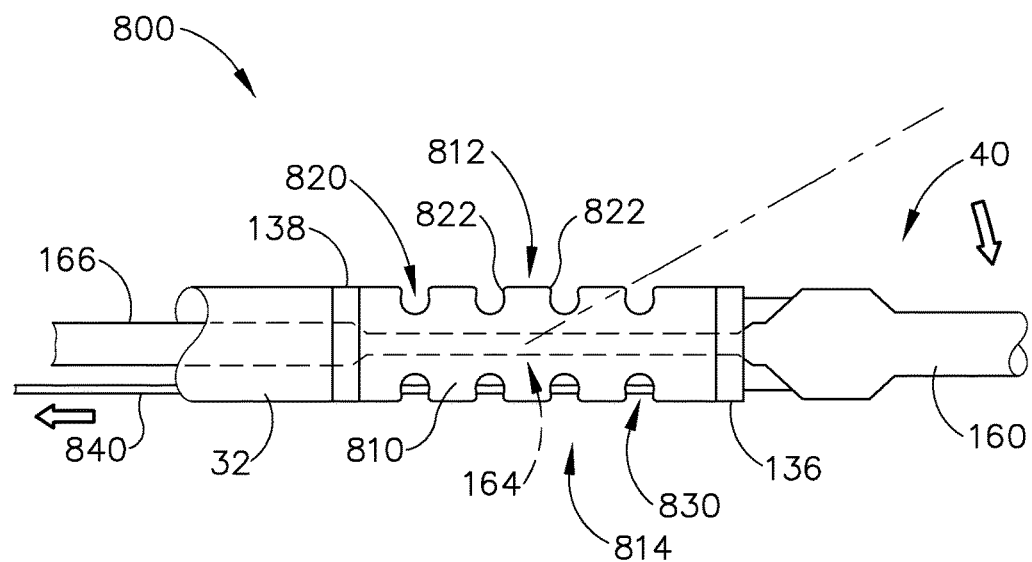
FIG. 18B depicts a top plan view of the articulation section of FIG. 18A in a straight configuration.

FIGS. 18A-18B show an exemplary alternative articulation section (800) that may be interposed between shaft assembly (30) and end effector (40) in place of articulation section (130), to selectively position end effector (40) at various lateral deflection angles relative to the longitudinal axis defined by shaft assembly (30). Articulation section (800) of the present example comprises a ribbed body (810), with a single articulation band (840) extending through a channel defined within ribbed body (810). Ribbed body (810) comprises a first plurality of ribs (812) and a second plurality of ribs (814) disposed on opposite sides of ribbed body (810). Ribs (812) define a plurality of gaps (820). Ribs (814) also define a plurality of gaps (830). Gaps (820, 830) are configured to promote bending of ribbed body (810).

As shown in FIG. 18A, ribbed body (810) is configured to have an initial bent configuration thus defining a first side of ribbed body (810) which follows a circumference having a first radius and a second side of ribbed body (810) which follows a circumference having a second (smaller) radius. Ribbed body (810) is preformed to resiliently assume the bent configuration shown in FIG. 18A. Each gap (820) includes a pair of boss surfaces (822) that engage each other when ribbed body (810) is in the bent configuration shown in FIG. 18A. This engagement between boss surfaces (822) provides a hard stop that restricts the bend angle of articulation section (800).

Ribs (812) are disposed on the side of ribbed body (810) that follows a circumference having the second, smaller radius when articulation section (800) is in the bent configuration. Ribs (814) are disposed on the side of ribbed body (810) that follows a circumference having the first, larger radius when articulation section (800) is in the bent configuration. Ribbed body (810) is longitudinally positioned between flanges (136, 138) of flexible acoustic waveguide (166). The distal end of articulation cable (140) is unitarily secured to distal flange (136). Articulation cable (140) also passes through ribs (814) proximal flange (138), yet articulation cable (140) is slidable relative to ribs (814) and proximal flange (138). In addition to (or as an alternative to) ribbed body (810) being preformed to resiliently assume the bent state shown in FIG. 18A, flexible waveguide (166) may be preformed to resiliently assume the bent state shown in FIG. 18A.

As articulation band (840) is pulled proximally, this will cause articulation section (800) to bend away from the state shown in FIG. 18A, thereby deflecting end effector (40) toward the longitudinal axis of shaft assembly (30) as shown in FIG. 18B. In particular, end effector (40) will be articulated toward articulation cable (140) until articulation section (800) reaches a substantially straight configuration. To re-bend articulation section (800), articulation band (840) may simply be released, such that the resilient bias of ribbed body (810) and/or the resilient bias of flexible waveguide (166) resiliently returns articulation section (800) to the bent state shown in FIG. 18A. In addition or in the alternative, articulation band (840) may be driven distally to assist in the re-bending of articulation section (800) to the position shown in FIG. 18A. Ribbed body (810) and narrowed section (164) are all sufficiently flexible to accommodate the above-described bending and straightening of articulation section (800). To the extent that an operator wishes to selectively lock articulation section (800) at some partially bent state (e.g., between the position shown in FIG. 18A and the position shown in FIG. 18B), one or more locking features may be manipulated to selectively lock articulation section (800) at such a partially bent state. Various suitable examples of locking features that may be used for this purpose will be apparent to those of ordinary skill in the art in view of the teachings herein.

B. Exemplary Articulation Section with Articulation Bands

Figure 19:
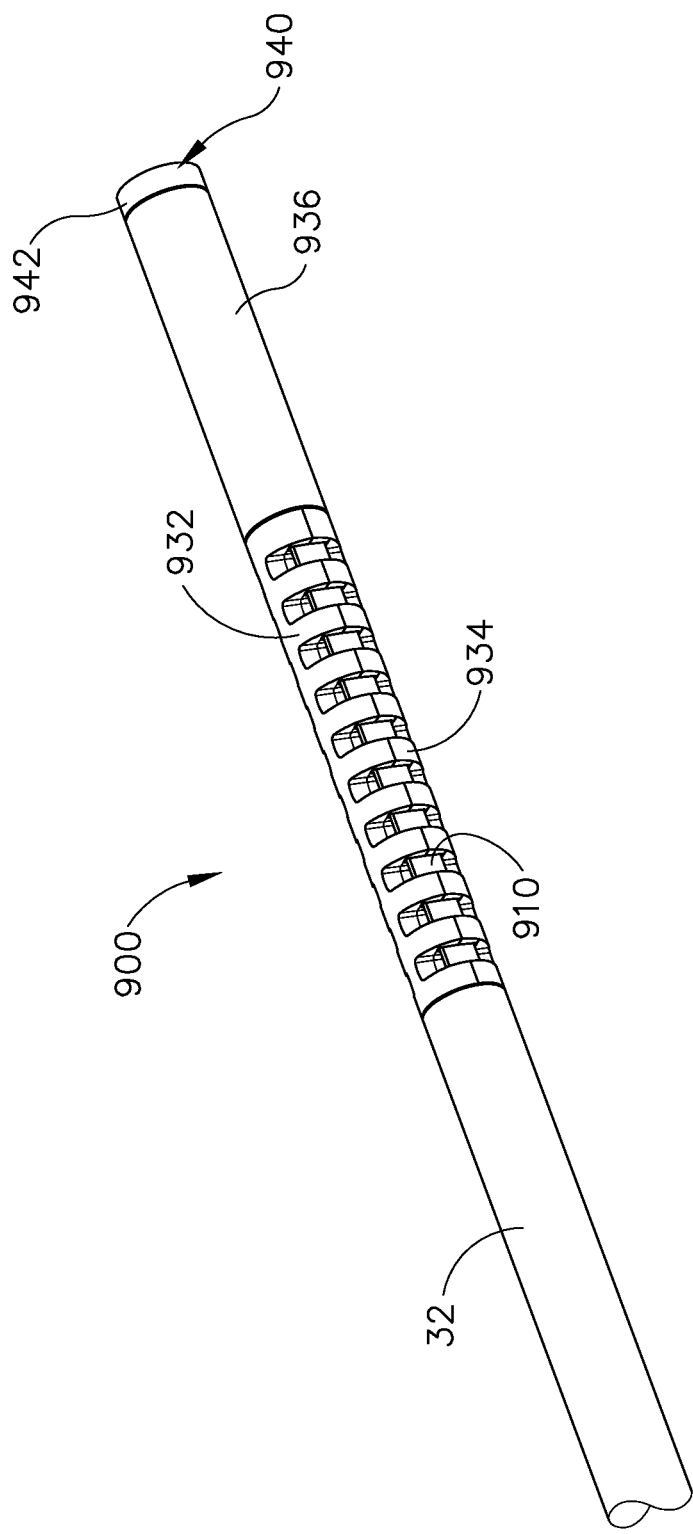
FIG. 19 depicts a perspective view of another exemplary articulation section.
Figure 20A:
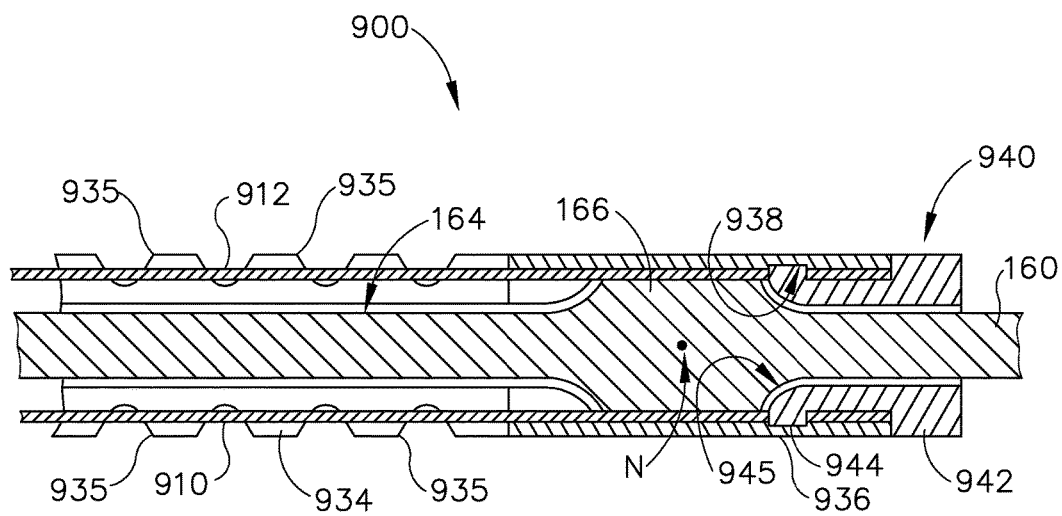
FIG. 20A depicts a cross-sectional side view of the articulation section of FIG. 19 in a straight configuration.
Figure 20B:
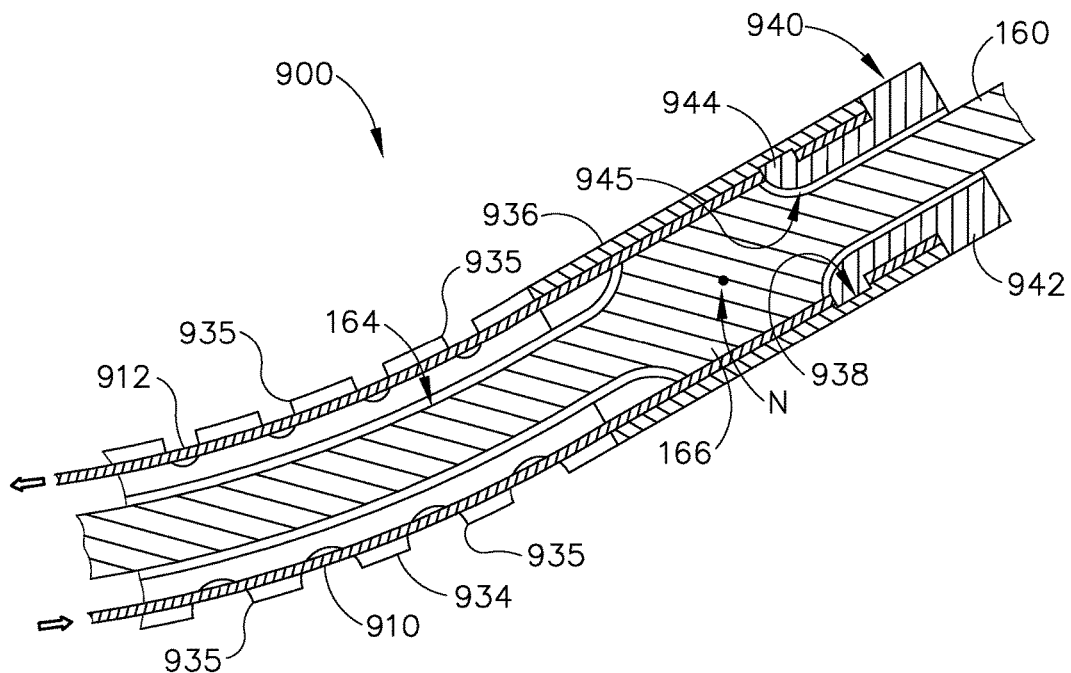
FIG. 20B depicts a cross-sectional side view of the articulation section of FIG. 19 in a bent configuration.

FIGS. 19-20B show another exemplary alternative articulation section (900) that may be interposed between shaft assembly (30) and end effector (40) in place of articulation section (130), to selectively position end effector (40) at various lateral deflection angles relative to the longitudinal axis defined by shaft assembly (30). Articulation section (900) of this example comprises a first ribbed body portion (932) and a second ribbed body portion (934), with pair of articulation bands (910, 912) extending through channels defined at the interfaces between ribbed body portions (932, 934). In some versions, waveguide (166) includes flat surfaces on the entire length along which articulation bands (910, 912) extend. In particular, such flat surfaces may be located on laterally opposing sides of waveguide (166). Such flat surfaces may provide accommodation for articulation bands (910, 912), such that the inclusion of articulation bands (910, 912) will not increase the overall outer diameter presented by a combination of articulation bands (910, 912) and waveguide (166). In other words, the inner diameter and outer diameter of outer sheath (32) need not be any larger than such diameters otherwise would be in a non-articulating version of instrument (10). By way of example only, flats may be provided along the length of waveguide (166) in accordance with at least some of the teachings of U.S. patent application Ser. No. 13/868,336, entitled "Ultrasonic Device for Cutting and Coagulating," filed Apr. 23, 2013, now U.S. Patent Pub. No. 2013/0289592, published on Oct. 31, 2013, the disclosure of which is incorporated by reference herein. Alternatively, such flat surfaces may take any other suitable form. As another alternative, such flat surfaces may simply be omitted. To the extent that the present application refers to an articulation band (910, 912) extending "along" a flat lateral region of waveguide (166) it should be understood that this does not mean that the articulation band (910, 912) would need to come into contact with waveguide (166). It simply means that the articulation band (910, 912) would simply reside in a void left by the flat lateral region of waveguide (166) (i.e., a void that would otherwise be occupied by the material forming waveguide (166) if that region of waveguide (166) had a circular cross-section).

Ribbed body portions (932, 934) are longitudinally positioned between outer sheath (32) and an outer tube (936). Ribbed body portions (932, 934) are configured to flex to permit articulation of articulation section (900) in response to opposing translation of articulation bands (910, 912) as shown in the series of FIGS. 20A-20B. Ribbed body portions (932, 934) thus permit sliding of articulation bands (910, 912) within the channels of ribbed body portions (932, 934). By way of example only, ribbed body portions (932, 934) and/or other features of articulation section (900) may be configured in accordance with at least some of the teachings of U.S. Pub. No. 2012/0078247, entitled "Articulation Joint Features for Articulating Surgical Device," published Mar. 29, 2012, now U.S. Pat. No. 9,402,682, issued Aug. 2, 2016, the disclosure of which is incorporated by reference herein.

The distal ends of articulation bands (910, 912) are secured to a distal collar (940). Distal collar (940) includes a distal flange (942) and projections (944) that extend outwardly in an opposing fashion. Projections (944) are disposed in respective openings formed near the distal ends of articulation bands (910, 912) thereby coupling distal collar (940) with articulation bands (910, 912). Distal flange (942) abuts the distal edge of outer tube (936). In the example shown, projections (944) extend into an annular recess (938) formed within outer tube (936), thereby providing a snap-fit coupling between distal collar (940) and outer tube (936). In some other versions, annular recess (938) is omitted. For instance, tension in articulation bands (910, 912) may suffice to substantially secure the position of distal collar (940) relative to outer tube (936). Other suitable configurations and relationships will be apparent to those of ordinary skill in the art in view of the teachings herein.

In the present example, articulation section (900) is configured such that a nodal portion (N) of waveguide (166) is positioned in outer tube (936), just proximal to where articulation bands (910, 912) are coupled with collar (940). Nodal portion (N) corresponds with a distal node associated with resonant ultrasonic vibrations communicated through waveguide (166). When articulation bands (910, 912) are translated longitudinally in an opposing fashion as shown in FIG. 20B, a moment is created and applied to nodal portion (N) through outer tube (936). This causes articulation section (900) and narrowed section (164) of waveguide (166) to articulate, without transferring axial forces in articulation bands (910, 912) to waveguide (166). In particular, articulation section (900) of the present example maintains a gap (945) between the proximal end of distal collar (940) and nodal portion (N) of waveguide (166), such that collar (940) does not bear proximally against a distally facing surface of nodal portion (N), even when articulation section (900) is in a bent state as shown in FIG. 20B. Thus, nodal portion (N) only receives laterally directed bearing forces (by outer tube (936) and/or bands (910, 912)) when being driven to an articulated position as shown in FIG. 20B.

It should be understood that one articulation band (910, 912) may be actively driven distally while the other articulation band (910, 912) is passively permitted to retract proximally. As another merely illustrative example, one articulation band (910, 912) may be actively driven proximally while the other articulation band (910, 912) is passively permitted to advance distally. As yet another merely illustrative example, one articulation band (910, 912) may be actively driven distally while the other articulation band (910, 912) is actively driven proximally. Various suitable ways in which articulation bands (910, 912) may be driven will be apparent to those of ordinary skill in the art in view of the teachings herein.

In the discussion of the examples shown in FIGS. 18A-18B, it was noted how boss surfaces (822) of ribbed body (810) engage each other when ribbed body (810) is bent to the configuration shown in FIG. 18A, such that boss surfaces (822) provide a hard stop that restricts the bend angle of articulation section (800). The same principle may apply to articulation section (900) shown in FIGS. 19-20B. In particular, ribbed body portions (932, 934) of the present example include opposing surfaces (935) that may act as boss surfaces that engage each other on one side of articulation section (900) when articulation section (900) reaches a fully articulated state. Surfaces (935) may thus restrict the bend angle of articulation section (900) (e.g., to prevent narrowed section (164) of waveguide (166) from overbending, etc.). Other suitable ways in which the bend angle of articulation section (900) may be restricted will be apparent to those of ordinary skill in the art in view of the teachings herein.

C. Exemplary Articulation Section with Coaxial Segmented Regions

FIGS. 21-27 show another exemplary alternative articulation section (1000) that may be interposed between shaft assembly (30) and end effector (40) in place of articulation section (130), to selectively position end effector (40) at various lateral deflection angles relative to the longitudinal axis defined by shaft assembly (30). Articulation section (1000) of this example is formed by a segmented region (1012) of an outer tube (1010) and a segmented region (1022) of an inner tube (1020). Tubes (1010, 1020) are coaxially aligned with each other. Outer tube (1010) is rotatable and relative to inner tube (1020). Inner tube (1020) is translatable relative to outer tube (1010). As will be described in greater detail below, such relative rotation of outer tube (1010) and translation of inner tube (1020) may be performed even while articulation section (1000) is in an articulated state.

Figure 21:
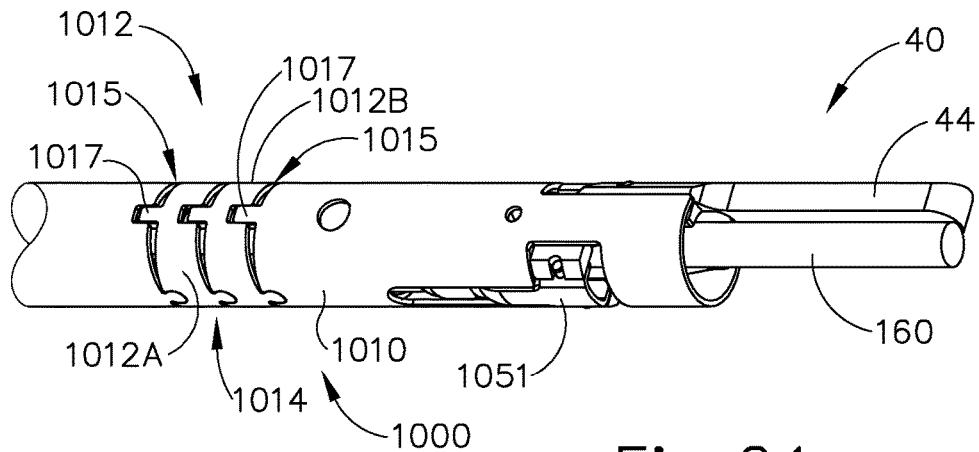
FIG. 21 depicts a perspective view of yet another exemplary articulation section and end effector.
Figure 25:
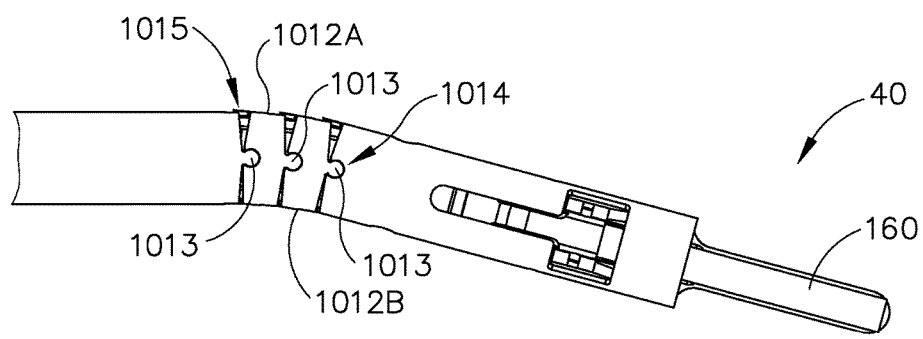
FIG. 25 depicts a top plan view of the articulation section and end effector of FIG. 21, with the articulation section in a bent configuration.

Segmented region (1012) of outer tube (1010) comprises a plurality of segments (1012A, 1012B). Segments (1012A, 1012B) are joined to each other and to the remainder of outer tube (1010) by coupling features (1013), which are best seen in FIG. 25. Coupling features (1013) are in the form of rounded tabs that fit in complementary recesses in this example, though it should be understood that other configurations may be used. Each segment (1012A, 1012B) has a respective pair of coupling features (1013), which provide hinged couplings between segments (1012A, 1012B) and the rest of outer tube (1010). The coupling features (1013) in each pair are angularly offset from each other by 180°. Segments (1012A, 1012B) are also separated from each other and from the remainder of outer tube (1010) by gaps (1015). Each segment (1012A, 1012B) also includes a pair of proximally oriented projections (1017) traversing respective gaps (1015), as best seen in FIG. 21. The projections (1017) in each pair are angularly offset from each other by 180°. In each segment (1012A, 1012B), the coupling features (1013) are angularly offset from the projections (1017) by 90°, such that coupling features (1013) and projections (1017) are alternatingly and evenly positioned along the proximally facing perimeter of each segment (1012A, 1012B).

Coupling features (1013), gaps (1015), and projections (1017) are configured to allow segmented region (1012) to flex. However, projections (1017) prevent segments (1012A, 1012B) from rotating relative to each other and relative to the remainder of outer tube (1010). In some versions, coupling features (1013), gaps (1015), and projections (1017) are formed by a laser cutting process, though it should be understood that any other suitable processes may be used.

Figure 22:
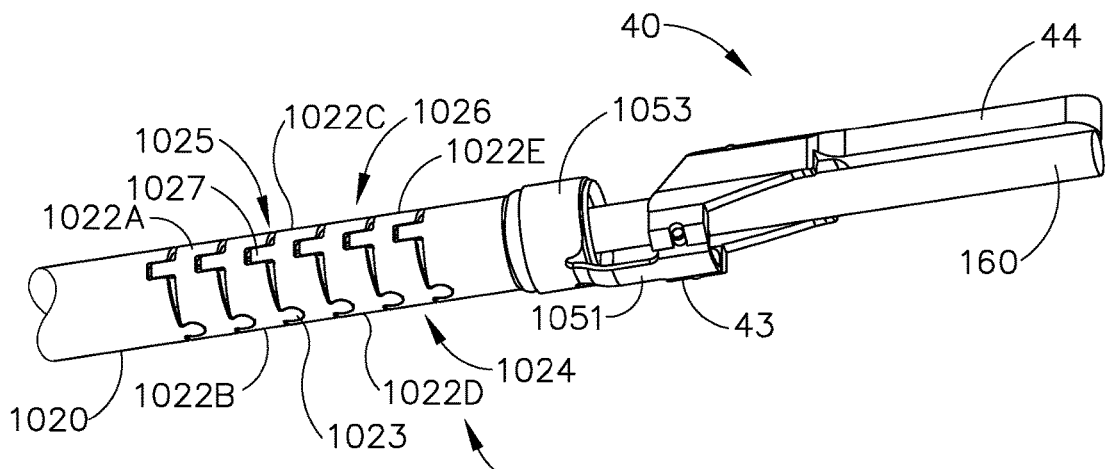
FIG. 22 depicts a perspective view of the articulation section and end effector of FIG. 21, with an outer sheath removed.
Figure 26:
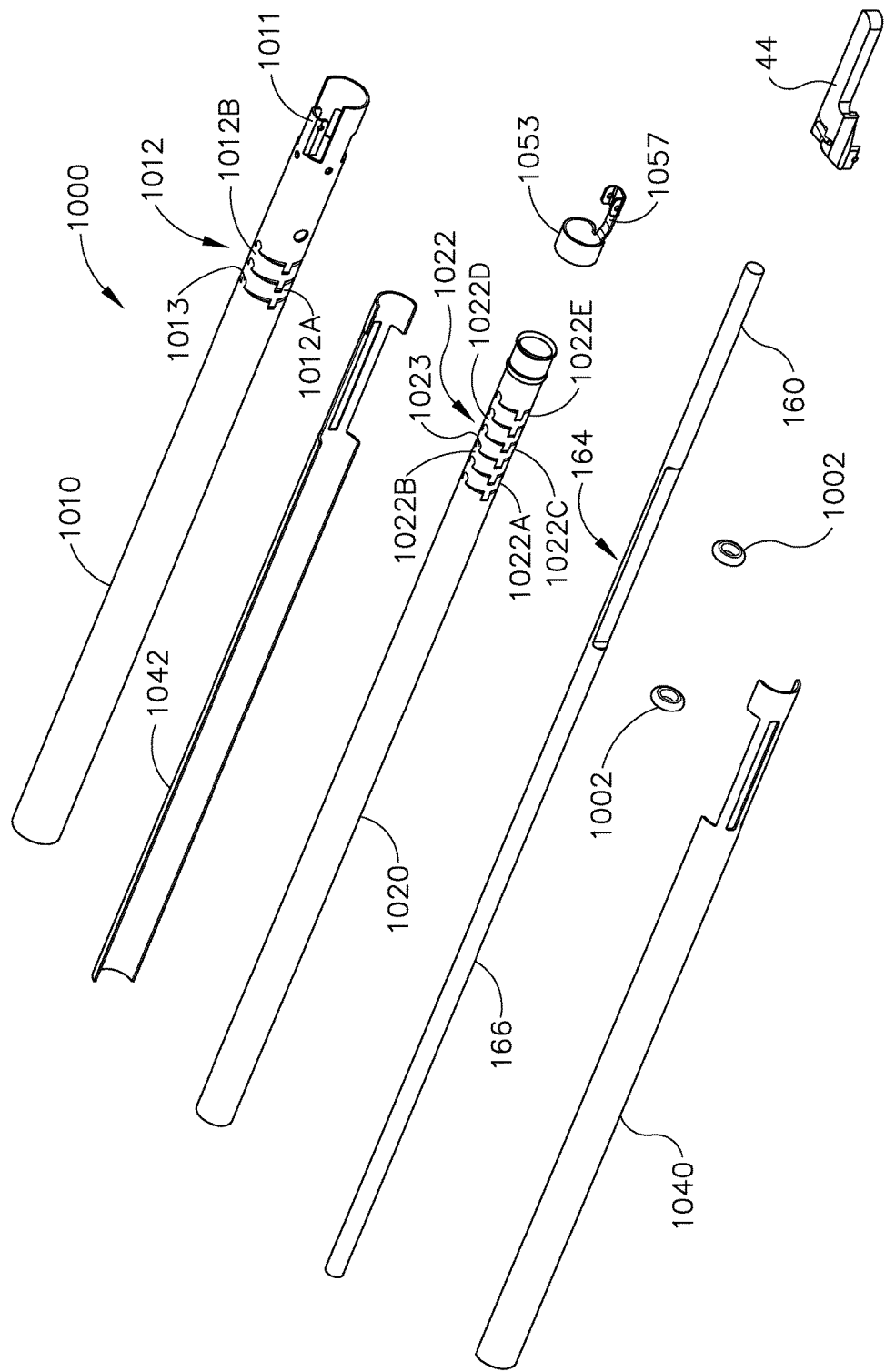
FIG. 26 depicts an exploded perspective view of the articulation section and end effector of FIG. 21.
Figure 27:
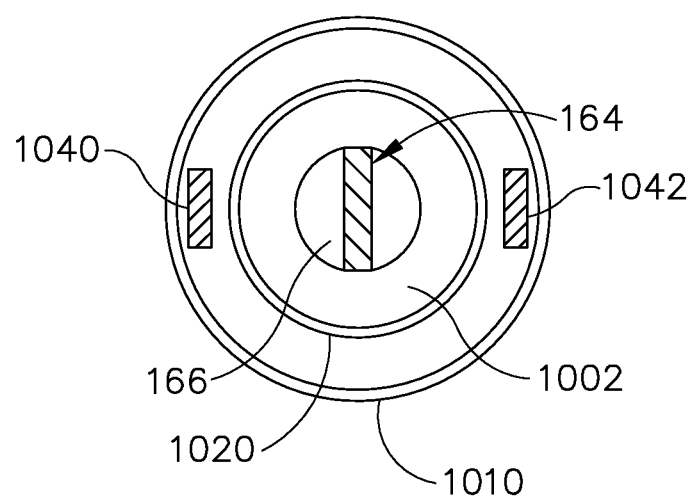
FIG. 27 depicts a cross-sectional end view of the articulation section of FIG. 21.

Similarly, segmented region (1022) of inner tube (1020) comprises a plurality of segments (1022A, 1022B). Segments (1022A, 1022B, 1022C, 1022D, 1022E) are joined to each other and to the remainder of inner tube (1020) by coupling features (1023), which are best seen in FIG. 26. Each segment (1022A, 1022B, 1022C, 1022D, 1022E) has a respective pair of coupling features (1023), which provide hinged couplings between segments (1022A, 1022B, 1022C, 1022D, 1022E) and the rest of inner tube (1020). The coupling features (1023) in each pair are angularly offset from each other by 180°. Segments (1022A, 1022B, 1022C, 1022D, 1022E) are also separated from each other and from the remainder of inner tube (1020) by gaps (1025). Each segment (1022A, 1022B, 1022C, 1022D, 1022E) also includes a pair of proximally oriented projections (1027) traversing respective gaps (1025), as best seen in FIG. 22. The projections (1027) in each pair are angularly offset from each other by 180°. In each segment (1022A, 1022B, 1022C, 1022D, 1022E), the coupling features (1023) are angularly offset from the projections (1027) by 90°, such that coupling features (1023) and projections (1027) are alternatingly and evenly positioned along the proximally facing perimeter of each segment (1022A, 1022B, 1022C, 1022D, 1022E).

Coupling features (1023), gaps (1025), and projections (1027) are configured to allow segmented region (1022) to flex. Projections (1017) are configured to prevent segments (1022A, 1022B, 1022C, 1022D, 1022E) from rotating relative to each other and relative to the remainder of inner tube (1020). As noted above, inner tube (1020) is translatable relative to outer tube (1010). Coupling features (1023), gaps (1025), and projections (1027) are configured to allow segmented region (1022) to translate longitudinally relative to segmented region (1012), even when segmented regions (1012, 1022) are both in a bent configuration. In some versions, coupling features (1023), gaps (1025), and projections (1027) are formed by a laser cutting process, though it should be understood that any other suitable processes may be used.

Figure 23:
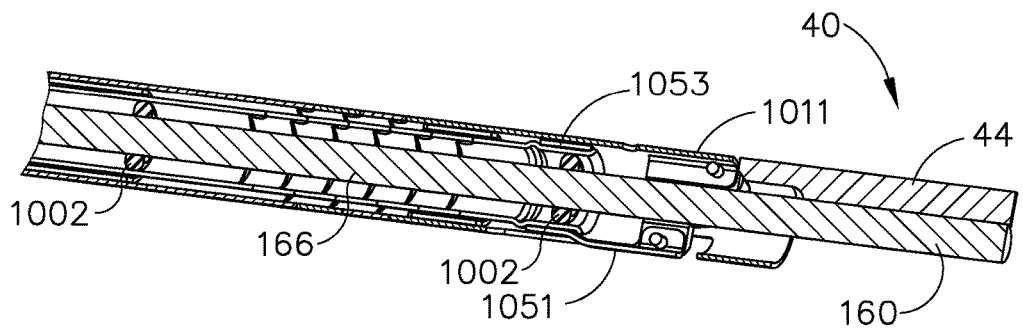
FIG. 23 depicts a cross-sectional view of the articulation section and end effector of FIG. 21, with the articulation section in a straight configuration.
Figure 24:
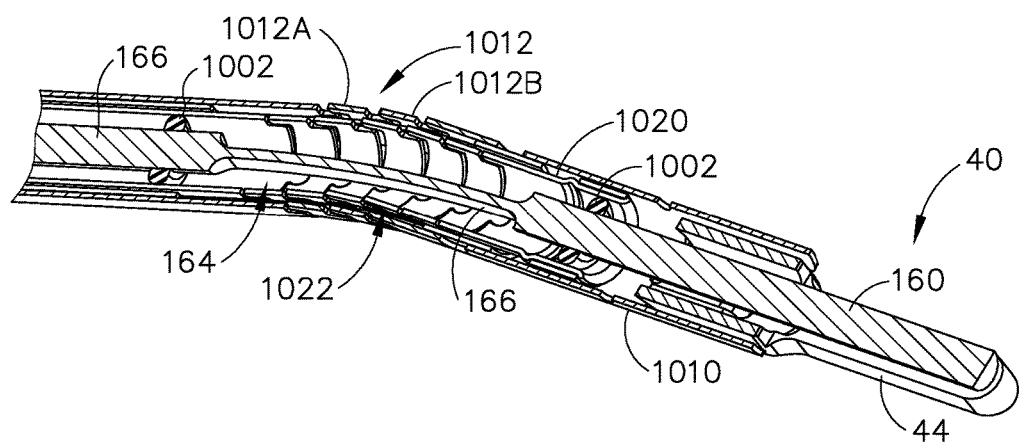
FIG. 24 depicts a cross-sectional view of the articulation section and end effector of FIG. 21, with the articulation section in a bent configuration.

Waveguide (166) extends coaxially through inner tube (1020). As best seen in FIGS. 23-24, a set of spacers (1002) are used to maintain separation between waveguide (166) and inner tube (1020). Spacers (1002) are located at positions corresponding to nodes associated with resonant ultrasonic vibrations communicated through flexible acoustic waveguide (166). One spacer (1002) is located proximal to articulation section (1000) while the other spacer (1002) is located distal to articulation section (1000). It should be understood that spacers (1002) provide isolation of waveguide (166) from inner tube (1020), even through articulation section (1000) when articulation section (1000) is in an articulated state. In some versions, spacers (1002) comprise o-rings, though it should be understood that spacers (1002) may take any other suitable alternative form.

As best seen in FIGS. 22 and 26, a collar (1053) is secured to the distal end of inner tube (1020). A tongue (1051) projects distally from collar (1053). Clamp arm (44) of end effector (40) is pivotally secured to tongue (1051). Clamp (44) arm is thereby secured to inner tube (1020). This coupling between clamp arm (44) and inner tube (1020) permits clamp arm (44) to pivot about an axis that is transverse to inner tube (1020). This coupling between clamp arm (44) and inner tube (1020) also permits clamp arm (44) to rotate relative to inner tube (1020), about the longitudinal axis defined by inner tube (1020). However, the coupling between clamp arm (44) and inner tube (1020) prevents clamp arm (44) from translating relative to inner tube (1020), such that clamp arm (44) will translate with inner tube (1020). Clamp arm (44) is also pivotally coupled with a distally projecting tongue (1011) of outer tube (1010). Tongue (1011) is best seen in FIGS. 23 and 26.

As noted above, inner tube (1020) may be translated longitudinally relative to outer tube (1010). It should therefore be understood that clamp arm (44) may be pivoted away from blade (160) by advancing inner tube (1020) distally relative outer tube (1010); and that clamp arm (44) may be pivoted toward blade (160) by retracting inner tube (1020) proximally relative to outer tube (1010). In some other versions, outer tube (1010) is retracted proximally relative to inner tube (1020) in order to pivot clamp arm (44) away from blade (160); and advanced distally relative to inner tube (1020) in order to pivot clamp arm (44) toward blade (160).

As also noted above outer tube (1010) may be rotated about inner tube (1020). Since collar (1023) permits rotation of tongue (1021) and clamp arm (44) relative to inner tube (1020), it should be understood that rotation of outer tube (1010) about inner tube (1020) may result in rotation of tongue (1021) and clamp arm (44) about inner tube (1020) and blade (160). Such rotation may be driven by manual rotation of knob (31) and/or using some other feature(s). Since blade (160) remains rotationally stationary relative to clamp arm (44), rotating clamp arm (44) about blade (160) may enable selective positioning of clamp arm (44) relative to particular geometric features (e.g., multifaceted faces/edges) of blade (160), which may in turn provide varying effects on tissue engaged by end effector (40). In some versions, waveguide (166) and blade (160) are also rotatable relative to inner tube (1020), which may provide further control over the orientation and configuration of end effector (40).

Two articulation bands (1040, 1042) extend through a gap defined between outer tube (1010) and outer tube (1020). The distal ends of articulation bands (1040, 1042) are secured to outer tube (1020). Alternatively, articulation bands (1040, 1042) may be secured to outer tube (1010) (e.g., in versions where inner tube (1020) is translated relative to outer tube (1010) in order to drive clamp arm (44) toward and away from blade (160)). As with cables (140, 142) described herein, articulation bands (1040, 1042) are operable to translate longitudinally in opposing direction to articulate articulation section (1000). FIGS. 24-25 show an example of articulation section (1000) in an articulated state.

Figure 28:
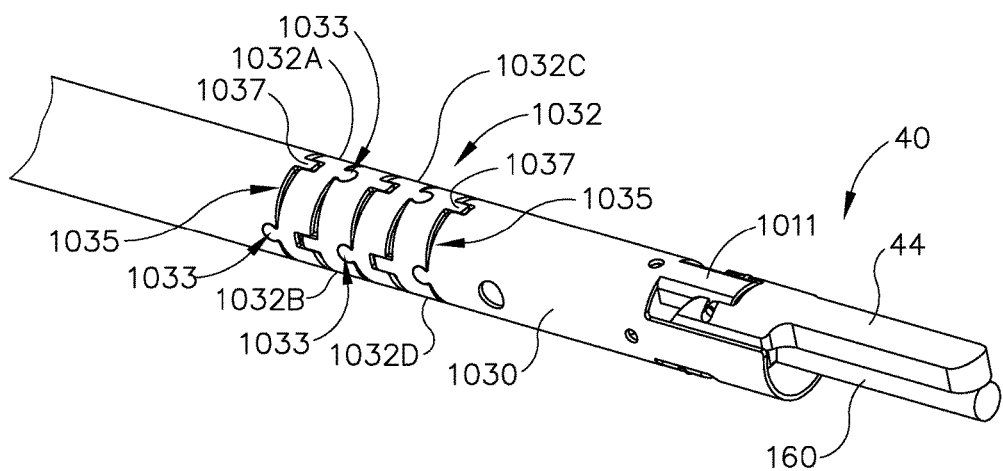
FIG. 28 depicts a perspective view of the articulation section and end effector of FIG. 21 with an exemplary alternative outer sheath.

In some instances, it may be desirable to rotate outer tube (1010) about inner tube (1020) when articulation section (1000) is in an articulated state (i.e., when segmented regions (1012, 1022) are in bent configurations). Such action of outer tube (1010) may be promoted by using a configuration of an outer tube (1030) as shown in FIG. 28. Outer tube (1030) of this example is substantially similar to outer tube (1010) described above. However, outer tube (1030) of this example has a segmented region (1032) with more segments (1032A, 1032B, 1032C, 1032D) than segmented region (1012).

Like segments (1012A, 1012B), segments (1032A, 1032B, 1032C, 1032D) of the example shown in FIG. 28 are joined to each other and to the remainder of outer tube (1030) by coupling features (1033). Each segment (1032A, 1032B, 1032C, 1032D) has a respective pair of coupling features (1033), which provide hinged couplings between segments (1032A, 1032B, 1032C, 1032D) and the rest of outer tube (1030). The coupling features (1033) in each pair are angularly offset from each other by 180°. Segments (1032A, 1032B, 1032C, 1032D) are also separated from each other and from the remainder of outer tube (1030) by gaps (1035). Each segment (1032A, 1032B, 1032C, 1032D) also includes a pair of proximally oriented projections (1037) traversing respective gaps (1035). The projections (1037) in each pair are angularly offset from each other by 180°. In each segment (1032A, 1032B, 1032C, 1032D), the coupling features (1033) are angularly offset from the projections (1037) by 90°, such that coupling features (1033) and projections (1037) are alternatingly and evenly positioned along the proximally facing perimeter of each segment (1032A, 1032B, 1032C, 1032D).

Unlike segments (1013A, 1013B), segments (1032A, 1032B, 1032C, 1032D) are angularly offset relative to each other by 90°. Thus, instead of coupling features (1033) all being aligned with each other along segments (1032A, 1032B, 1032C, 1032D) and projections (1037) all being aligned with each other along segments (1032A, 1032B, 1032C, 1032D), coupling features (1033) and projections (1037) alternate along segments (1032A, 1032B, 1032C, 1032D). This arrangement allows segmented region (1032) to rotate about segmented region (1022) while segmented regions (1032, 1022) are both in a bent configuration. Of course, this arrangement also allows segmented region (1032) to flex; and prevents segments (1032A, 1032B, 1032C, 1032D) from rotating relative to each other. As with the features of segmented region (1012), the features of segmented region (1030) may be formed by a laser cutting process and/or any other suitable processes.

Figure 29:
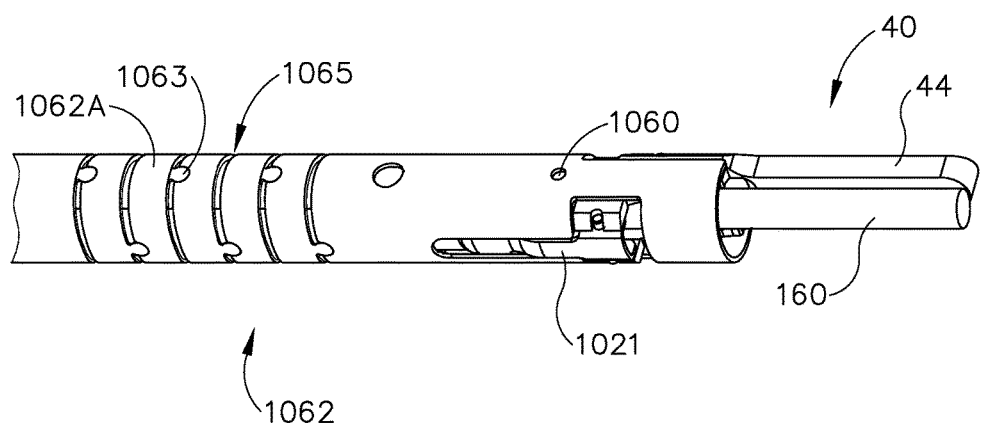
FIG. 29 depicts a perspective view of the articulation section and end effector of FIG. 21 with another exemplary alternative outer sheath.

FIG. 29 shows yet another exemplary configuration of outer tube (1060) that may be used to provide rotatability of outer tube (1060) about inner tube (1020) during an articulated state. Outer tube (1060) of this example includes a segmented region (1062) that has a single continuous segment (1062A) defined by a spiral cut gap (1065). A plurality of coupling features (1033) traverse spiral cut gap (1065) in an angularly alternating fashion. These coupling features (1033) provide hinged couplings between adjacent portions of segment (1062A). This arrangement allows segmented region (1062) to rotate about segmented region (1022) while segmented regions (1062, 1022) are both in a bent configuration. Of course, this arrangement also allows segmented region (1062) to flex; and prevents portions of segment (1062A) from rotating relative to each other. As with the features of segmented region (1012), the features of segmented region (1060) may be formed by a laser cutting process and/or any other suitable processes.

Figure 30:
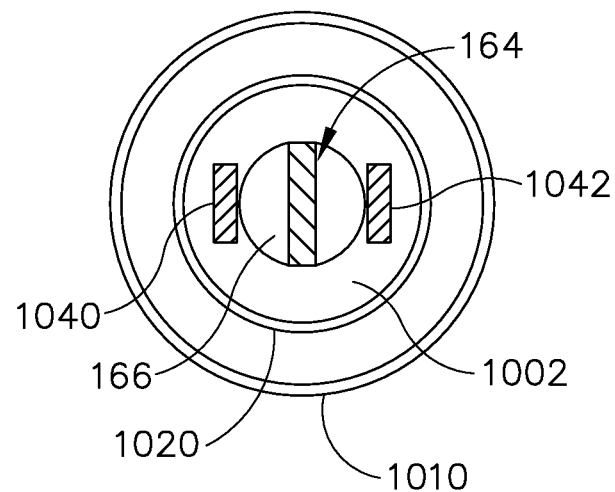
FIG. 30 depicts a cross-sectional end view of an exemplary alternative configuration of the articulation section of FIG. 21.
Figure 31:
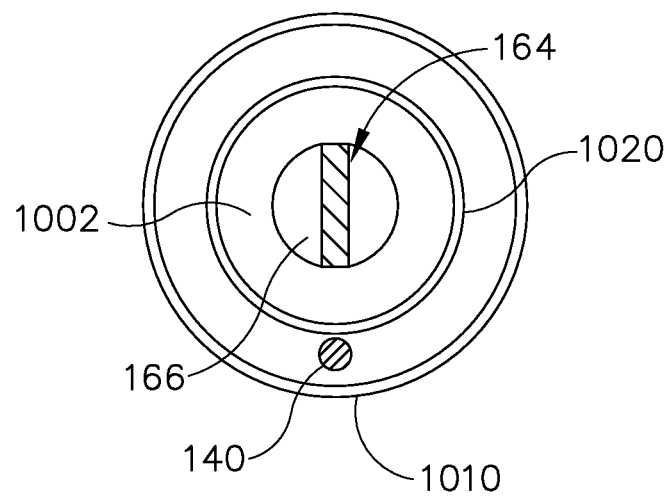
FIG. 31 depicts a cross-sectional end view of another exemplary alternative configuration of the articulation section of FIG. 21.

FIG. 30 shows an exemplary alternative arrangement positioning for articulation bands (1040, 1042). In this example, articulation bands (1040, 1042) are positioned within inner tube (1020). By way of example only, articulation bands (1040, 1042) may pass through one or more spacers (1002). The distal ends of articulation bands (1040, 1042) may be secured to inner tube (1020) to provide articulation. FIG. 31 shows yet another merely illustrative example where articulation bands (1040, 1042) are omitted in favor of an articulation cable (140), which is positioned in a gap between inner tube (1020) and outer tube (1010). The distal end of articulation cable (140) may be secured to inner tube (1020) to provide articulation. In the examples shown in FIGS. 30-31, end effector (40) may be rotated relative to outer tube (1010) and outer sheath (32) via inner tube (1020). Other suitable arrangements and operabilities will be apparent to those of ordinary skill in the art in view of the teachings herein.

Figure 32:
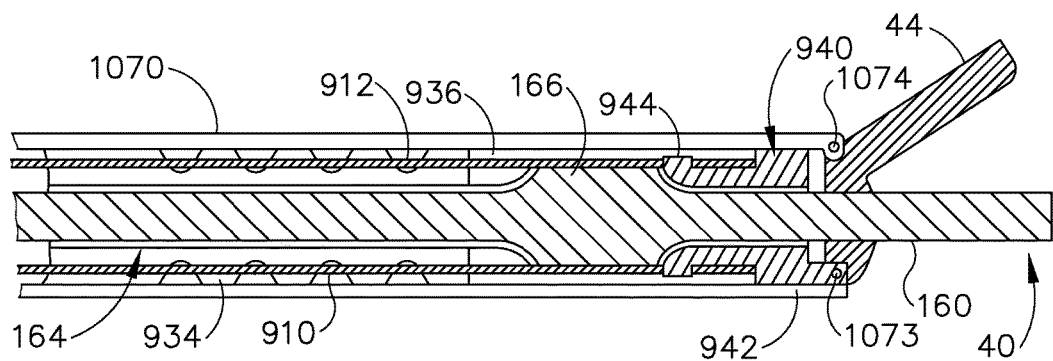
FIG. 32 depicts a cross-sectional side view of an exemplary alternative articulation section with a clamp arm closure sheath, with the clamp arm in an open position and the articulation section in a straight configuration.
Figure 33:
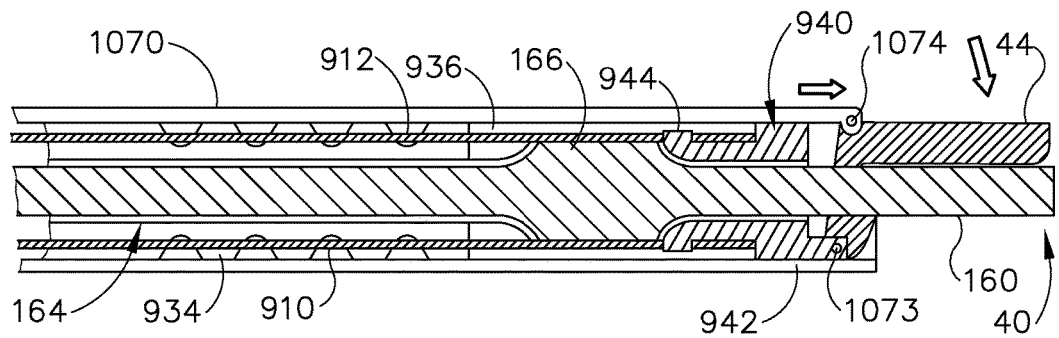
FIG. 33 depicts a cross-sectional side view of the articulation section of FIG. 32, with the clamp arm in a closed position and the articulation section in a straight configuration.
Figure 34:
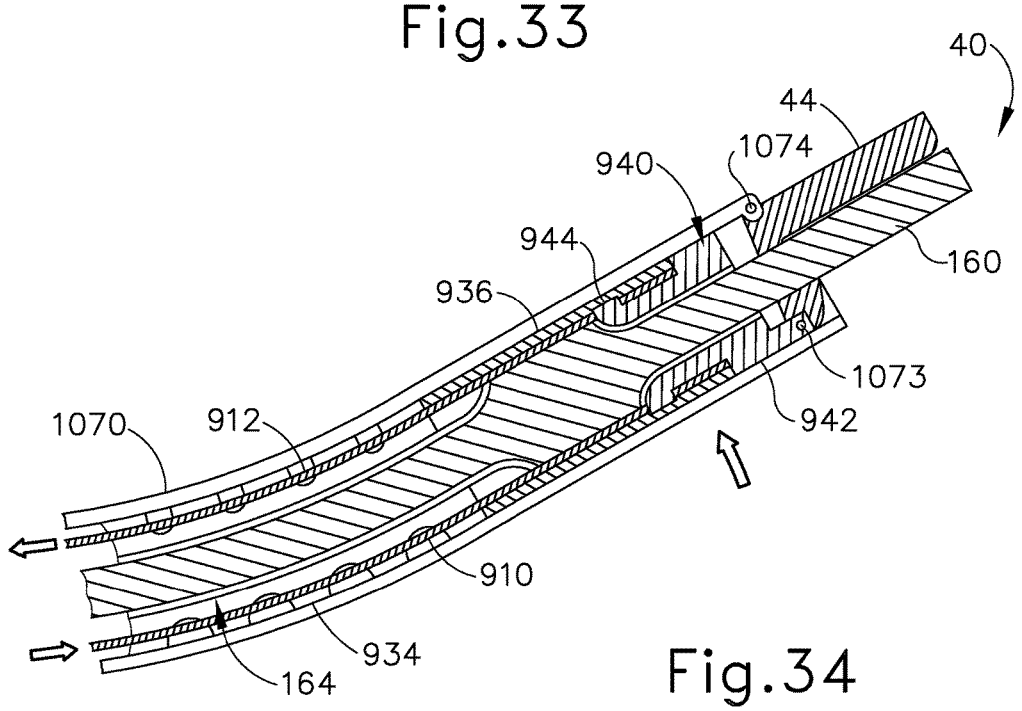
FIG. 34 depicts a cross-sectional side view of the articulation section of FIG. 32, with the clamp arm in a closed position and the articulation section in a bent configuration.

D. Exemplary Articulation Section with Articulation Bands and Flexible Closure Sleeve FIGS. 32-34 show a configuration that combines articulation section (900), described above, with a flexible closure sleeve (1070). In this example, clamp arm (44) is pivotally coupled with distal flange (942) of distal collar (940) by a pin (1073). Flexible closure sleeve (1070) is slidably disposed over articulation section (900) and is pivotally coupled with clamp arm (44) by another pin (1074). When flexible closure sleeve (1070) is slid distally relative to articulation section (900), flexible closure sleeve (1070)

drives clamp arm (44) pivotally toward blade (160) as shown in FIG. 33. When flexible closure sleeve (1070) is subsequently slid proximally relative to articulation section (900), flexible closure sleeve (1070) drives clamp arm (44) pivotally away from blade (160). Flexible closure sleeve (1070) thus has sufficient column strength and tensile to drive clamp arm (44) toward and away from blade (160). However, flexible closure sleeve (1070) also has sufficient flexibility to permit articulation section (900) to articulate, regardless of whether clam arm (44) is in an open or closed position, as shown in FIG. 34. These properties may be provided in flexible closure sleeve (1070) in various ways, including but not limited to configurations (e.g., linked sections, ribs, etc.) and/or material selections (e.g., elastomeric, Teflon coating, etc.). Various suitable ways in which closure sleeve (1070) may be formed and configured will be apparent to those of ordinary skill in the art in view of the teachings herein.

E. Exemplary Linked Articulation Band Mechanism

Figure 35A:
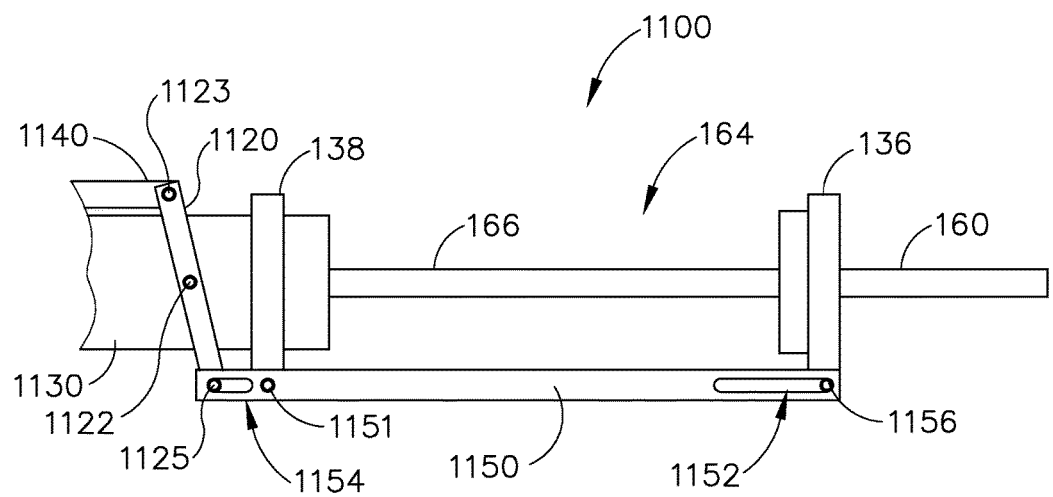
FIG. 35A depicts a top plan view of yet another exemplary articulation section in a straight configuration.
Figure 35B:
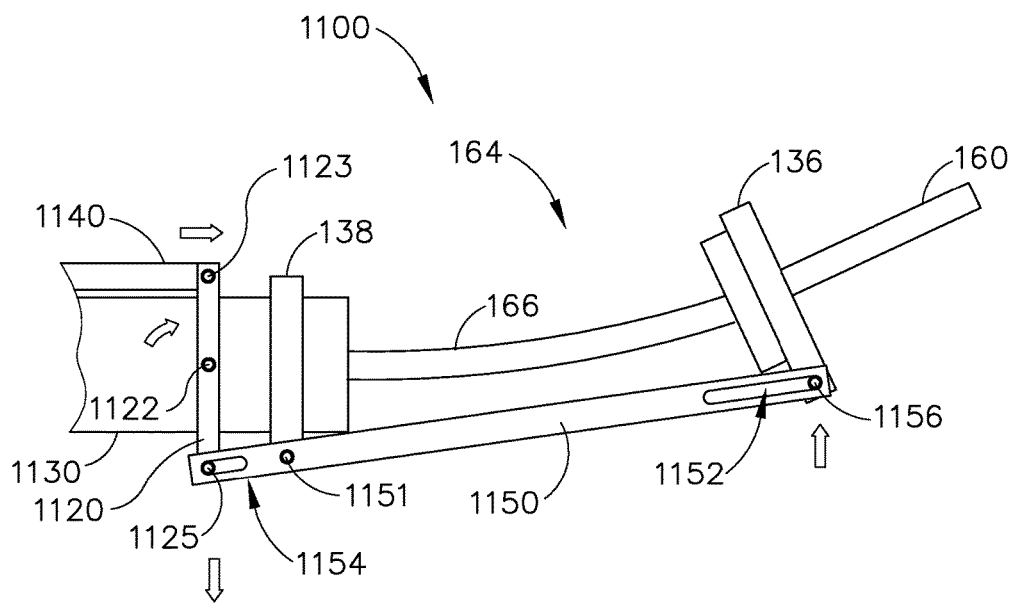
FIG. 35B depicts a top plan view of the articulation section of FIG. 35A in a first bent configuration.
Figure 35C:
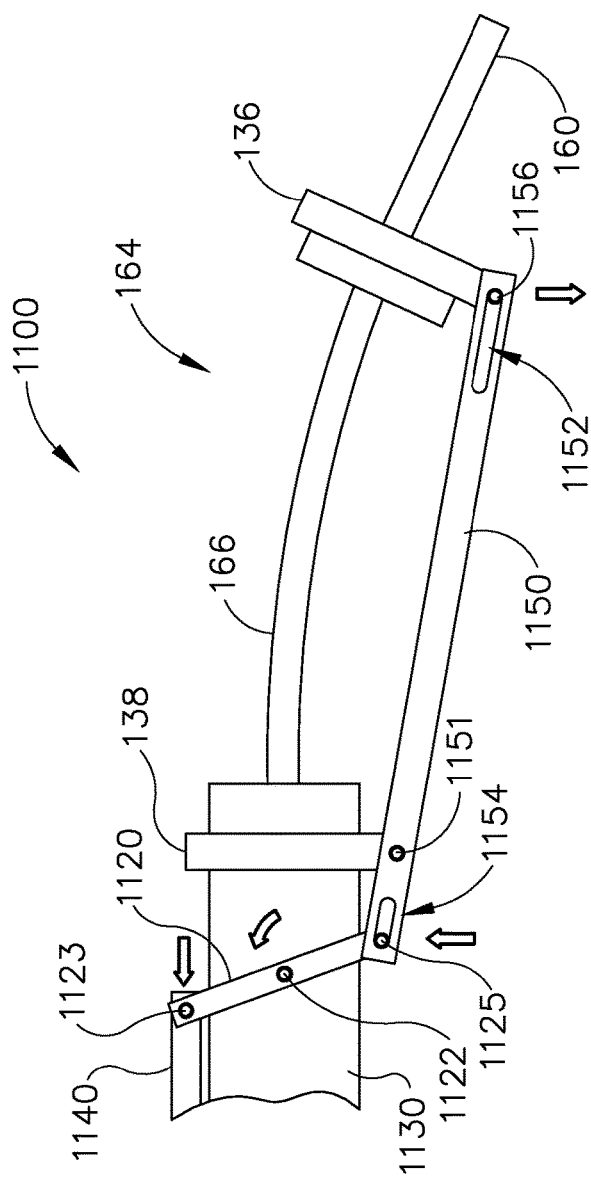
FIG. 35C depicts a top plan view of the articulation section of FIG. 35A in a second bent configuration.
Figure 36:
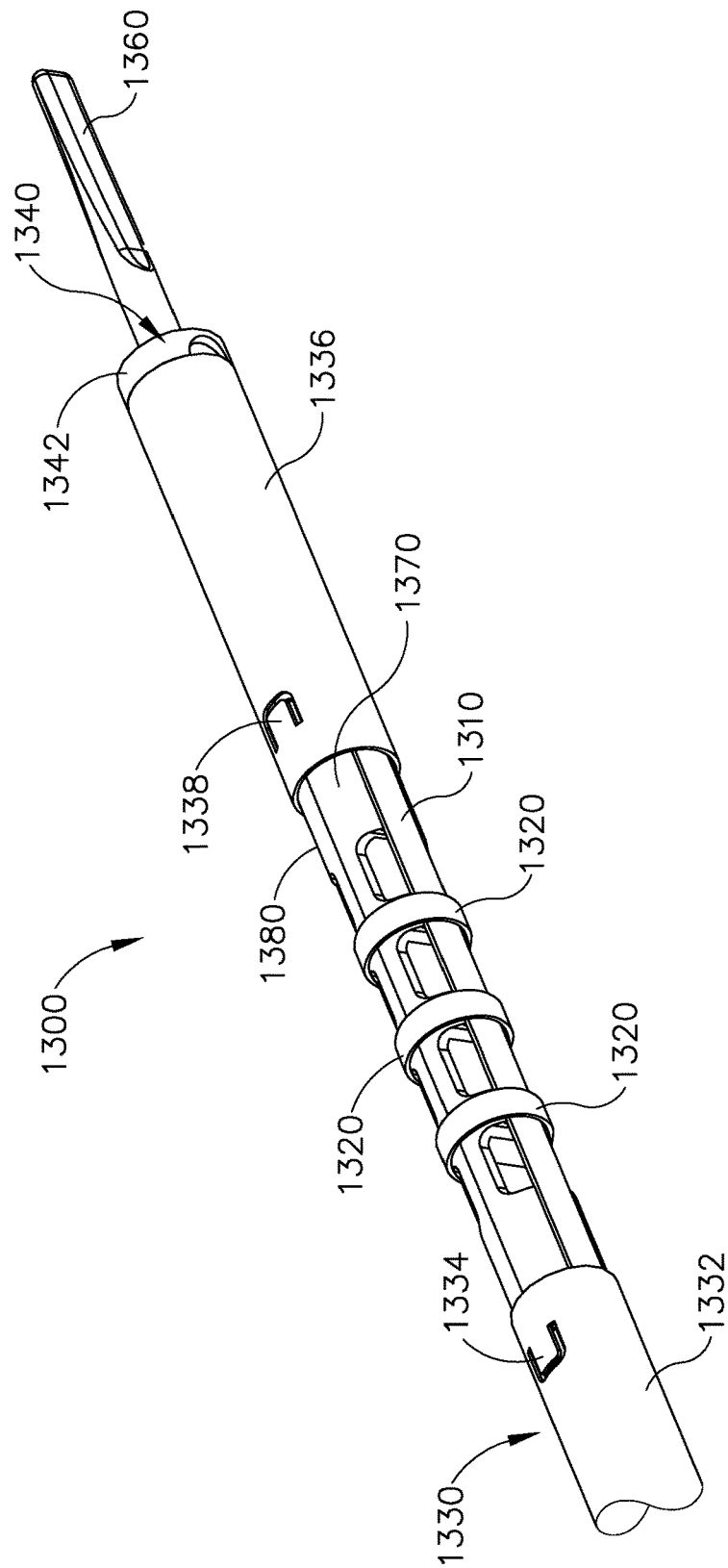
FIG. 36 depicts a perspective view of another exemplary articulation section.

FIGS. 35A-35C show another exemplary alternative mechanism (1100) that may be used in place of articulation cables (140, 142) to laterally deflect end effector (40) away from the longitudinal axis of shaft assembly (30). Mechanism (1100) of this example comprises an articulation band (1140) that is configured to translate longitudinally relative to shaft assembly (30). Shaft assembly (30) comprises an inner tube (1130), which is configured to remain longitudinally stationary as articulation band (1140) translates longitudinally. Flexible acoustic waveguide (166) is disposed within inner tube (1130) and extends distally from inner tube (1130).

Mechanism (1100) of the present example further comprises a pivoting link (1120). An intermediate portion of pivoting link (1120) is rotatably secured to inner tube (1130) by a pivot (1122), such that pivoting link (1120) is rotatable relative to inner tube (1130) about an axis defined by pivot (1122). A distal end of articulation band (1140) is rotatably secured to a first end of pivoting link (1120) via a pin (1123) such that longitudinal translation of articulation band (1140) causes rotation of pivoting link (1120) relative to inner tube (1130) about an axis defined by pivot (1122). Mechanism (1100) further comprises a drive lever (1150). A first end of drive lever (1150) is slidably and rotatably secured to a second end of pivoting link (1120) via a slot (154) and pin (1125). A second end of drive lever (1150) is slidably and rotatably coupled to distal flange (136) via a slot (1152) and pin (1156). An intermediate portion of drive lever (1150) is rotatably coupled to proximal flange (138) via a pin (1151). Drive lever (1150) is rotatable relative to proximal flange (138) about an axis defined by pin (1151).

As shown in FIG. 35B, distal longitudinal movement of articulation band (1140) causes clockwise rotation of pivoting link (1120). Clockwise rotation of pivoting link (1120) will drive the first end of drive lever (1150) laterally away from inner tube (1130). Lateral movement of the first end of drive lever (1150) away from inner tube (1130) will drive the second end of drive lever (1150) and thus distal flange (136) lateral in the opposite direction. This lateral movement of flange (136) will cause deflection of flexible acoustic waveguide (166) and blade (160).

As shown in FIG. 35C, proximal longitudinal movement of articulation band (1140) causes counter-clockwise rotation of pivoting link (1120). Counter-clockwise rotation of pivoting link (1120) will drive the first end of drive lever (1150) laterally toward inner tube (1130). Lateral movement of the first end of drive lever (1150) toward inner tube (1130) will drive the second end of drive lever (1150) and thus distal flange (136) lateral in the opposite direction. This lateral movement of flange (136) will cause deflection of flexible acoustic waveguide (166) and blade (160), in a direction opposite to that shown in FIG. 35B.

F. Exemplary Articulation Section with Articulation Bands and Retaining Rings

FIGS. 36-42 depict another exemplary articulation section (1300) that may be interposed between a shaft assembly (1330) and end effector (40) in place of articulation section (130), to selectively position an ultrasonic blade (1360) at various lateral deflection angles relative to the longitudinal axis defined by shaft assembly (130). Shaft assembly (1330) of this example is substantially identical to shaft assembly (30) described above and includes an outer sheath (1332). While an end effector (40) with clamp arm (44) is not shown in this example, it should be understood that articulation section (1300) may be readily incorporated into an instrument that has an end effector (40) with clamp arm (44). Articulation section (1300) of this example comprises a pair of articulation bands (1310, 1314), a set of three retention collars (1320), and a pair of ribbed body portions (1370, 1380). A distal outer tube (1336) and a distal collar (1340) are located distal to a bendable region of articulation section (1300).

Figure 38:
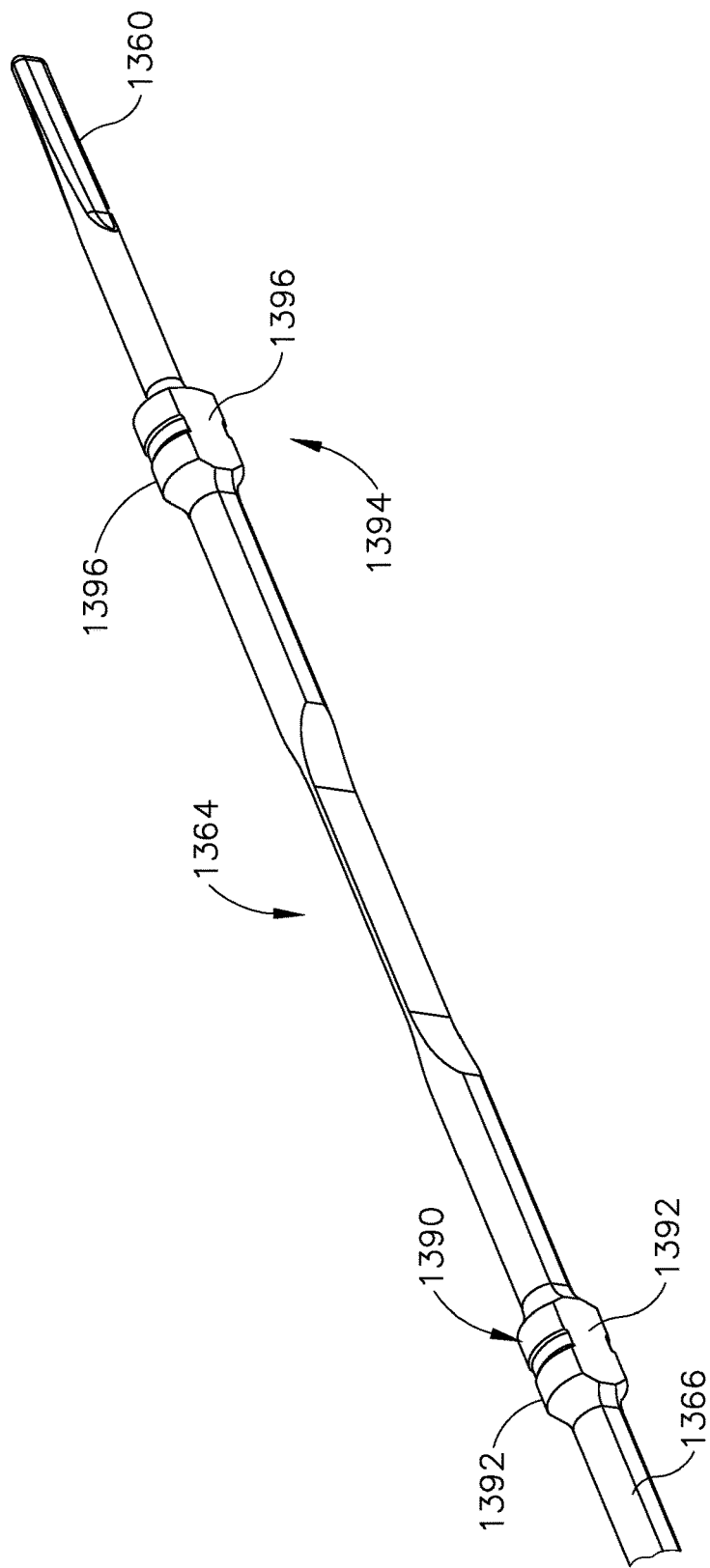
FIG. 38 depicts a perspective view of the distal portion of the waveguide that extends through the articulation section of FIG. 36.

Articulation section (1300) of the present example is used with a waveguide (1366) as best seen in FIG. 38. Of course, articulation section (1300) could alternatively be used with any other suitable kind of waveguide. Waveguide (1366) of this example is substantially similar to waveguide (166) described above. In particular, waveguide (1366) includes a flexible narrowed section (1364) that is longitudinally positioned between a proximal flange (1390) and a distal flange (1394). Distal flange (1394) is located at a position along the length of waveguide (1366) corresponding to a distal-most node associated with resonant ultrasonic vibrations communicated through waveguide (1366). Proximal flange (1390) is located at a position along the length of waveguide (1366) corresponding to a second-to-distal-most node associated with resonant ultrasonic vibrations communicated through waveguide (1366). Waveguide (1366) may be readily coupled with a transducer assembly such as transducer assembly (12) described above. Transducer assembly (12) may thus generate ultrasonic vibrations that are transmitted along waveguide (1366) to blade (1360) in accordance with known configurations and techniques.

Figure 42:
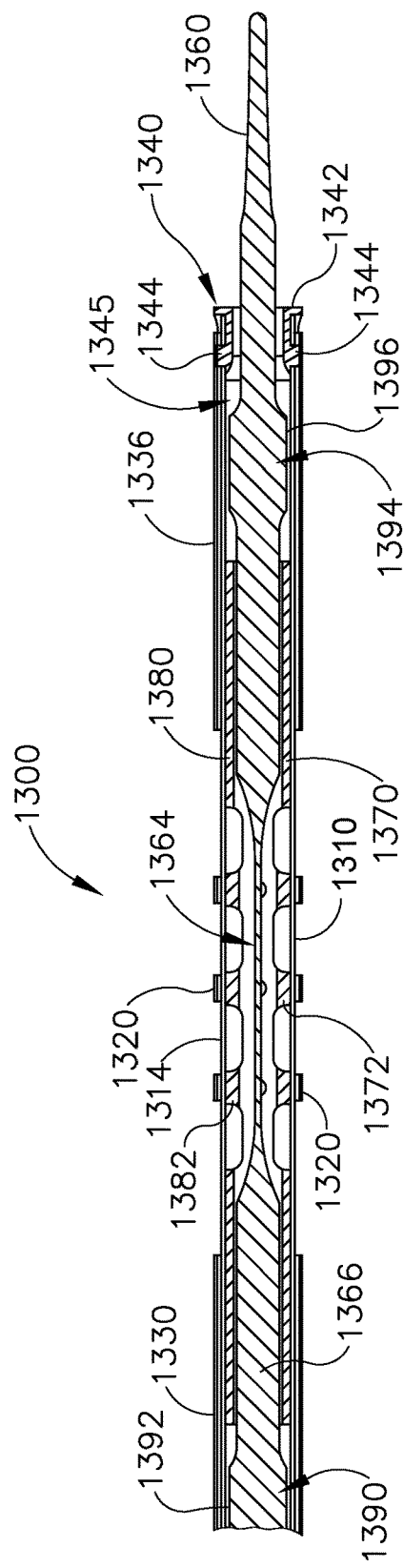
FIG. 42 depicts a top cross-sectional view of the articulation section of FIG. 36.

Each flange (1390, 1394) includes a respective pair of opposing flats (1392, 1396) in this example. Flats (1392, 1396) are oriented along vertical planes that are parallel to a vertical plane extending through narrowed section (1364) in the present example. Flats (1392, 1396) are configured to provide clearance for articulation bands (1310, 1314) as best seen in FIG. 42. In particular, flats (1392) accommodate articulation bands (1310, 1314) between proximal flange (1390) and the inner diameter of outer sheath (1332): while flats (1396) accommodate articulation bands (1310, 1314) between distal flange (1394) and the inner diameter of distal outer tube (1336). Of course, flats (1392, 1396) could be substituted with a variety of features, including but not limited to slots, channels, etc., with any suitable kind of profile (e.g., square, flat, round, etc.). In the present example, flats (1392, 1396) are formed in a milling process, though it should be understood that any other suitable process(es) may be used. Various suitable alternative configurations and methods of forming flats (1392, 1396) will be apparent to those of ordinary skill in the art in view of the teachings herein. It should also be understood that waveguide (1366) may include flats formed in accordance with at least some of the teachings of U.S. patent application Ser. No. 13/868,336, entitled "Ultrasonic Device for Cutting and Coagulating," filed Apr. 23, 2013, now U.S. Patent Pub. No. 2013/0289592, published Oct. 31, 2013, the disclosure of which is incorporated by reference herein.

Figure 39:
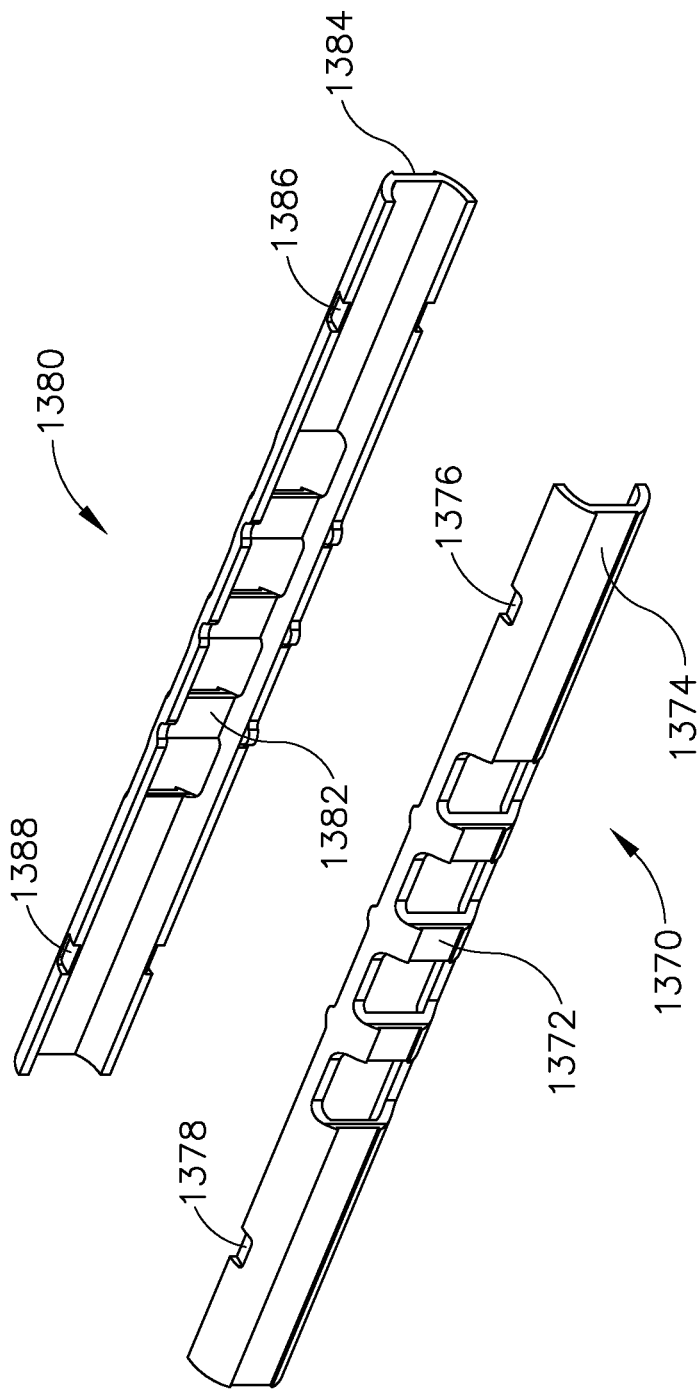
FIG. 39 depicts a perspective view of a pair of ribbed body portions of the articulation section of FIG. 36.

FIG. 39 shows ribbed body portions (1370, 1380) in greater detail. In the present example, ribbed body portions (1370, 1380) are formed of a flexible plastic material, though it should be understood that any other suitable material may be used. Ribbed body portion (1370) comprises a set of three ribs (1372) that are configured to promote lateral flexing of ribbed body portion (1370). Of course, any other suitable number of ribs (1372) may be provided. Ribbed body portion (1370) also defines a channel (1374) that is configured to receive articulation band (1310) while allowing articulation band (1310) to slide relative to ribbed body portion (1370). Similarly, ribbed body portion (1380) comprises a set of three ribs (1382) that are configured to promote lateral flexing of ribbed body portion (1380). Of course, any other suitable number of ribs (1382) may be provided. Ribbed body portion (1380) also defines a channel (1384) that is configured to receive articulation band (1380) while allowing articulation band (1314) to slide relative to ribbed body portion (1380).

Figure 37:
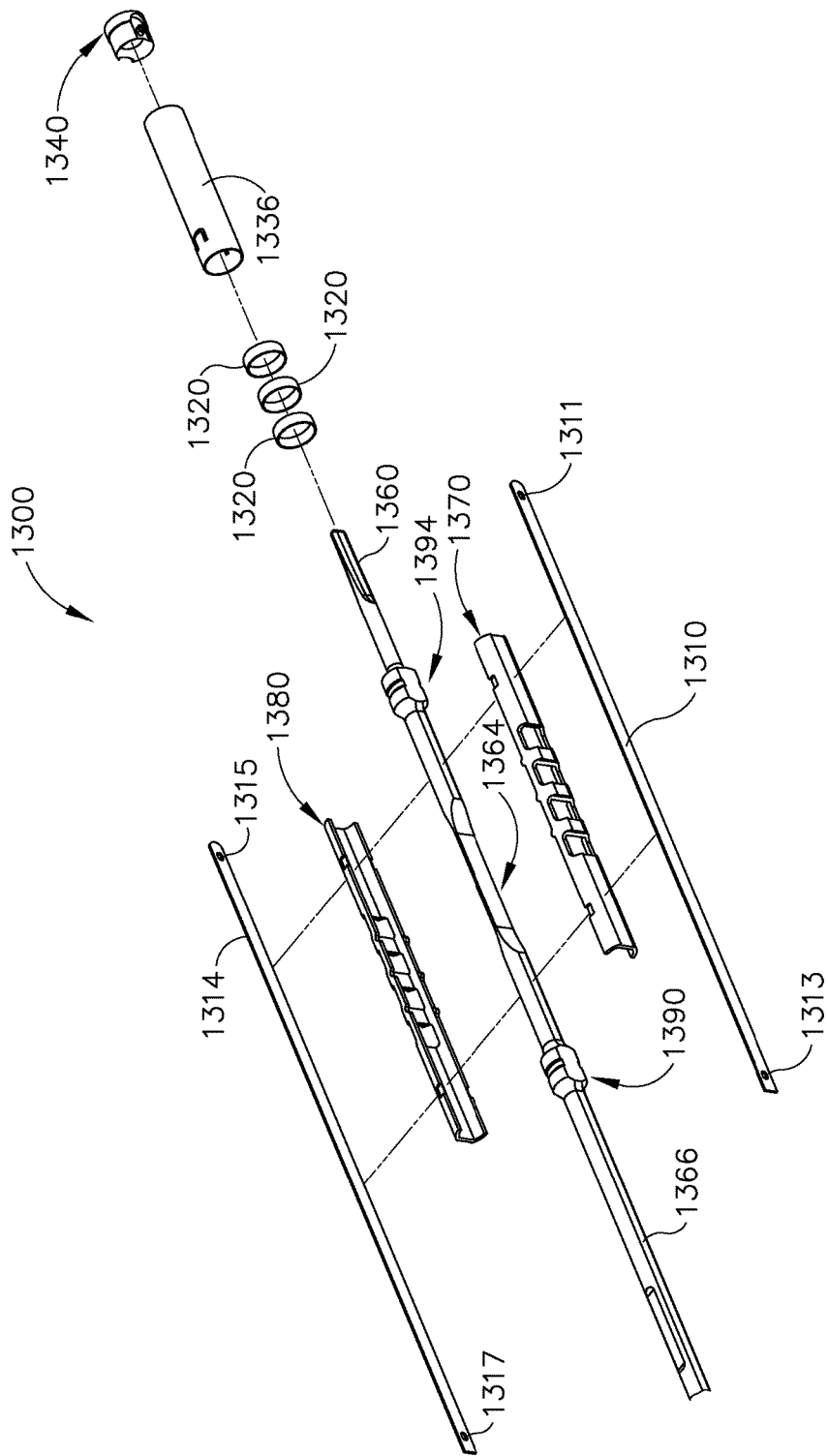
FIG. 37 depicts an exploded perspective view of the articulation section of FIG. 36.

As best seen in FIGS. 37 and 42, ribbed body portions (1370, 1380) are laterally interposed between articulation bands (1310, 1314) and waveguide (1366). Ribbed body portions (1370, 1380) mate with each other such that they together define an internal passage sized to accommodate waveguide (1366) without contacting waveguide (1366). In addition, when ribbed body portions (1370, 1380) are coupled together, a pair of complementary distal notches (1376, 1386) formed in ribbed body portions (1370, 1380) align to receive an inwardly projecting tab (1338) of distal outer tube (1336). This engagement between tab (1338) and notches (1376, 1386) longitudinally secures ribbed body portions (1370, 1380) relative to distal outer tube (1336). Similarly, when ribbed body portions (1370, 1380) are coupled together, a pair of complementary proximal notches (1378, 1388) formed in ribbed body portions (1370, 1380) align to receive an inwardly projecting tab (1334) of outer sheath (1332). This engagement between tab (1334) and notches (1378, 1388) longitudinally secures ribbed body portions (1370, 1380) relative to outer sheath (1332). Of course, any other suitable kinds of features may be used to couple ribbed body portions (1370, 1380) with outer sheath (1332) and/or distal outer tube (1336).

In the present example, outer rings (1320) are located at longitudinal positions corresponding to ribs (1372, 1382), such that three rings (1320) are provided for three ribs (1372, 1382). Articulation band (1310) is laterally interposed between rings (1320) and ribbed body portion (1370); while articulation band (1314) is laterally interposed between rings (1320) and ribbed body portion (1380). Rings (1320) are configured to keep articulation bands (1310, 1314) in a parallel relationship, particularly when articulation section (1300) is in a bent configuration (e.g., similar to the configuration shown in FIG. 20B). In other words, when articulation band (1310) is on the inner diameter of a curved configuration presented by a bent articulation section (1300), rings (1320) may retain articulation band (1310) such that articulation band (1310) follows a curved path that complements the curved path followed by articulation band (1314). It should be understood that channels (1374, 1378) are sized to accommodate respective articulation bands (1310, 1314) in such a way that articulation bands (1310, 1314) may still freely slide through articulation section (1300), even with rings (1320) being secured to ribbed body portions (1370, 1380). It should also be understood that rings (1320) may be secured to ribbed body portions (1370, 1380) in various ways, including but not limited to interference fitting, adhesives, welding, etc.

Figure 40:
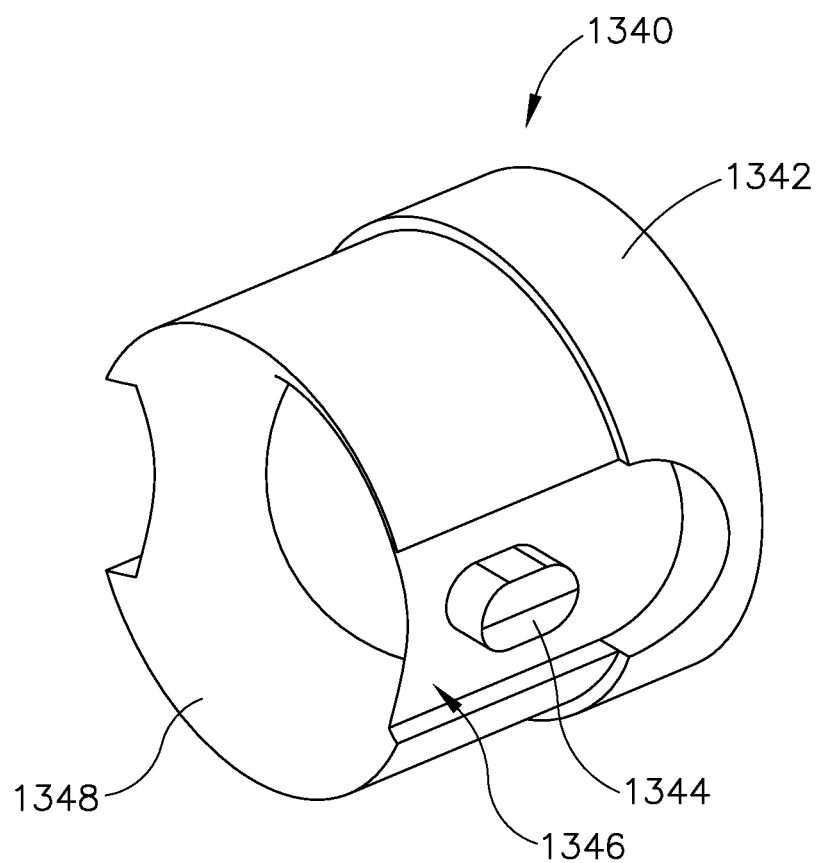
FIG. 40 depicts a perspective view of a distal collar of the articulation section of FIG. 36.
Figure 41:
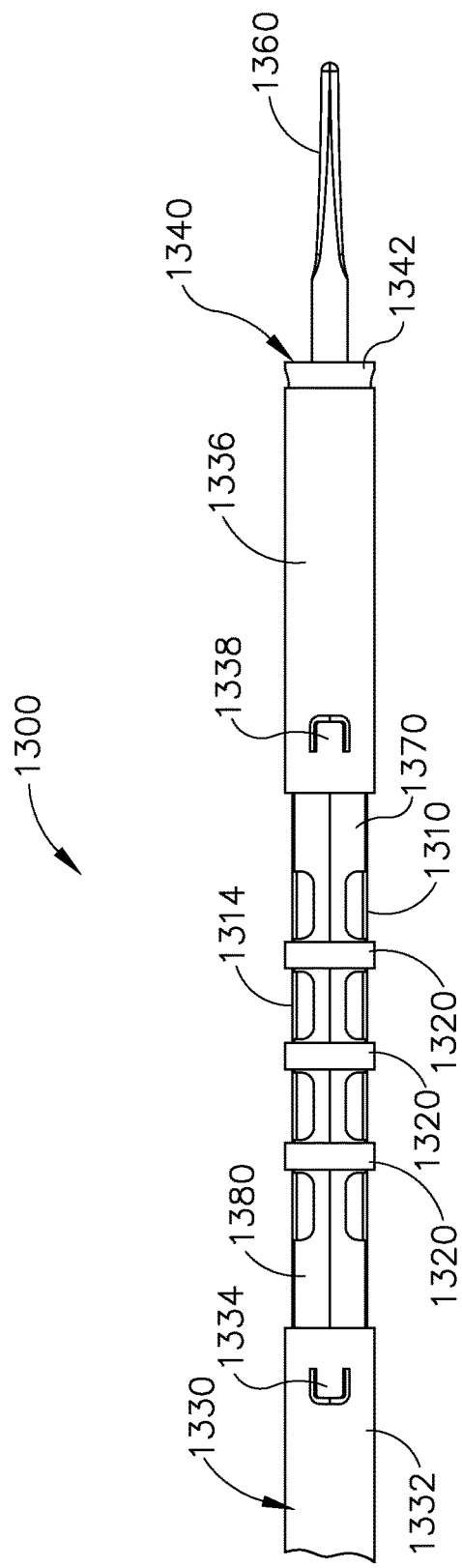
FIG. 41 depicts a top elevational view of the articulation section of FIG. 36.

FIG. 40 shows distal collar (1340) in greater detail. Distal collar (1340) includes a distal flange (1342), a pair of outwardly extending projections (1344), a pair of lateral recesses (1346), and a convexly tapering inner surface (1348). Distal flange (1342) is configured to engage the distal edge of distal outer tube (1336), such that distal flange (1342) mechanically grounds distal collar (1340) against distal outer tube (1336). Outwardly extending projections (1344) are configured to fit in respective distal openings (1311, 1315) of articulation bands (1310, 1314). Articulation bands (1310, 1314) are thus secured to distal collar (1340) via projections (1344). Lateral recesses (1346) accommodate respective portions of articulation bands (1310, 1314) that are adjacent to distal openings (1311, 1315). It should also be understood that articulation bands (1310, 1314) also include proximal openings (1313, 1317) that are used to couple articulation bands (1310, 1314) with articulation drive features that are operable to translate articulation bands (1310, 1314) longitudinally in an opposing fashion, as taught above.

Articulation section (1300) of this example operates substantially similar to articulation section (900) described above. When articulation bands (1310, 1314) are translated longitudinally in an opposing fashion, a moment is created and applied to nodal distal flange (1394) through distal outer tube (1336). This causes articulation section (1300) and narrowed section (1364) of waveguide (1366) to articulate, without transferring axial forces in articulation bands (1310, 1314) to waveguide (1366). In particular, as best seen in FIG. 42, articulation section (1300) of the present example maintains a gap (1345) between the proximal end of distal collar (1340) and nodal distal flange (1394) of waveguide (1366), such that collar (1340) does not bear proximally against a distally facing surface of distal flange (1394), even when articulation section (1300) is in a bent state. Thus, nodal distal flange (1394) only receives laterally directed bearing forces (by distal outer tube (1336) and/or bands (1310, 1314)) when being driven to an articulated position.

It should be understood that one articulation band (1310, 1314) may be actively driven distally while the other articulation band (1310, 1314) is passively permitted to retract proximally. As another merely illustrative example, one articulation band (1310, 1314) may be actively driven proximally while the other articulation band (1310, 1314) is passively permitted to advance distally. As yet another merely illustrative example, one articulation band (1310, 1314) may be actively driven distally while the other articulation band (1310, 1314) is actively driven proximally. Various suitable ways in which articulation bands (1310, 1314) may be driven will be apparent to those of ordinary skill in the art in view of the teachings herein.

In the discussion of the examples shown in FIGS. 18A-18B, it was noted how boss surfaces (822) of ribbed body (810) engage each other when ribbed body (810) is bent to the configuration shown in FIG. 18A, such that boss surfaces (822) provide a hard stop that restricts the bend angle of articulation section (800). The same principle may apply to articulation section (1300) shown in FIGS. 36-42. In particular, ribs (1372, 1382) of the present example may include opposing surfaces that act as boss surfaces that engage each other on one side of articulation section (1300) when articulation section (1300) reaches a fully articulated state. Such surfaces may thus restrict the bend angle of articulation section (1300) (e.g., to prevent narrowed section (1364) of waveguide (1366) from overbending, etc.). In addition or in the alternative, rings (1320) may eventually contact each other during articulation to restrict the bend angle of articulation section (1300). Other suitable ways in which the bend angle of articulation section (1300) may be restricted will be apparent to those of ordinary skill in the art in view of the teachings herein.

While articulation bands (1310, 1314) are secured to distal collar (1340) in the present example, it should be understood that articulation bands (1310, 1314) may instead be secured directly to respective lateral sides of nodal distal flange (1394). It should also be understood that, when articulation bands (1310, 1314) are translated in an opposing fashion in such versions, articulation section (1300) may bend as taught elsewhere herein. Distal collar (1340) may thus be eliminated, if desired. Furthermore, distal outer tube (1336) may be eliminated in such versions, if desired. Still other suitable variations of articulation section (1300) will be apparent to those of ordinary skill in the art in view of the teachings herein.

V. Exemplary Alternative Shaft Assembly

In any of the foregoing examples, shaft assembly (30) may be provided in a modular form, such that a distal portion of shaft assembly (30) is removable from a proximal portion of shaft assembly (30). By way of example only, this may permit re-use of the proximal portion of shaft assembly (30) and handle assembly (20) while the distal portion of shaft assembly (30) is disposed of after use. As another merely illustrative example, various kinds of end effectors (40) may be used with the same handle assembly (20) when a distal portion of shaft assembly (30) is removable from a proximal portion of shaft assembly (30). Other kinds of scenarios in which it may be desirable to provide removability of a distal portion of shaft assembly (30) from a proximal portion of shaft assembly (30) will be apparent to those of ordinary skill in the art in view of the teachings herein. The following provides one merely illustrative example of a way in which a distal portion of shaft assembly (30) may be removable from a proximal portion of shaft assembly (30). Various suitable ways in which the following teachings may be combined with the above teachings will be apparent to those of ordinary skill in the art in view of the teachings herein. Similarly, various other suitable ways in which distal portion of shaft assembly (30) may be removable from a proximal portion of shaft assembly (30) will be apparent to those of ordinary skill in the art in view of the teachings herein.

FIGS. 43A-44B show an exemplary alternative shaft assembly (1200). Shaft assembly (1200) is configured to operate substantially similar to shaft assembly (30) discussed above except for the differences discussed below. Shaft assembly (1200) comprises a reusable proximal section (1210) and a disposable distal section (1220). Proximal section (1210) and distal section (1220) of shaft assembly (1200) each include an outer sheath (1232A, 1232B) that encloses the drive features and the acoustic transmission features discussed above with respect to instrument (10). Proximal section (1210) of shaft assembly (1200) extends distally from handle assembly (20). A distal end of proximal section (1210) terminates in a connection portion (1212) that will be discussed in more detail below. Articulation section (130) is located at a distal end of distal section (1220) of shaft assembly (1200), with end effector (40) being located distal to articulation section (130). A proximal end of distal section (1220) comprises a connection portion (1222) that will be discussed in more detail below.

Connection portion (1212) comprises a bayonet pin (1214) configured to couple with a mating bayonet slot (1224) of connection portion (1222) to thereby provide coupling between proximal section (1210) and distal section (1220). In particular, bayonet features (1214, 1224) secure sections (1210, 1220) together after pin (1214) is first inserted longitudinally in slot (1224) and is then rotated in slot (1224). While bayonet features (1214, 1224) provide coupling between proximal section (1210) and distal section (1220) in the present example, it should be understood that any other suitable type of coupling may be used.

Figure 43A:
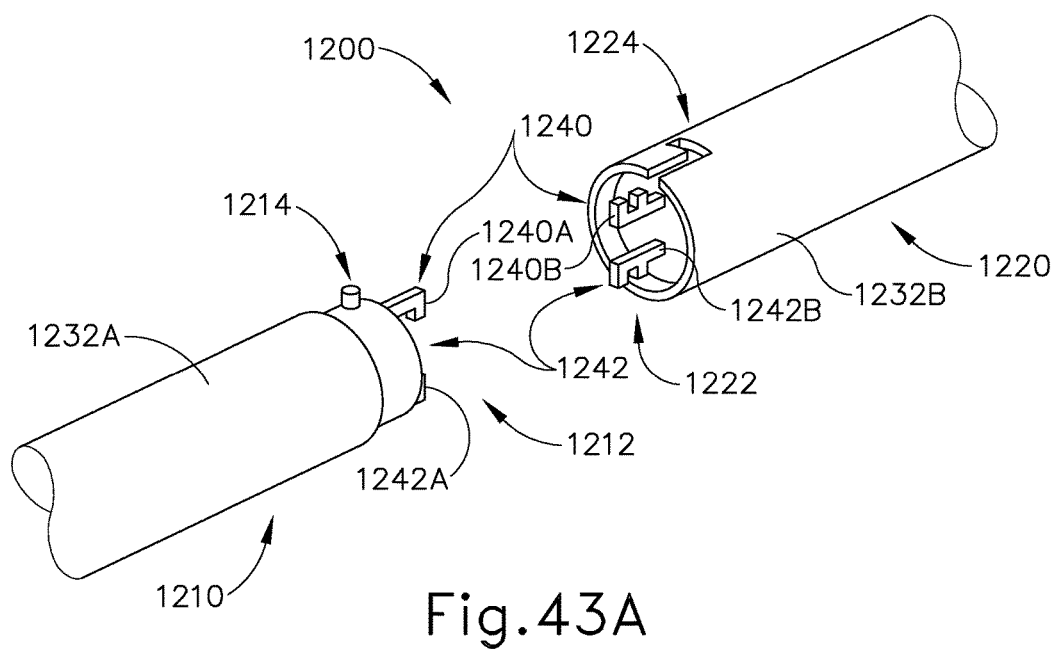
FIG. 43A depicts a perspective view of an exemplary alternative shaft assembly with a reusable portion and a disposable portion disconnected.
Figure 43B:
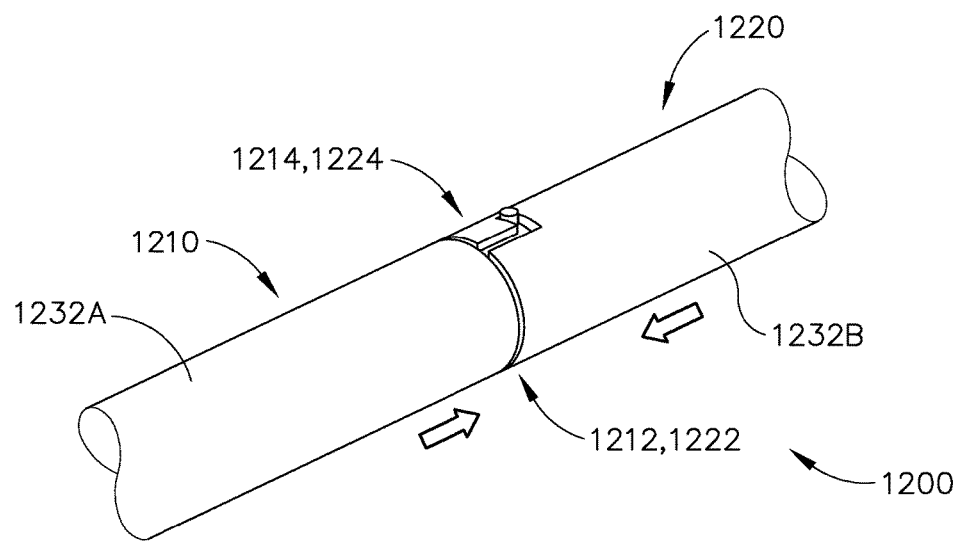
FIG. 43B depicts a perspective view of the shaft assembly of FIG. 43A with the reusable portion and the disposable portion connected.
Figure 44A:
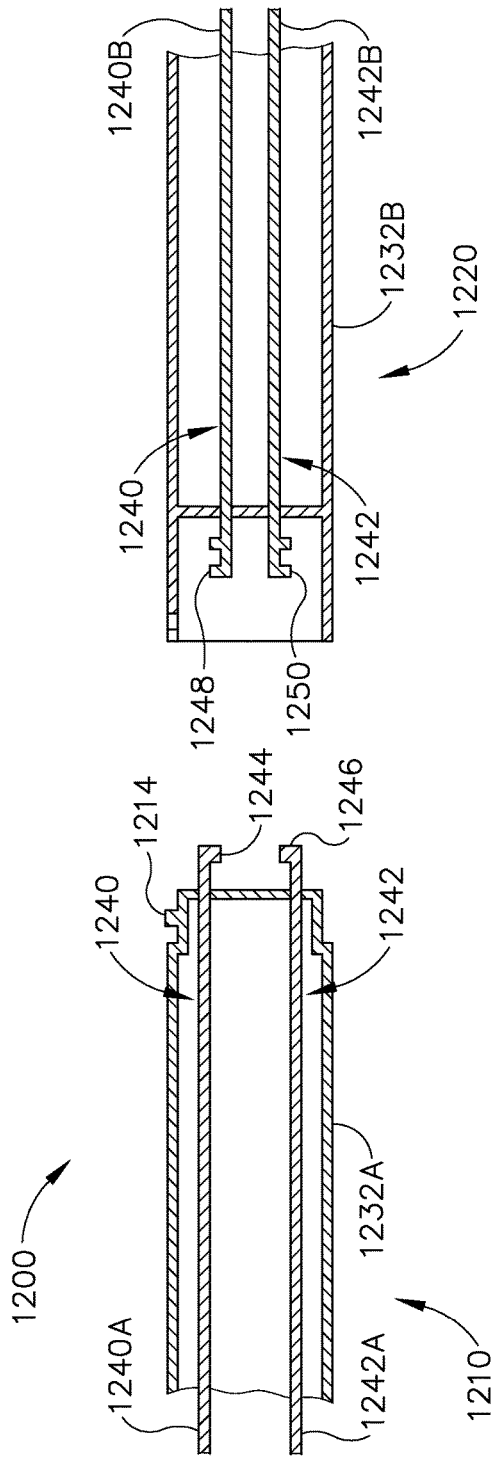
FIG. 44A depicts a cross-sectional side view of the shaft assembly of FIG. 43A with the reusable portion and the disposable portion disconnected.
Figure 44B:
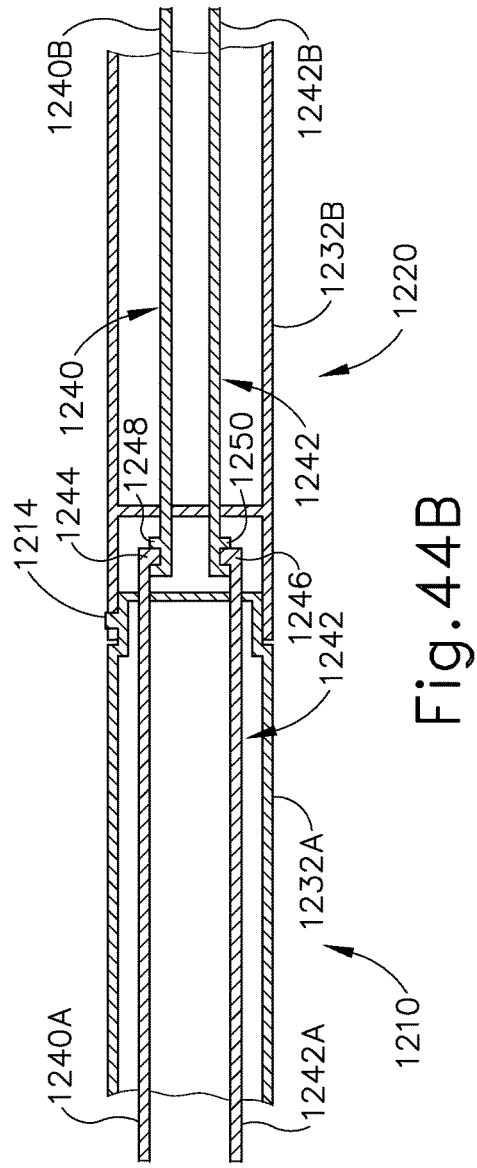
FIG. 44B depicts a cross-sectional side view of the shaft assembly of FIG. 43A with the reusable portion and the disposable portion connected.

A pair of articulation bands (1240, 1242) extend through proximal section (1210) and distal section (1220). Articulation bands (1240, 1242) each comprise reusable portions (1240A, 1242A) and disposable portions (1240B, 1242B). As best seen in FIGS. 43A and 44A, distal ends of reusable portions (1240A, 1242A) of articulation bands (1240, 1242) extend distally from connection portion (1212). Distal ends of reusable portions (1240A, 1242A) each present a first mating feature (1244, 1246). Proximal ends of disposable portions (1240B, 1242B) of articulation bands (1240, 1242) extend proximally from connection portion (1222). Proximal ends of disposable portions (1240B, 1242B) each present a second mating feature (1248, 1250). Second mating features (1248, 1250) are configured to engage with respective first mating features (1244, 1246) when proximal section (1210) and distal section (1220) are coupled together as shown in FIGS. 43B and 44B. Mating features (1244, 1246, 1248, 1250) allow for longitudinal movement of reusable portions (1240A, 1242A) of articulation bands (1240, 1242) to be communicated to disposable portions (1240B, 1242B) of articulation bands (1240, 1242). In other words, portions (1240A, 1240B) will translate unitarily when mating features (1244, 1248) are coupled together; and portions (1242A, 1242B) will translate unitarily when mating features (1248, 1250) are coupled together. Various other suitable ways in which portions of articulation bands (1240, 1242) may be selectively coupled together will be apparent to those of ordinary skill in the art in view of the teachings herein. Similarly, various other suitable ways in which other portions of shaft assembly (30) may be selectively coupled together will be apparent to those of ordinary skill in the art in view of the teachings herein.

VI. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus for operating on tissue, the apparatus comprising:
   (a) an ultrasonic transducer;
   (b) a shaft, wherein the shaft defines a longitudinal axis;
   (c) an acoustic waveguide, wherein the waveguide is acoustically coupled with the transducer, wherein the waveguide comprises a flexible portion;
   (d) an articulation section coupled with the shaft, wherein a portion of the articulation section encompasses the flexible portion of the waveguide, wherein the articulation section further includes a collar that encircles the waveguide at a location distally of the flexible portion, wherein the collar defines a distal end of the articulation section;
   (e) an end effector comprising an ultrasonic blade in acoustic communication with the waveguide;
   (f) an articulation drive assembly, wherein the articulation drive assembly comprises at least one translating articulation driver having a distal end attached directly to the collar, wherein the translating articulation driver is operable to drive the collar laterally relative to the longitudinal axis and thereby articulate the articulation section about the flexible portion of the waveguide; and
   (g) an outer tube disposed over the collar, wherein the outer tube is fixed axially relative to the collar, wherein the distal end of the at least one translating articulation driver is interposed between the collar and the outer tube.

2. The apparatus of claim 1, wherein the waveguide further comprises a nodal portion arranged distally of the flexible portion, wherein the outer tube extends over the nodal portion, wherein a portion of the translating articulation driver is interposed between the outer tube and the nodal portion of the waveguide.

3. The apparatus of claim 1, wherein the waveguide includes:
   (i) a first nodal portion arranged proximally of the flexible portion,
   (ii) a second nodal portion arranged distally of the flexible portion, and
   (iii) at least one flat lateral region extending longitudinally between the first and second nodal portions,
   wherein the at least one translating articulation driver extends along the at least one flat lateral region.

4. The apparatus of claim 1, wherein the articulation section comprises a set of ribs separated by gaps configured to promote flexing of the articulation section, wherein the ribs include surfaces positioned to engage each other in response to the articulation section reaching a fully articulated state, such that the engaged surfaces of the ribs are configured to restrict a bend angle of the articulation section in the fully articulated state.

5. The apparatus of claim 1, wherein the articulation section comprises a set of ribs separated by gaps configured to promote flexing of the articulation section, wherein the articulation section further comprises a set of rings associated with the set of ribs, wherein the at least one translating member is laterally interposed between the set of rings and the set of ribs.

6. The apparatus of claim 1, wherein the shaft comprises a first portion and a second portion, wherein at least a first translating articulation driver extends through the first portion of the shaft, wherein at least a second translating articulation driver extends through the second portion of the shaft, wherein the first portion of the shaft is configured to couple with the second portion of the shaft, and wherein the at least a first translating articulation driver is configured to mechanically engage the at least a second translating articulation driver when the first portion of the shaft is coupled with the second portion of the shaft.

7. An apparatus for operating on tissue, the apparatus comprising:
(a) an ultrasonic transducer operable to convert electrical power into ultrasonic vibrations;
(b) a waveguide acoustically coupled with the ultrasonic transducer, wherein the waveguide includes a flexible portion;
(c) a shaft, wherein the shaft defines a longitudinal axis;
(d) an articulation section coupled with the shaft and including:
  (i) a first ribbed body half having:
    (A) a first plurality of longitudinally spaced ribs, and
    (B) a first channel extending longitudinally through the first plurality of longitudinally spaced ribs, and
  (ii) a second ribbed body half, wherein the second ribbed body half is configured to mate with the first ribbed body half to encircle the flexible portion of the waveguide, wherein the second ribbed body half has:
    (A) a second plurality of longitudinally spaced ribs, and
    (B) a second channel extending longitudinally through the second plurality of longitudinally spaced ribs,
  wherein the longitudinally spaced ribs are configured to promote flexing of the articulation section relative to the longitudinal axis,
  wherein the flexible portion of the waveguide is configured to deflect with the articulation section;
(e) an end effector coupled with the articulation section, wherein the end effector comprises an ultrasonic blade in acoustic communication with the ultrasonic transducer via the waveguide; and
(f) an articulation drive assembly operable to drive articulation of the articulation section to thereby deflect the end effector from the longitudinal axis, wherein the articulation drive assembly includes:
  (i) a first elongate member arranged within the first channel, and
  (ii) a second elongate member arranged within the second channel,
  wherein the first and second elongate members are operable to translate longitudinally through the respective channels to thereby cause articulation of the articulation section.

8. An apparatus for operating on tissue, comprising:
(a) an ultrasonic transducer configured to generate an ultrasonic vibration;
(b) a shaft defining a longitudinal axis;
(c) an acoustic waveguide coupled with the ultrasonic transducer,
wherein the acoustic waveguide includes:
  (i) a proximal nodal flange arranged at a second-to-distal-most acoustic node of the acoustic waveguide, wherein the proximal nodal flange includes a first flat,
  (ii) a distal nodal flange arranged at a distal-most acoustic node of the acoustic waveguide, wherein the distal nodal flange includes a second flat, and
  (iii) an intermediate section extending longitudinally between the proximal and distal nodal flanges, wherein the intermediate section includes a flexible portion that is narrowed relative to a remaining portion of the intermediate section, wherein the flexible portion and the distal node are arranged distally of a distal end of the shaft;
an articulation section coupled with the distal end of the shaft, wherein the articulation section includes a body portion defining an internal passage through which the flexible portion of the waveguide extends, wherein the articulation section and the flexible portion are configured to deflect together relative to the longitudinal axis;
an ultrasonic blade acoustically coupled to the waveguide and projecting distally directly from the distal nodal flange, wherein the waveguide is configured to communicate the ultrasonic vibration from the ultrasonic transducer to the ultrasonic blade; and
an articulation drive assembly operatively connected to the articulation section, wherein the articulation drive assembly includes an articulation driver arranged radially outward of and extending along the body portion of the articulation section and the first and second flats of the waveguide, wherein the articulation driver is operable to collectively deflect the articulation section and the flexible portion of the waveguide from a first configuration to a deflected second configuration.

9. The apparatus of claim 8, wherein the articulation section includes a collar positioned distally from the distal nodal flange of the waveguide, wherein the articulation driver is affixed to the collar, wherein the articulation driver is configured to translate from a first position to a second position, wherein the articulation section and the flexible portion of the waveguide are configured to deflect from the first configuration to the deflected second configuration in response to translation of the articulation driver from the first position to the second position.

10. The apparatus of claim 8, wherein the waveguide further includes a flat lateral region extending longitudinally between the proximal and distal nodal flanges.

* * * * *